(12) United States Patent
Jayasena et al.

(10) Patent No.: US 6,183,967 B1
(45) Date of Patent: *Feb. 6, 2001

(54) NUCLEIC ACID LIGAND INHIBITORS TO DNA POLYMERASES

(75) Inventors: Sumedha Jayasena; Larry Gold, both of Boulder, CO (US)

(73) Assignee: NeXstar Pharmaceuticals, Boulder, CO (US)

( * ) Notice: Under 35 U.S.C. 154(b), the term of this patent shall be extended for 0 days.

This patent is subject to a terminal disclaimer.

(21) Appl. No.: 09/258,797

(22) Filed: Mar. 1, 1999

Related U.S. Application Data

(63) Continuation-in-part of application No. 08/945,734, filed on Oct. 28, 1997, now Pat. No. 6,020,130, which is a continuation-in-part of application No. 08/487,426, filed on Jun. 7, 1995, now Pat. No. 5,763,173, and a continuation-in-part of application No. 08/487,720, filed on Jun. 7, 1995, now Pat. No. 5,874,557, and a continuation-in-part of application No. 08/484,557, filed on Jun. 7, 1995, now Pat. No. 5,693,502.

(51) Int. Cl.[7] ............... C12Q 1/68; C12Q 19/34; C07H 21/02; C07H 21/04; C12N 9/12

(52) U.S. Cl. ............... 435/6; 435/91.2; 435/194; 536/23.1; 536/25.4

(58) Field of Search .................. 435/6, 91.219, 435/194; 536/25.4, 23.1

(56) References Cited

U.S. PATENT DOCUMENTS

| | | | |
|---|---|---|---|
| 5,270,163 | 12/1993 | Gold et al. | 435/6 |
| 5,338,671 | 8/1994 | Scalice et al. | 435/91.2 |
| 5,459,015 | 10/1995 | Janjic et al. | 435/6 |
| 5,472,841 | 12/1995 | Jayasena et al. | 435/6 |
| 5,475,096 | 12/1995 | Gold et al. | 435/6 |
| 5,476,766 | 12/1995 | Gold et al. | 435/6 |
| 5,496,938 | 3/1996 | Gold et al. | 536/22.1 |
| 5,503,978 | 4/1996 | Schneider et al. | 435/6 |
| 5,527,894 | 6/1996 | Gold et al. | 435/6 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 536/22.1 |
| 5,595,877 | 1/1997 | Gold et al. | 435/6 |
| 5,693,502 | * 12/1997 | Gold et al. | 435/91.2 |
| 5,723,323 | 3/1998 | Kauffman et al. | 435/6 |
| 5,763,173 | * 6/1998 | Gold et al. | 435/6 |
| 5,874,557 | * 2/1999 | Gold et al. | 536/22.1 |
| 6,020,130 | * 2/2000 | Gold et al. | 435/6 |

FOREIGN PATENT DOCUMENTS

| | | |
|---|---|---|
| 0 592 035 A2 | 4/1994 | (EP) . |
| 2 183 661 | 6/1987 | (GB) . |
| WO 89/06694 | 7/1989 | (WO) . |
| WO 91/19813 | 12/1991 | (WO) . |
| WO 92/14843 | 9/1992 | (WO) . |
| WO 94/25037 | 11/1994 | (WO) . |

OTHER PUBLICATIONS

Szostak, "Structure and Activity of Ribozymes, " in *Redesigning the Molecules of Life*, (S.A. Benner ed.) Springer–Verlag Berlin Heidelberg, pp. 87–113, (1988).

Boiziau et al. (1995) Nucleic Acids Research 23:64.

Bloch (1992) Applications, A Forum for PCR Users, Issue 8, pp. 6–9.

Chen and Gold (1994) Biochemistry 33:8746.

Ellington & Szostak (1990) Abstracts of papers presented at the 1990 meeting on RNA Processing, Cold Spring Harabor Laboratory, Cold Spring Harbor, NY, p. 84.

Fujihashi et al. (1995) AIDS Research and Human Retroviruses 11:461.

Hacia et al. (1994) Biochemistry 33:6192.

Joyce (1989) Gene 82:83.

Joyce & Inoue (1989) Nucleic Acids Research 17:711.

Kellogg et al. (1994) BioTechniques 16:1134.

Kinzler & Vogelstein (1989) Nucleic Acids Research 17:3645.

Kramer et al. (1974) J. Mol. Biol. 89:719.

Levisohn & Spiegelman (1969) Proc. Natl. Acad. Sci. USA 63:805.

Levisohn & Spiegelman (1968) Proc. Natl. Acad. Sci. USA 60:866.

Matsukura et al. (1995) Toxicology Letters 82/83:435.

Meyers and Gelfand (1991) Biochemistry 30:7661.

Oliphant et al. (1989) Mol. Cell. Biol. 9:2944.

Oliphant & Struhl (1988) Nucleic Acids Research 16:7673.

Oliphant & Struhl (1987) Methods in Enzymology 155:568.

Oliphant et al. (1986) Gene 44:177.

Robertson & Joyce (1990) Nature 344:467.

Takase–Yoden et al. (1995) Antiviral Research 28:359.

Tamura et al. (1995) Nucleic Acids Research 34:93.

Thiesen & Bach (1990) Nucleic Acids Research 18:3203.

Tökés and Aradi (1995) Biochimica et Biophysica Acta 1261:115.

Tuerk et al. (1992) Proc. Natl. Acad. Sci. USA 89:6988.

\* cited by examiner

*Primary Examiner*—Stephanie W. Zitomer
(74) *Attorney, Agent, or Firm*—Swanson & Bratschun LLC

(57) ABSTRACT

This invention discloses high-affinity oligonucleotide ligands to the thermostable Taq polymerase, Tth polymerase and TZ05 polymerase. Specifically, this invention discloses DNA ligands having the ability to bind to the Taq, Tth and TZ05 polymerases and the methods for obtaining such ligands. The ligands are capable of inhibiting polymerases at any predetermined temperature.

21 Claims, 40 Drawing Sheets

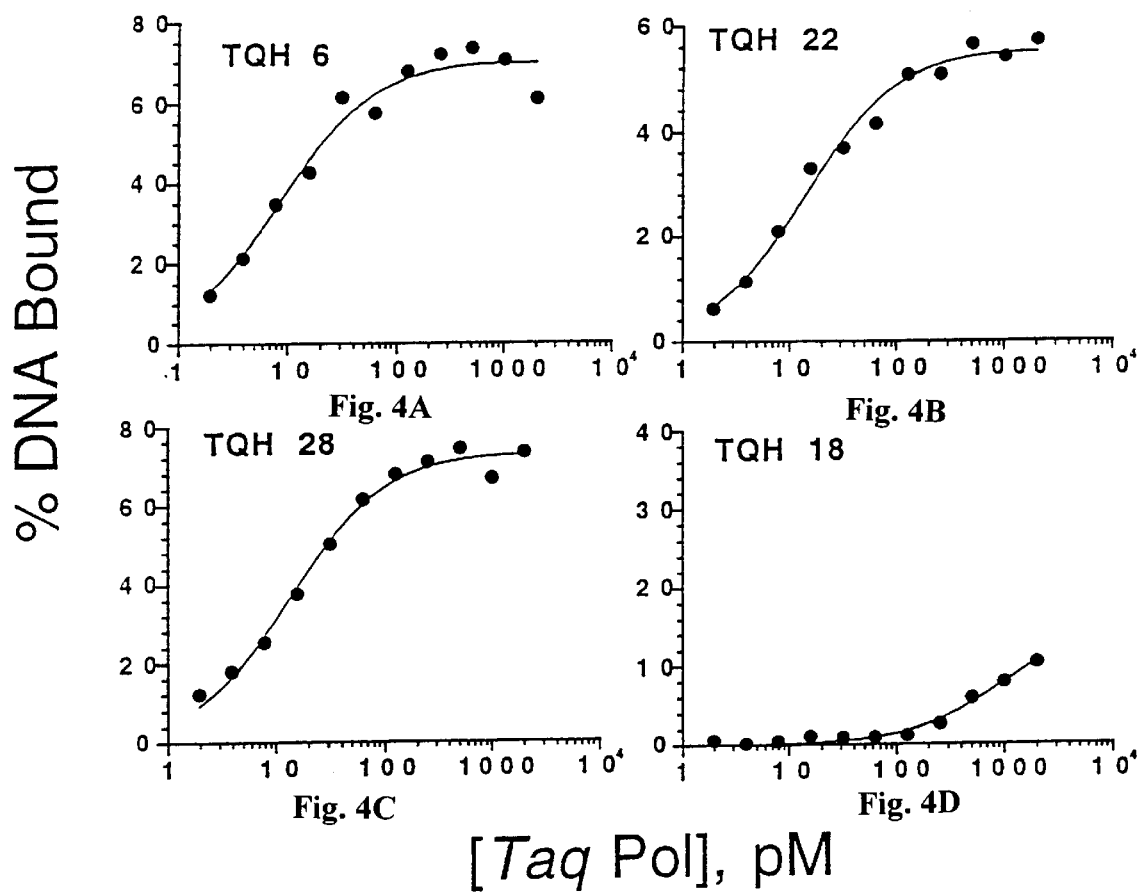
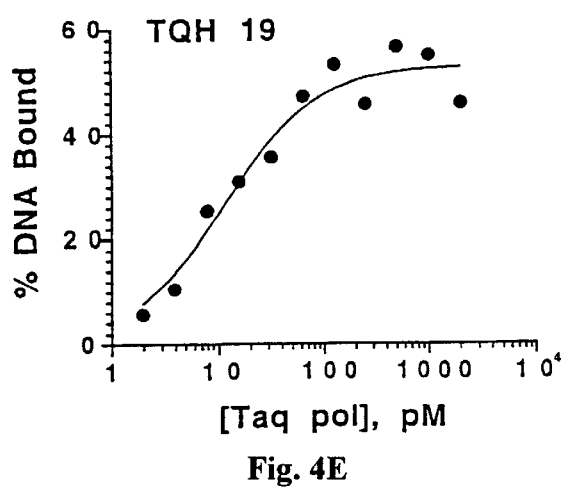

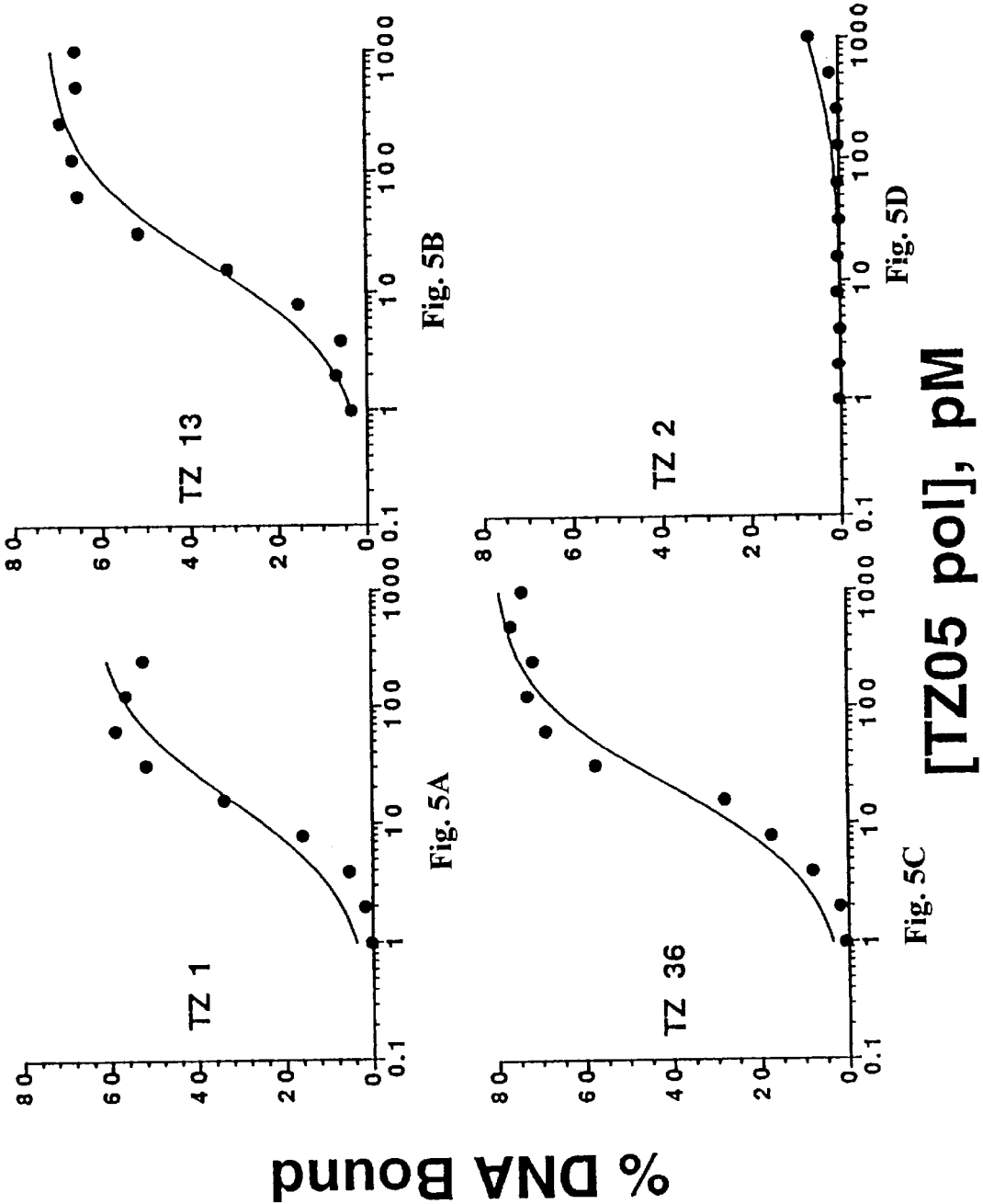

Polymerase Activity Assay
SEQ ID NO:6
↓ Polymerase
dNTPs
M$^{++}$
SEQ ID NO:119
Fig. 6

Temp. (°C) 35 40 45 50 55 60 65

TZ 1

Temp. (°C) 35 40 45 50 55 60 65

TZ 3

Temp. (°C) 35 40 45 50 55 60 65

TZ 9

35 40 45 50 55 60 65

TZ 2

35 40 45 50 55 60 65

TZ 8

35 40 45 50 55 60 65

TZ 13

51-nt Truncates

| SEQ ID NO: | | |
|---|---|---|
| 107 | TZ1 | 5'-TGGCGGAGCACACCGGGGGGGCTGCGGGCAAGGCGGGTGTCTTGTGTATGA-3' |
| 108 | TZ13 | 5'-TGGCGGAGCACGTCGGGGGGCGTTGGGACGGGCAGACGTCTTGTGTATGA-3' |
| 109 | TZ36 | 5'-TGGCGGAGCACGGGAGGGTGTGGAGTGGGCGCGGGCTCTTGTGTATGA-3' |

51-nt Truncates with phosphorothioate linkages

| 110 | TZ1 | 5'-T*G*G*C*G*G*A*G*C*ACACCGGGGGGGCTGCGGGCAAGGCGGGTGTCTTGTGTATGA-3' |
| 111 | TZ13 | 5'-T*G*G*C*G*G*A*G*C*ACGTCGGGGGGCGTTGGGACGGGCAGACGTCTTGTGTATGA-3' |
| 112 | TZ36 | 5'-T*G*G*C*G*G*A*G*C*ACGGGAGGGTGTGGAGTGGGCGCGGGCTCTTGTGTATGA-3' |

30-nt Truncates

| 113 | TZ1 | 5'-ACACCGGGGGGGCTGCGGGCAAGGCGGGTG-3' |
| 114 | TZ13 | 5'-ACGTCGGGGGGCGTTGGGACGGGCAGACG-3' |
| 115 | TZ36 | 5'-ACGGGAGGGTGTGGAGTGGGCGCGGGGC-3' |

Underligned and italicized letters indicate nucleotides from fixed regions

* Indicates phosphorothioate linkages

Fig. 33

| SEQ ID NO: | | |
|---|---|---|
| 116 | TZ13-Tandem Dimer | 5'-ACGTCGGGGGCCGTTGGGACGGGCAGACG-T‑T |
| | | 3'-GCAGACGGGCAGGGTTGCGGGGCTGCA-T |
| 117 | TZ13-Symmetric Dimer 1 | 5'-ACGTCGGGGGCCGTTGGGACGGGCAGACGTT‑T‑X |
| | | 5'-ACGTCGGGGGCCGTTGGGACGGGCAGACGTT‑T |
| 118 | TZ13-Symmetric Dimer 2 | 5'-ACGTCGGGGGCCGTTGGGACGGGCAGACG-L‑X |
| | | 5'-ACGTCGGGGGCCGTTGGGACGGGCAGACG-L |

NUCLEIC ACID LIGAND INHIBITORS TO DNA POLYMERASES

RELATED APPLICATIONS

This application is a continuation in part of U.S. patent application Ser. No. 08/945,734, filed Oct. 28, 1997, entitled "Nucleic Acid Ligands that Bind to and Inhibit DNA Polymerases," now U.S. Pat. No. 6,020,130, which is a continuation in part of U.S. patent application Ser. No. 08/487,426, filed Jun. 7, 1995, now U.S. Pat. No. 5,763,173, U.S. patent application Ser. No. 08/487,720, filed Jun. 7, 1995, now U.S. Pat. No. 5,874,557, and U.S. patent application Ser. No. 08/484,557, filed Jun. 7, 1995, now U.S. Pat. No. 5,693,502, each of which is entitled "Nucleic Acid Ligand Inhibitors to DNA Polymerases."

FIELD OF THE INVENTION

Described herein are methods for identifying and preparing high-affinity nucleic acid ligands to DNA polymerases, specifically thermostable DNA polymerases. In a preferred embodiment the DNA polymerase is Taq polymerase, a thermostable polymerase isolated from *Thermus aquaticus;* Tth polymerase, a thermostable DNA polymerase isolated from *Thermus thermophilus;* or TZ05 polymerase, isolated from another Thermus species. However, the method of this invention can be extended to the identification and preparation of any thermally stable DNA polymerase. Some of these thermostable DNA polymerases also have the ability to reverse transcribe RNA to copy DNA. Examples of DNA polymerases with reverse transcription ability include Tth and TZ05 polymerase. The method utilized herein for identifying such nucleic acid ligands is called SELEX, an acronym for Systematic Evolution of Ligands by EXponential Enrichment. Also described herein is an improved method for performing the Polymerase Chain Reaction using the nucleic acid ligands of this invention. Specifically disclosed herein are high-affinity nucleic acid ligands to Taq polymerase, Tth polymerase, and TZ05 polymerase. The invention includes high-affinity DNA ligands which bind to Taq polymerase, Tth polymerase and TZ05 polymerase, thereby inhibiting their polymerase activity at a predetermined range of temperatures. Further included within this invention are nucleic acid switches. The temperature dependent binding of the nucleic acid ligands to DNA polymerases of this invention are examples of ligands whose desirable properties can be switched on or off based on any number of reaction conditions, such as pH and salt concentration.

BACKGROUND OF THE INVENTION

The Polymerase Chain Reaction (PCR), is a recently developed technique which has had a significant impact in many areas of science. PCR is a rapid and simple method for specifically amplifying a target DNA sequence in an exponential manner. (Saiki et al. (1985) Science 230:1350; Mullis and Faloona (1987) Methods Enzymol. 155:335). Briefly, the method consists of synthesizing a set of primers that have nucleotide sequences complementary to the DNA that flanks the target sequence. The primers are then mixed with a solution of the target DNA, a thermostable DNA polymerase and all four deoxynucleotide triphosphates (dATP, dTTP, dCTP and dGTP). The solution is then heated to a temperature sufficient to separate the complementary strands of DNA (approximately 95° C.) and then cooled to a temperature sufficient to allow the primers to bind to the flanking sequences. The reaction mixture is then heated again (to approximately 72° C.) to allow the DNA synthesis to proceed. After a short period of time, the temperature of the reaction mixture is once again raised to a temperature sufficient to separate the newly formed double-stranded DNA, thus completing the first cycle of PCR. The reaction mixture is then cooled and the cycle is repeated. Thus, PCR consists of repetitive cycles of DNA melting, annealing and synthesis. Twenty replication cycles can yield up to a million fold amplification of the target DNA sequence. The ability to amplify a single DNA molecule by PCR has applications in environmental and food microbiology (Wemars et al. (1991) Appl. Env. Microbiol. 57:1914–1919; Hill and Keasler (1991) Int. J. Food Microbiol. 12:67–75), clinical microbiology (Wages et al. (1991) J. Med. Virol. 33:58–63; Sacramento et al. (1991) Mol. Cell Probes 5:229–240; Laure et al. (1988) Lancet 2:538), oncology (Kumar and Barbacid (1988) Oncogene 3:647–651; McCormick (1989) Cancer Cells 1:56–61; Crescenzi et al. (1988) Proc. Natl. Acad. Sci. U.S.A. 85:4869), genetic disease prognosis (Handyside et al (1990) Nature 344:768–770), blood banking (Jackson (1990) Transfusion 30:51–57) and forensics (Higuchi et al. (1988) Nature (London) 332:543).

The availability of thermostable DNA polymerases such as Taq DNA polymerase has both simplified and improved PCR. Originally only heat-sensitive polymerases, such as *E. coli* DNA polymerase were available for use in PCR. Heat-sensitive polymerases, however, are destroyed at the temperatures required to melt double-stranded DNA and additional polymerase has to be added after each PCR cycle. Taq DNA polymerase, isolated from the thermophilic bacterium *Thermus aquaticus,* is stable up to 95° C. and its use in PCR has eliminated the necessity of repetitive addition of temperature sensitive polymerases after each thermal cycle. Additionally, because Taq polymerase can be used at higher temperatures it has improved the specificity and sensitivity of PCR. The reason for the improved specificity is that at higher temperatures the binding of primers to sites other that the desired ones (referred to as mispriming) is significantly reduced.

Since its discovery, the Polymerase Chain Reaction has been modified for various applications, such as in situ PCR, in which the detection limit of traditional in situ hybridization has been pushed to the single copy level (Haase et al. (1990) Proc. Natl. Acad. Sci. U.S.A. 87:4971–4975), and reverse transcriptase PCR (RT-PCR), wherein an RNA sequence is converted to its copy DNA (cDNA) by reverse transcriptase (RT) before being amplified by PCR, making RNA a substrate for PCR (Kawasaki (1991) Amplification of RNA in *PCR Protocols, A Guide to Methods and Applications,* Innis et al., Eds. Academic Press Inc., San Diego, Calif., 21–27). Mesophilic viral reverse transcriptases, however, are often unable to synthesize full-length cDNA molecules because they cannot "read through" stable secondary structures of RNA molecules. This limitation has recently been overcome by use of a polymerase isolated from *Thermus thermophilus* (Tth polymerase). Tth polymerase is a thermostable polymerase that can function as both reverse transcriptase and DNA polymerase (Myers and Gelfand (1991) Biochemistry 30:7661–7666). The reverse transcription performed at an elevated temperature using Tth polymerase eliminates secondary structures of template RNA, making it possible for the synthesis of full-length cDNA.

Although significant progress has been made in PCR technology, the amplification of nontarget oligonucleotides due to side-reactions, such as mispriming of background DNA and/or primer oligomerization still presents a significant problem. This is especially true in diagnostic applications in which PCR is carried out in a milieu containing background DNA while the target DNA may be present in a single copy (Chou et al. (1992) Nucleic Acid Res. 20:1717–1723). The generation of nonspecifically amplified products has been attributed to polymerase activity at ambient temperature that extends nonspecifically annealed primers. (Chou et al. (1992) Nucleic Acid Res. 20:1717–1723, Li et al. (1990) Proc. Natl. Acad. Sci. U.S.A. 87:4580). Accordingly, the inhibition of polymerase activity at ambient temperature is important to control the generation of non-specific products.

Two methods have been reported which minimize these side reactions. In the first method, termed "manual hot start" PCR, a component critical to polymerase activity (e.g. divalent ions and/or the polymerase itself) is not added to the reaction mixture until the temperature of the mixture is high enough to prevent nonspecific primer annealing. (Chou et al. (1992) Nucleic Acid Res. 20:1717–1723; D'Aquila et al. (1991) Nucleic Acid Res. 19:3749). Thus, all of the reagents are heated to 72° C. before adding the final reagent, usually the polymerase. In wax-mediated "hot start" PCR, a component(s) crucial to polymerase activity is physically separated from the rest of the reaction mixture at low temperature by a wax layer which melts upon heating in the first cycle. (Chou et al. (1992) Nucleic Acids Res. 20:1717; Horton et al. (1994) BioTechniques 16:42). "Hot start" PCR has certain drawbacks; the requirement of reopening of tubes before initiating thermocycling increases crossover contamination and repetitive pipetting makes it tedious in handling a large number of samples. A reagent that could be placed directly in the reaction mixture with all other reaction components and inhibit the polymerase at ambient temperature would be useful to overcome limitations associated with "hot start" PCR. Although this method does increase specificity, thereby reducing side products, the method is inconvenient for dealing with a large number of samples, the reaction mixture can become more easily contaminated, and the method is error-prone.

In the second method, termed "in situ hot start," a reagent that binds and inhibits the polymerase at low temperature, but not at high temperature, (e.g. a neutralizing antibody to Taq polymerase (TaqStart) or an oligonucleotide aptamer) is added to the complete reaction mixture. (Birch et al. (1996) Nature 381:445, Dang and Jayasena (1996) J. Mol. Biol. 264:268; Kellogg et al. (1994) Bio Techniques 16:1134–1137). This antibody inhibits the polymerase activity at ambient temperature, but is inactivated by heat denaturation once the reaction is thermocycled, rendering the polymerase active. The drawback of this approach to reducing side products is that the anti-Taq antibody should be stored at −20° C. until use, which means that detection kits should be packaged and shipped under controlled environment adding to their cost. In addition, a significant amount of antibody (~1 μg of antibody/5 U of Taq polymerase), diluted in a vendor specified buffer, is needed for a single PCR.

The development of high affinity nucleic acid ligands capable of inhibiting the thermostable Taq and Tth polymerases would obviate the need for the "hot start" method and would overcome the limitations associated with the second method. Nucleic acid inhibitors can be developed that are extremely specific and have high affinity. Since nucleic acids are more stable than proteins at ambient temperature, the shipping and packaging problems associated with using antibodies can be overcome. Additionally, nucleic acids, like antibodies can be identified that will lose their affinity for the polymerase at higher temperatures, allowing the polymerase to be activated when desired. The potential for mispriming mediated by nucleic acid based inhibitors themselves functioning as primers (in addition to the specific primers used in the reaction) in PCR can be eliminated by capping their 3' ends.

X-ray crystal structures of several DNA polymerases have indicated that they fold into similar three dimensional structures. (For a review, see Joyce and Steitz (1994) Annu. Rev. Biochem. 63:777). The C-terminal domain responsible for polymerization is organized into three sub-domains representing "palm," "fingers" and "thumb," anatomically analogous to a right hand. Tth polymerase and Taq polymerase are 93% similar and 88% identical at the amino acid sequence level (Abramson (1995) in PCR Strategies (Academic Press, New York). Both are devoid of 3'→5' exonuclease activity, but contain 5'→3' exonuclease activity (Abramson (1995) in *PCR Strategies* (Academic Press, New York); Tindall and Kunkel (1988) Biochemistry 27:6008). Thus, nucleic acid ligand inhibitors might be expected to behave similarly toward both of these enzymes, as well as, other thermostable polymerases. This would make possible the use of a single inhibitor for a number of thermostable enzymes.

RNA sequences are converted to cDNA by reverse transcription before being amplified by PCR. Initially, this was achieved in two steps using two different enzymes: a reverse transcriptase and a thermostable DNA polymerase. Recent studies have shown that certain thermostable DNA polymerases have the ability to reverse transcribe RNA, allowing the use of a single enzyme to amplify RNA amplicons (Myers and Gelfand (1991) Biochemistry 30:7661–7666). Since RNA is labile at high temperature in the presence of divalent ions, reverse transcription is carried out at lower temperature (50–60° C.) than DNA synthesis. Therefore, it would be desirable to have a reagent that the reagent that is used to inhibit the ambient activity of the polymerase should reactivate the polymerase at lower temperature. This requirement eliminates the use of an antibody that demands high temperatures (70–90° C.) for inactivation to generate in situ hot start conditions in RNA-based amplifications.

SELEX™

A method for the in vitro evolution of nucleic acid molecules with highly specific binding to target molecules has been developed. This method, Systematic Evolution of Ligands by EXponential enrichment, termed SELEX™, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Methods for Identifying Nucleic Acid Ligands," now U.S. Pat. No. 5,270,163 (see also WO 91/19813, published Dec. 26, 1991), each of which is herein specifically incorporated by reference in its entirety. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (See U.S. patent application Ser. No. 08/198,670, filed Feb. 22, 1994, entitled "Method for Selecting Nucleic Acids on the Basis of Structure," now U.S. Pat. No. 5,707,796) describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned (See U.S. patent application Ser. No. 08/612,895, filed Mar. 8, 1996, entitled "Systematic Evolution of Ligands by Exponential Enrichment: Photoselection of Nucleic Acid Ligands and Solution SELEX," now U.S. Pat. No. 5,736,177), describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957, filed May 18, 1995, entitled "High-Affinity Nucleic Acid Ligands That Discriminate Between Theophylline and Caffeine," now U.S. Pat. No. 5,580,737), describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," abandoned in favor of U.S. application Ser. No. 08/461,069, filed May 5, 1995, entitled "Systematic Evolution of Ligands by EXponential Enrichment: Solution SELEX," now U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now U.S. Pat. No. 4,496,938, describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. application Ser. No. 08/430,709, filed Apr. 27, 1995, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" now U.S. Pat. No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing nucleic acid ligands to DNA polymerases. Specifically included are methods for identifying nucleic acid ligands to thermostable DNA polymerases useful in the Polymerase Chain Reaction, including the Taq, Tth and TZ05 polymerases and the nucleic acid ligands so identified and produced. More particularly, DNA sequences are provided that are capable of binding specifically to the Taq, Tth and TZ05 polymerases respectively, thereby inhibiting their ability to catalyze the synthesis of DNA. Using the method of this invention nucleic acid ligands are selected in vitro under the conditions defined by the user, and hence, provide the opportunity to select ligands that bind and inhibit a polymerase at/or near a predetermined temperature. DNA sequences are provided that bind and inhibit Taq and Tth polymerase at ambient temperatures and that bind and inhibit Taq and TZ05 polymerase near 55° C. The method of this invention can be extended to identifying and producing nucleic acid ligands to any thermostable DNA polymerase up to any predetermined temperature and the ligands so identified and produced.

Further included in this invention is a method of identifying nucleic acid ligands and nucleic acid ligand sequences to the Taq, Tth and TZ05 polymerases comprising the steps of (a) preparing a candidate mixture of nucleic acids, (b) partitioning between members of said candidate mixture on the basis of affinity to the Taq, Tth and TZ05 polymerases at a predetermined temperature and (c) amplifying the selected molecules to yield a mixture of nucleic acids enriched for nucleic acid sequences with a relatively higher affinity for binding to the Taq, Tth and TZ05 polymerases, respectively.

Further included in this invention is an improved method of performing the Polymerase Chain Reaction comprising the step of including a nucleic acid ligand that inhibits the thermostable polymerase at ambient temperatures, but dissociates from the polymerase at elevated temperatures. Such nucleic acid ligands are identified according to the method of this invention.

More specifically, the present invention includes the ssDNA ligands to Taq polymerase, Tth polymerase and TZ05 polymerase identified according to the above-described method, including those ligands listed in Tables 2–5, 10 and 11 (SEQ ID NOS:7–74) and Tables 4–6 and FIG. 33 (SEQ ID NOS:78–115). Also included are DNA ligands to Taq polymerase, Tth polymerase TZ05 polymerase that are substantially homologous to any of the given ligands and that have substantially the same ability to bind and inhibit the activity of Taq polymerase, Tth polymerase and TZ05 polymerase. Further included in this invention are DNA ligands to Taq polymerase, Tth polymerase and TZ05 polymerase that have substantially the same structural form as the ligands presented herein and that have substantially the same ability to bind and inhibit the activity of Taq polymerase, Tth polymerase and TZ05 polymerase.

The present invention also includes modified nucleotide sequences based on the DNA ligands identified herein and mixtures of the same.

The nucleic acid ligands of the present invention may function as "switches" in that they turn the Polymerase Chain Reaction "on" or "off" depending on the temperature of the reaction mixture. The present invention, therefore, also includes a method for identifying and preparing nucleic acid ligand sequences which function as switches comprising the steps of (a) preparing a candidate mixture of nucleic acids, (b) partitioning between members of said candidate mixture on the basis of affinity to the Taq, Tth or TZ05 polymerases and (c) amplifying the selected molecules using the target molecule to yield a mixture of nucleic acids enriched for nucleic acid sequences with a relatively higher affinity for binding to the Taq, Tth and TZ05 polymerases only at temperatures below the temperature of amplification, respectively.

The present invention, therefore, includes methods for identification of nucleic acid switches. Nucleic acids switches are nucleic acids identified by the SELEX process wherein the desired property of the nucleic acid can be "switched" on or off depending on the manipulation of some environmental parameter. Nucleic acid switches may be identified by manipulating the SELEX partitioning step to select for nucleic acids that give opposite results—often binding to the target—based on an alteration in a reaction medium parameter. The examples in this case demonstrate nucleic acid switches that are turned on and off based on temperature, however, the method of this invention can be extended to identifying and preparing nucleic ligands that function as switches on the basis of conditions other than temperature, including but not limited to, pH, concentration of specific ions, ie. $Mg^{++}$.

BRIEF DESCRIPTION OF THE FIGURES

FIGS. 4A–E depict the binding curves of several full-length ligands to Taq polymerase measured at 55° C. FIGS. 4A–D show the interaction of ligands belonging to Family I, whereas FIG. 4E shows the binding of a representative ligand from Family II.

FIGS. 5A–D depict the binding interactions of several full-length ligands to TZ05 polymerase.

FIG. 6 illustrates the hairpin DNA substrate and its product used to assay the polymerase activity.

FIG. 7D shows the activity of Taq polymerase in the presence of the enriched pool that has not been subjected to thermal cycling, whereas FIG. 7E exhibits the activity of Taq polymerase in the presence of the enriched pool that has been thermal cycled before being added to the reaction. Lanes 1–5 indicate the amount of product formed over 5 minute incubations at 20° C., 25° C., 30° C., 35° C. and 40° C., respectively. Lanes 6–10 exhibit Taq polymerase activity in the presence of the enriched pool over 5 minute incubations at 20° C., 25° C., 30° C., 35° C. and 40° C., respectively. The schematics on right depict the starting short end-labeled DNA and the polymerase extended product.

FIG. 23A depicts the effect of the ligands on the activity of Tth polymerase; FIG. 23B depicts the effect of ligands on the activity of Taq polymerase and FIG. 23C depicts the effect of ligands on the activity of the Stoffel Fragment.

FIG. 24A illustrates a comparison of amplification performed under standard conditions (lanes 1–3) with those of "hot start" PCR (lanes 4–6) in detecting the target at 10 and 50 copies. FIG. 24B illustrates a comparison PCR amplifications conducted in the presence of a nonspecific (NS) oligonucleotide (lanes 1–3) with those of TQ21 (lanes 4–6) and TQ30 (lanes 7–9) in detecting the target at ~10 and 50 copies. FIG. 24C illustrates the detection of very low number target copies (as indicated) in the presence of oligonucleotide inhibitors TQ21 and TQ30. In both (B) and (C) oligonucleotide inhibitors were used at a concentration of 50 nM. M indicates molecular weight standards. Arrows in each panel shows the position of the target-specific 203-bp DNA in the gels.

FIG. 31A depicts a binding curve for ligand Trnc.21 to Taq polymerase. FIG. 31 B illustrates the effect of Trnc.21 concentration on the activity of Taq polymerase (●) and Tth polymerase (○). $IC_{50}$ values for Taq polymerase and Tth polymerase are 21 and 36.5 nM, respectively. FIG. 31C depicts the effect of temperature on the inhibition of Taq polymerase (■) and Tth polymerase (○) by Trnc.21. The amount of product formed in the presence of the inhibitor at a given temperature was normalized to that formed in the absence of an inhibitor at the same temperature to obtain the percent product. The calculated $IT_{50}$ values for Taq polymerase and Tth polymerase are 34° C. and 35.6° C., respectively.

FIG. 33 sets forth the sequences of truncates of ligands to TZ05 polymerase. The nucleotide bases that are underlined come from the 5'- and 3'- fixed regions. Asterisks indicate phosphothioate linkages.

FIG. 36 depicts the affinity and inhibition characteristics of the homodimer (D.30–D.30) (SEQ ID NO:71).

FIG. 37 depicts the inhibition characteristics of the heterodimer D.21–D.30 (SEQ ID NO:72).

FIG. 39A depicts the nitrocellulose filter binding analysis of the three dimers and the monomer to TZ05 polymerase and FIG. 39B depicts the analysis of the inhibition of the polymerase activity of TZ05 by the three dimers and the monomer as a function of the reaction temperature.

FIG. 40 illustrates the effect of dNTPs and the hairpin template DNA on the binding affinity of Trnc.21 to Taq polymerase.

DETAILED DESCRIPTION OF THE INVENTION

Figure 1A:
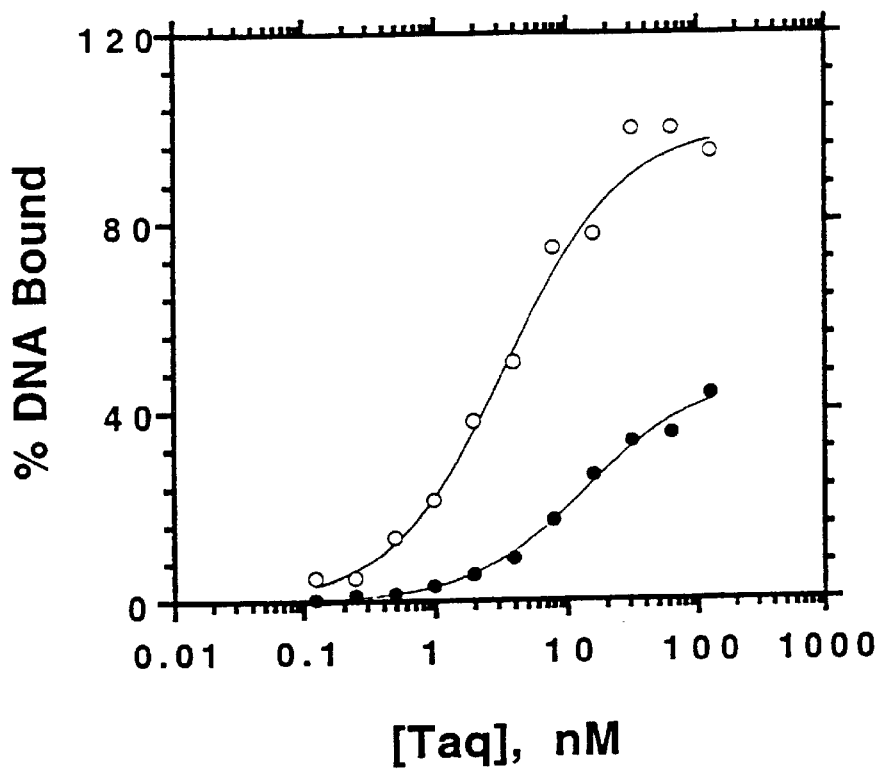
FIG. 1A shows the binding affinities of enriched pools of DNA after 12 rounds of SELEX (○) and the unselected random pool (●) of DNA for the Taq polymerase.

This application describes the isolation of nucleic acid ligands to DNA polymerases. Specifically, this application describes the isolation of nucleic acid ligands to thermostable polymerases useful in the Polymerase Chain Reaction. In a preferred embodiment the DNA polymerase is selected from Taq, Tth or TZ05 polymerase, however the method of this invention can be extended to the identification and purification of high-affinity nucleic acid ligands to any thermostable DNA polymerase. The nucleic acid ligands are identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096 and U.S. patent application Ser. No. 07/931,473, filed Aug. 17, 1992, entitled Methods for Identifying Nucleic Acid Ligands, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The SELEX process provides high affinity ligands of a target molecule. This represents a singular achievement that is unprecedented in the field of nucleic acids research. The present invention applies the SELEX procedure to the specific targets of nucleic acid inhibitors of DNA polymerases, particularly the Taq polymerase, Tth polymerase and TZ05 polymerase. In the example section below, the experimental parameters used to isolate and identify the nucleic acid inhibitors to the Taq, Tth and TZ05 polymerases are described.

In co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled Nucleic Acid Ligands to HIV-RT and HIV-I Rev, is specifically incorporated herein by reference.

Certain terms used to describe the invention herein are defined as follows:

"Nucleic Acid Ligand" as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action has specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to the Taq, Tth and TZ05 polymerases.

The SELEX methodology is described in the SELEX Patent Applications.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is a DNA polymerase. In a preferred embodiment the DNA polymerase is Taq polymerase, Tth polymerase and TZ05 polymerase.

A "Labile ligand" as used herein is a nucleic acid ligand identified by the SELEX process that has a greatly decreased affinity for its target based on an adjustment of an environmental parameter. In the preferred embodiment, the environmental parameter is temperature, and the affinity of a ligand to its target is decreased at elevated temperatures.

"DNA Polymerase" as used herein refers to any enzyme which catalyzes DNA synthesis by addition of deoxyribonucleotide units to a DNA chain using DNA or RNA (reverse transcriptase) as a template. Thermostable DNA polymerases are isolated from microorganisms which thrive in temperatures greater than 40° C.

A "Switch" refers to any compound which functions to turn a reaction "on" or "off" depending upon some specific reaction condition(s). In the present invention the nucleic acid ligands function to turn the PCR "on" or "off" depending upon the temperature of the reaction. A switch can operate on the basis of other reaction conditions including pH, ionic strength or the presence or absence of specific ions. Nucleic acid switches are identified via the SELEX method by the appropriate selection of partitioning techniques. Partitioning parameters are determined in order that nucleic acids are selected that have the desired switching characteristics.

In the present invention, a SELEX experiment was performed in order to identify nucleic acid ligands with specific high affinity for the Taq and Tth polymerases from a degenerate library containing 30 random positions (30N) (Example 1). Although RNA or DNA ligands could be identified for this purpose, the examples below describe the identification of DNA ligands. This SELEX experiment was designed to identify oligonucleotides that bind and inhibit the polymerases at low temperature (room temperature), but not at higher temperatures (>40° C.). This was accomplished using the target polymerase to amplify affinity-selected molecules in PCR at an elevated temperature. Under such conditions, DNA sequences that inhibit the Taq and Tth polymerases at high temperature were not expected to amplify and propagate during selection. This invention includes the specific ssDNA ligands to Tth polymerase shown in Table 2 (SEQ ID NOS:7–35) and Taq polymerase shown in Table 3 (SEQ ID NOS:36–66, 76, 77) and the nucleic acid ligands shown in Tables 10 and 11 (SEQ ID NOS:67–74), identified by the methods described in Example 1. This invention further includes DNA ligands to Taq and Tth polymerase that inhibit the function of Taq and Tth polymerase.

In the present invention, a high temperature SELEX experiment was also performed in order to identify nucleic acid ligands with specific high affinity for the Taq and TZ05 polymerases from a degenerate library containing 30 random positions (30N) (Example 1). This SELEX experiment was designed to identify oligonucleotides that bind and inhibit the polymerases at approximately 55° C. This invention includes the specific ssDNA ligands to Taq polymerase shown in Tables 4 and 5 (SEQ ID NOS:78–88) and TZ05 polymerase shown in Table 6 (SEQ ID NOS:89–106) and FIG. 33 (SEQ ID NOS:107–115), identified by the methods described in Example 1. This invention further includes DNA ligands to Taq and TZ05 polymerase that inhibit the function of Taq and TZ05 polymerase.

The scope of the ligands covered by this invention extends to all nucleic acid ligands of the Taq, Tth and TZ05 polymerases, modified and unmodified, identified according to the SELEX procedure using both low temperature and high temperature affinity selection. More specifically, this invention includes nucleic acid sequences that are substantially homologous to the ligands shown in Tables 2–6, 10 and 11 and FIG. 33. By substantially homologous it is meant a degree of primary sequence homology in excess of 70%, most preferably in excess of 80%. A review of the sequence homologies of the ligands of Taq, Tth and TZ05 shown in Tables 2–6, 10 and 11 and FIG. 33 shows that sequences with little or no primary homology may have substantially the same ability to bind Taq, Tth and TZ05 polymerase, respectively. For this reason, this invention also includes nucleic acid ligands that have substantially the same ability to bind the Taq, Tth and TZ05 polymerases as the nucleic acid ligands shown in Tables 2–6, 10 and 11 and FIG. 33. Substantially the same ability to bind Taq, Tth and TZ05 polymerase means that the affinity is within a few orders of magnitude of the affinity of the ligands described herein. It is well within the skill of those of ordinary skill in the art to determine whether a given sequence—substantially homologous to those specifically described herein—has substantially the same ability to bind Taq, Tth and TZ05 polymerase, respectively.

This invention also includes the ligands as described above, wherein said ligands inhibit the function of other thermostable DNA polymerases, including, but not limited to, the Stoffel fragment, Tbr polymerase (isolated from *Thermus brockianus*), Tfl polymerase (isolated from *Thermus flavus*) and M-MLV reverse transcriptase (isolated from moloney murine leukemia virus).

This invention also includes the ligands as described above, wherein certain chemical modifications are made in order to increase the in vivo or in vitro stability of the ligand or to enhance or mediate the binding or other desirable characteristics of the ligand or the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, which is specifically incorporated herein by reference. Other modifications are known to one of ordinary skill in the art. Such modifications may be made post-SELEX (modification of previously identified unmodified ligands) or by incorporation into the SELEX process.

The nucleic acid ligands to the Taq, Tth and TZ05 polymerases described herein are useful as reagents in the Polymerase Chain Reaction.

The present invention includes an improved method for performing the Polymerase Chain Reaction, wherein a sample containing a nucleic acid sequence that is to be amplified is mixed with 1) primers that are complementary to sequences that flank the sequence to be amplified, 2) a thermostable polymerase, and 3) a nucleic acid ligand that is capable of inhibiting the polymerase at ambient temperatures. The nucleic acid ligand inhibitor may be immobilized on a solid support. The normal steps of PCR are then followed—melting, annealing and synthesis—by thermal cycling of the mixture. The presence of the nucleic acid ligand prevents the mixture from amplifying background DNA by preventing any synthesis at lowered temperatures prior to or during cycling. The present invention also includes a PCR kit comprising a thermostable DNA polymerase and a nucleic acid ligand that inhibits said polymerase at ambient temperatures, yet allows synthesis to occur during the elevated temperature cycles of the PCR process. The present invention also includes a method for improving PCR, as understood by those skilled in the art, including the step of adding to the thermostable polymerase a nucleic acid ligand that inhibits said polymerase at ambient temperatures yet allows synthesis to occur during the elevated temperature cycles of the PCR process.

Nucleic Acid Ligands to Taq, Tth and TZ05 Polymerase

Example 1 describes the experimental procedures used in the selection of nucleic acid ligands to both the Taq and Tth polymerases at room temperature and Taq and TZ05 polymerases at elevated temperatures. The ss-DNA sequences obtained from 10 rounds of selection performed with Tth polymerase at room temperature are set forth in Table 2. Twenty nine individual clones were sequenced from the Tth polymerase selection (only the variable 30 nucleotide region is shown in Table 2). The ligands were grouped into families based upon primary sequence homology.

The ss-DNA sequences obtained from 12 rounds of selection performed with Taq polymerase at room temperature are set forth in Table 3. Of forty two sequences analyzed from the Taq polymerase selection, thirty three were unique. The upper case letters depict the 30-nucleotide random region that is flanked by the 5'-ttctcggttggtctctggcggagc- and -tcttgtgtatgattcgcttttccc-3' fixed sequence regions to form full-length sequences. The lowercase letters in some of the sequences depict the 5'-fixed sequence. The number of clones carrying the same sequence is indicated in parenthesis. The sequences were grouped into three families based on sequence similarity. Conserved sequence motifs in Families I and II are boxed. Both families contained a different consensus sequence: 5'-A$_{/G}$A$_{/G}$TGT G$_{/A}$CAGTAT$_{/G}$C-3' for Family I and 5'-A$_{/G}$CGTTTTG-3' for Family II. In Family I, the 5' and the 3' regions of the consensus sequence showed potential for base pairing with each other (underlined in Table 3). Additionally, the covariation observed in these regions suggests the existence of a possible stem loop structure. In most of the ligands the potential base pairing regions extend beyond the consensus region. In contrast, Family II ligands do not have an obvious secondary structural motif.

Figure 3A:
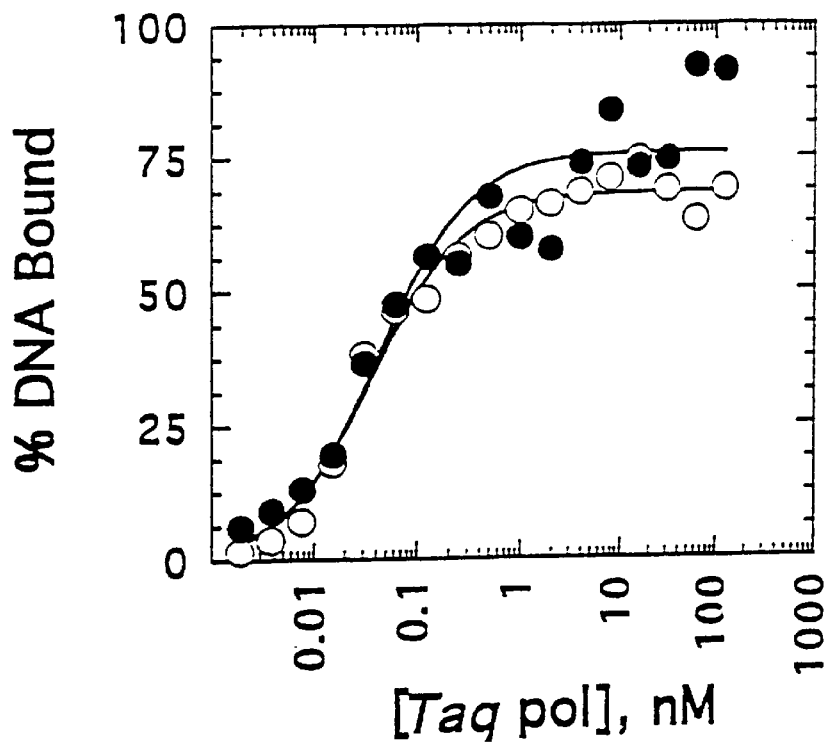
FIG. 3A depicts a binding curve for ligand 30 (TQ30 SEQ ID NO:50) (●) and ligand 21 (TQ21 (SEQ ID NO:59) (○) to Taq polymerase.
Figure 3B:
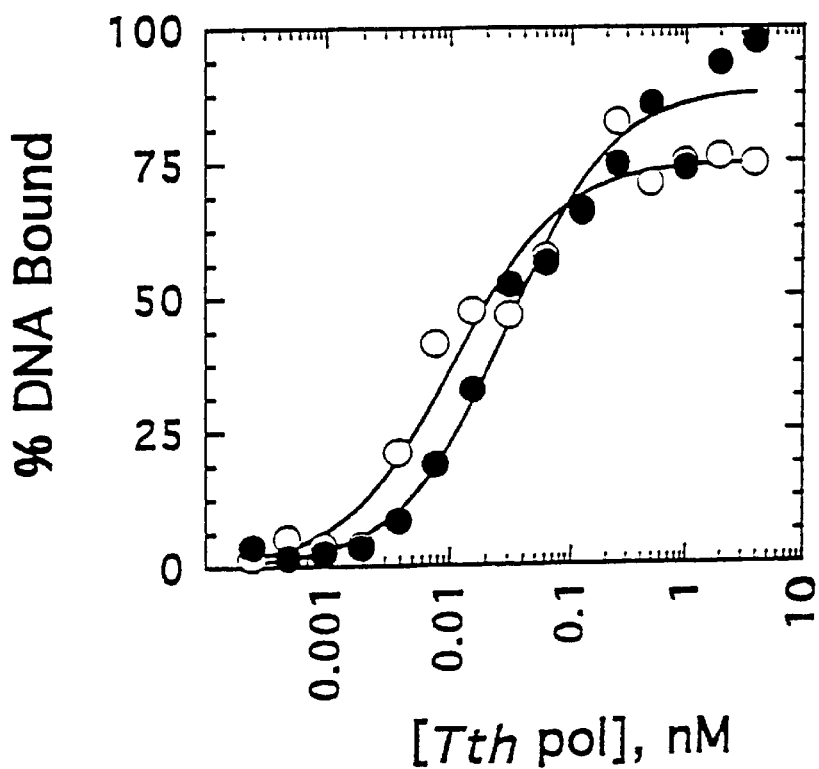
FIG. 3B depicts a binding curve for ligand 30 (●) and ligand 21 (○) to Tth polymerase.

Representative binding curves obtained by nitrocellulose filter binding at room temperature for clone 30 (TQ30 (SEQ ID NO:50)) from Family I and clone 21 (TQ21 (SEQ ID NO:59)) from Family II, are shown in FIG. 3. In both cases, the ligands show tight binding to the two polymerases, with $K_d$ values in the low picomolar range; $K_d$ values of TQ30 are 40±1 pM for Taq polymerase and 28±4 pM for Tth polymerase, whereas those of TQ21 are 36±4 pM and 10±2 pM for Taq polymerase and Tth polymerase, respectively.

Several more ligands from the two families were screened. $K_d$ values ranged from 0.04 to 9 nM for Taq polymerase and from 0.01 to 0.3 nM for Tth polymerase.

Binding interactions of individual sequences with Taq polymerase was measured by nitrocellulose filter binding at 55° C. Several representative binding curves are shown in FIG. 4A–E. FIGS. 4A–D shows binding curves of four sequences belonging to Family I (see Tables 4 and 5). Clones 6 (SEQ ID NO:78), 22 (SEQ ID NO:81) and 28 (SEQ ID NO:87) all show high-affinity binding to Taq polymerase at 55° C. as characterized by their $K_d$ values in the low picomolar range. Clone 18 (SEQ ID NO:83), however, containing the consensus sequence identified among others in the family does not show high affinity. Clone 18 is four nucleotides shorter in the random region, suggesting that the deleted nucleotides apparently play a significant role in the interaction with the polymerase. Clone 19 (SEQ ID NO:84) fell into Family II and does not have the consensus sequence identified in Family I sequences. Yet, it shows high-affinity binding (FIG. 4E) similar to most of the Family I sequences, indicating that there is another sequence solution for high-affinity binding, other than the one found in Family I sequences.

The binding analysis shown in FIGS. 4A–E were performed in the Tris buffer at 55° C. The affinities clones 6, 22 and 28 were compared in the Tris and Tricine buffers at 40° C. and 55° C. (Table 7). In both buffers, the binding affinity of all three clones was higher at 40° C. than at 55° C. Very similar $K_d$ values were observed in both buffers at 40° C., although somewhat reduced affinity was noticed in the Tricine buffer at 55° C.

Binding interactions of individual sequences with TZ05 polymerase were measured by nitrocellulose filter binding at 55° C. as described in Example 2. FIGS. 5A–D show representative binding curves of four different sequences clones 1 (TZ1 (SEQ ID NO:94), 13 (TZ13 (SEQ ID NO:89), 36 (TZ36 (SEQ ID NO:99) and 2 (TZ2 (SEQ ID NO:96). (Table 6). The $K_d$ and $IT_{50}$ values of individual clones are summarized in Table 8. The $IT_{50}$ values were obtained using hairpin extension assays as described in Example 2. Most of ligands show high-affinity binding to TZ05 polymerase at 55° C., as characterized by their $K_d$ values in low picomolar range. The TZ2 sequence carrying 26 nucleotides in its random region (four nucleotides shorter than expected) did not effectively interact with the polymerase at 55° C. (FIG. 5D and Table 8), suggesting that deleted nucleotides are required for high-affinity binding.

Polymerase Inhibition Assays

Example 2 (FIGS. 7–10) describes a number of polymerase inhibition assays, which demonstrate that the ligands of the invention identified using low temperature affinity selection are capable of inhibiting the interaction of both the Taq and Tth polymerases, at temperatures less than 40° C. Example 2 (FIGS. 11–15) also describes a number of polymerase inhibition assays, which demonstrate that the ligands of the invention identified using high temperature affinity selection are capable of inhibiting the interaction of both Taq and TZ05 polymerase at temperatures of approximately 55° C. In Example 2, the designed hairpin DNA (DNA-HP;5'-ATGCCTAAGTTTCGAACGCGGCTAGC-CAGCTTTTGCTGGCTAGCC GCGT-3' (SEQ ID NO:6; FIG. 6) is used as a template for measurement of the ability of the enriched pools of DNA, as well as, specific ligands identified according to the method of this invention to inhibit polymerase activity, under a variety of conditions. This assay detects template-directed fill-in synthesis of 15 nucleotides on a fold-back DNA hairpin.

Ligands Selected to Recognize Taq and Tth Polymerase at Low Temperatures

Figure 7A:
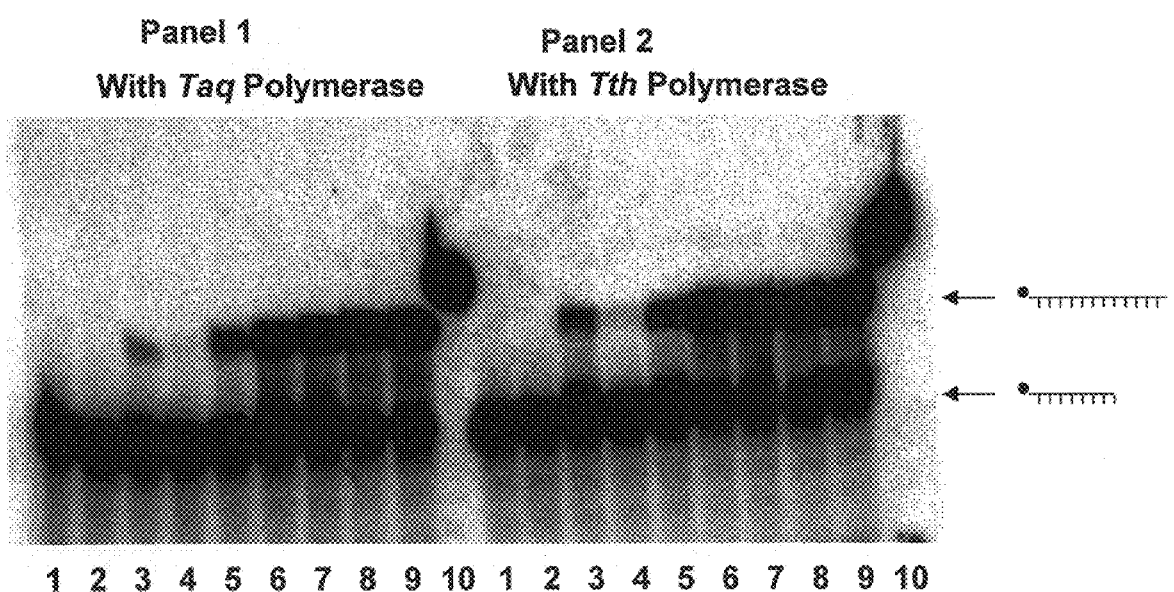
FIG. 7A illustrates a polymerase activity assay for the Taq and Tth polymerases carried out at different temperatures with different times of incubations. The end labeled DNA substrate shown in FIG. 6 is resolved on a 15% polyacrylamide gel under denaturing conditions. The data on Panel 1 were obtained with the Taq polymerase and the enriched pool selected for Taq polymerase, whereas those shown on Panel 2 were obtained with the Tth polymerase and the enriched pool selected for Tth polymerase. The untreated, 5'-end labeled DNA hairpin template (lane 1); the labeled template in a reaction mixture that lacks the polymerase (lane 2); incubation of the complete reaction mixture for 25 minutes at room temperature in the absence of (lane 3) and in the presence of the enriched pool (lane 4). Lanes 5, 6, and 7 show the incubations of complete reaction mixtures in the presence of the enriched pool for 5 minutes at 37° C., 50° C. and 60° C., respectively. Lanes 8 and 9 show the incubations of the complete reaction mixtures in the presence (lane 8) and absence (lane 9) of the enriched pool at 70° C. for 5 minutes. Lane 10 shows the gel mobility of the end-labeled pool DNA. The schematics on the right of the gels depict the positions of the starting short end-labeled DNA and the polymerase extended product.

FIG. 7A shows the results of inhibition assays carried out at different temperatures with different times of incubations using the enriched pools of DNA ligands. The activity of both the Taq and Tth polymerases is generally low at low temperatures and increases as the temperature is increased, as can be seen by comparing lane 3 (room temperature reaction) with lanes 6–9 (reaction at 50, 60 and 70° C., respectively). The enriched pools inhibit the activity of their respective polymerases at room temperature (lane 4), but not at 50° C.–70° C. Lane 10 shows the mobility of the radiolabeled pool as a reference to detect the possible extension of DNA molecules in the pool that can serve as a template for the polymerases. The lack of radiolabeled bands migrating closer or above the labeled pool in lanes 6–9 indicates the absence of polymerization of the ssDNA pool.

Figure 7B:
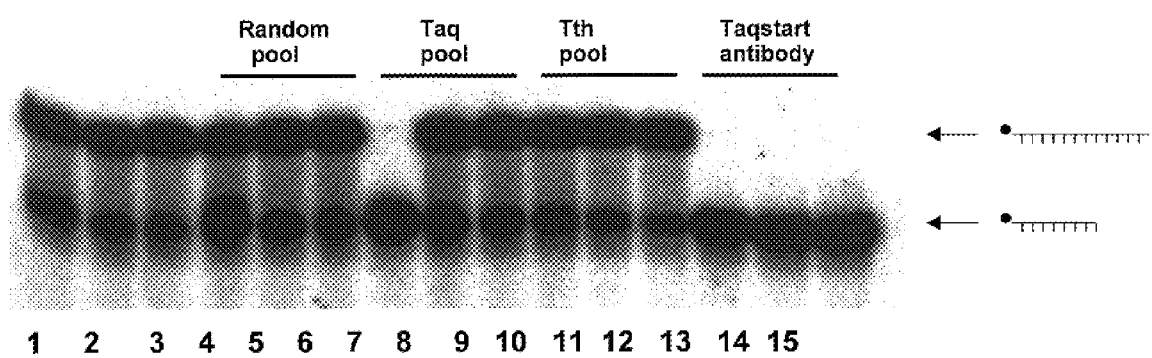
FIGS. 7B and 7C illustrate a second polymerase activity assay for the Taq and Tth polymerases, performed at three different temperatures. The DNA is resolved on a 15% polyacrylamide gel under denaturing conditions. The data in FIG. 7B were obtained with the Taq polymerase and the data in FIG. 7C were obtained with the Tth polymerase. Lanes 1–3 show the products obtained in the absence of any inhibitor upon incubation at room temperature, 30° C. and 37° C., respectively, for 5 minutes. Lanes 4–6 show the data obtained with the unselected random sequence pool; lanes 7–9 with the enriched pool for Taq polymerase; lanes 10–12 with the enriched pool for Tth polymerase; lanes 13–15 with Taqstart antibody for 5 minute incubations at the three temperatures indicated. The schematics on the right indicate the starting short end-labeled DNA and the polymerase extended product.
Figure 7C:
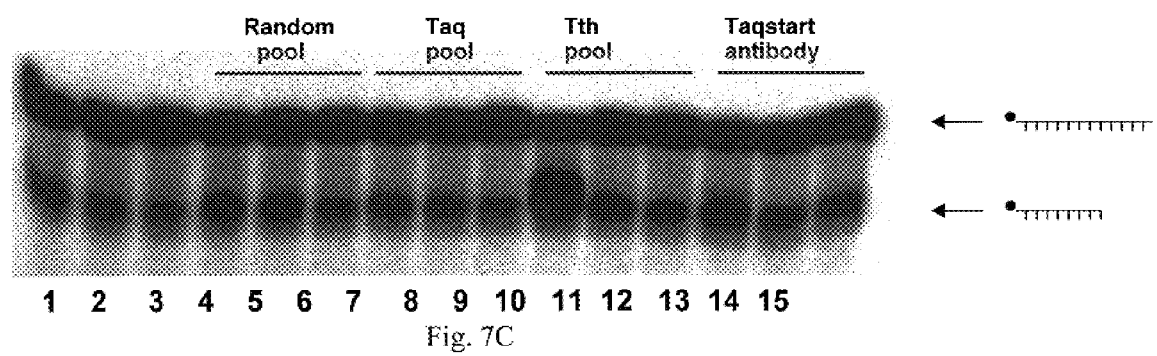

Since the activity of thermostable polymerases is low at ambient temperature, the incubation period in the assay was increased to 16 hours. FIGS. 7B and 7C show the results of 16 hour incubation of the template with the two polymerases in the presence of selected pools and the random pool. In addition, the inhibition mediated by selected pools was compared to that of anti-Taq antibody (Taqstart). The data in FIG. 7B was obtained with the Taq polymerase and the data in FIG. 7C was obtained with the Tth polymerase. Over the three temperatures studied, room temperature, 30° C. and 37° C., the random pool did not show inhibition of the two polymerases (compare lanes 1–3 with 4–6), suggesting that the inhibition caused by the enriched pool is sequence specific. The pool selected for Taq polymerase completely inhibited the polymerase activity over a 16 hour incubation only at room temperature (lane 7), but not at 30° C. and above (lanes 8 and 9). Although the pool selected for Tth polymerase did show binding to Taq polymerase, it was unable to inhibit Taq polymerase (lanes 10–12). As expected, Taqstart antibody inhibited the polymerase activity at all three temperatures investigated (lanes 12–15). The ssDNA pool selected for Tth polymerase, however, did not inhibit the enzyme activity over a 16 hour incubation (compare lanes 1–3 with 4–6). In contrast, the same pool was able to inhibit the enzyme activity over short periods of incubation. The pool selected for Taq polymerase was able to partially inhibit (>50%) the Tth activity over 16 hour incubation at room temperature (lane 10). Taqstart antibody did not have any effect on the activity of Tth (lanes 13–15).

Figures 7D, 7E:
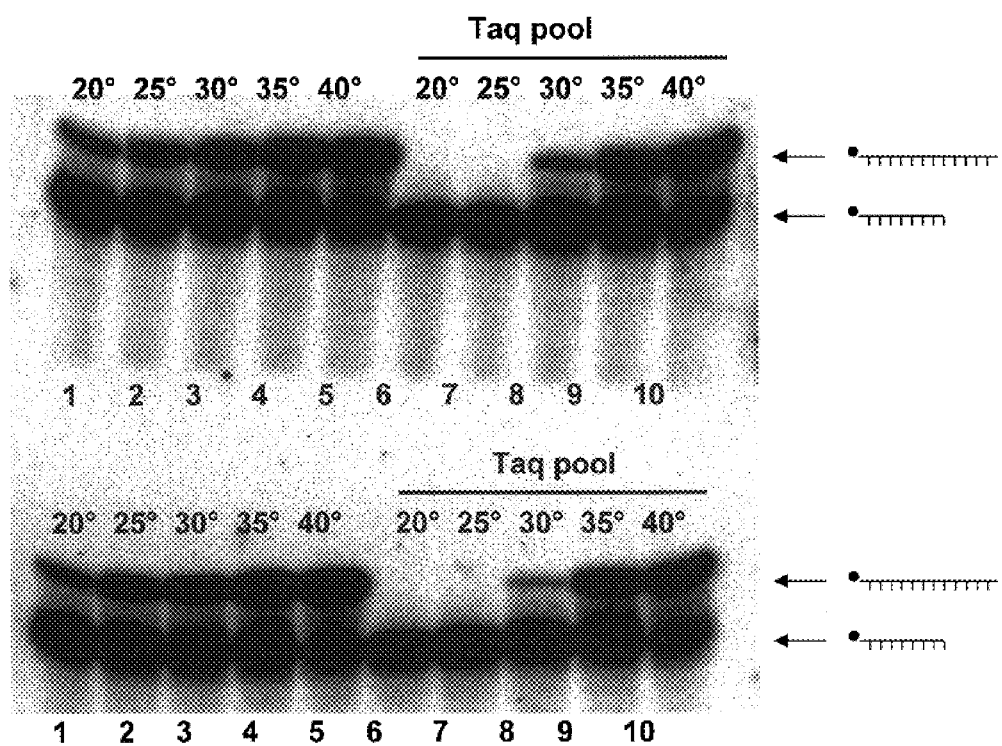
FIGS. 7D and 7E illustrate a reversible inhibition of Taq and Tth polymerases by the enriched pool.
Figure 8A:
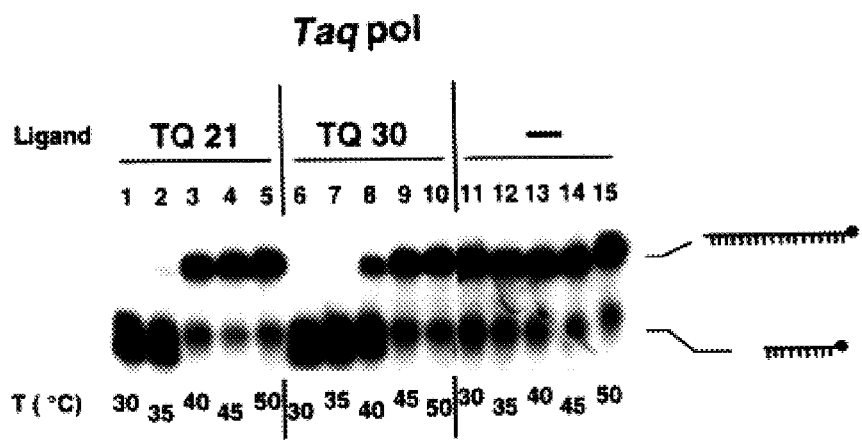
FIG. 8 depicts the effect of temperature on the inhibition of Taq polymerase (FIG. 8A) and Tth polymerase (FIG. 8B) by ligands TQ30 (SEQ ID NO:50) and TQ21 (SEQ ID NO:59) (lanes 1–10). The DNA is resolved on a 10% polyacrylamide gel under denaturing conditions. Lanes 11–15 depict the formation of product in the absence of an inhibitor. The right side of the autoradiograms schematically depict the 5'-labeled template before and after polymerase extension.
FIGS. 8C and 8D show the percent of product formed in the presence of ligand TQ21 (○) and ligand TQ30 (●) using Taq polymerase (FIG. 8C) and Tth polymerase (FIG. 8D), respectively. The amount of product was quantitated by phosphorimager and normalized to the product formed in the absence of an inhibitor at the same temperature to obtain the percent of product (FIGS. 8C and D (abscissa)).
Figure 8B:
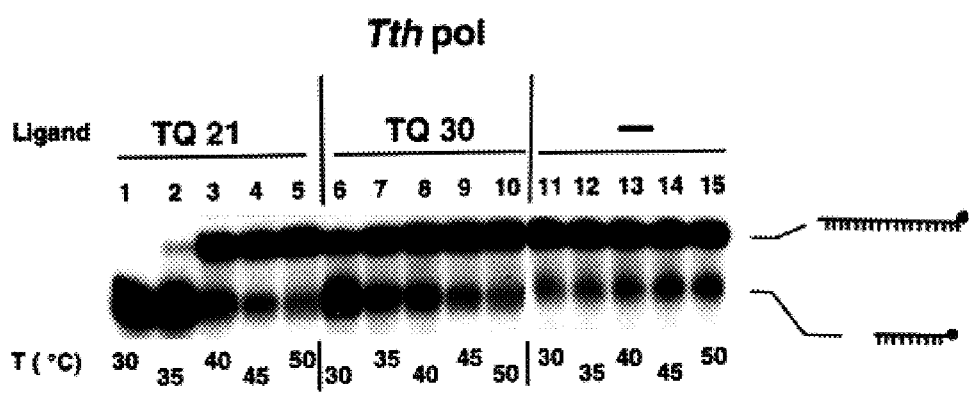
Figure 8C:
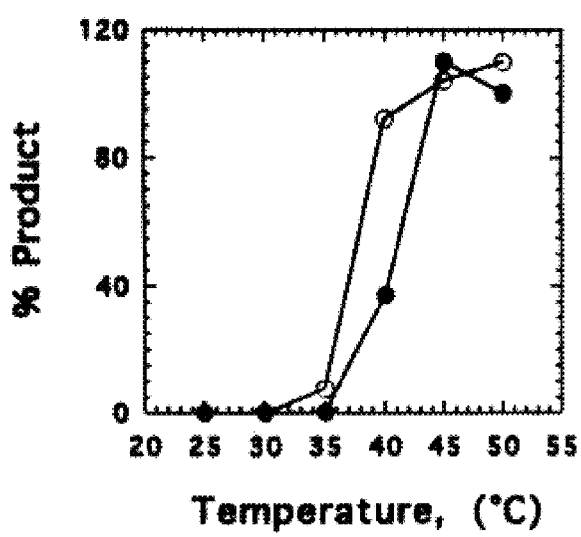
Figure 8D:
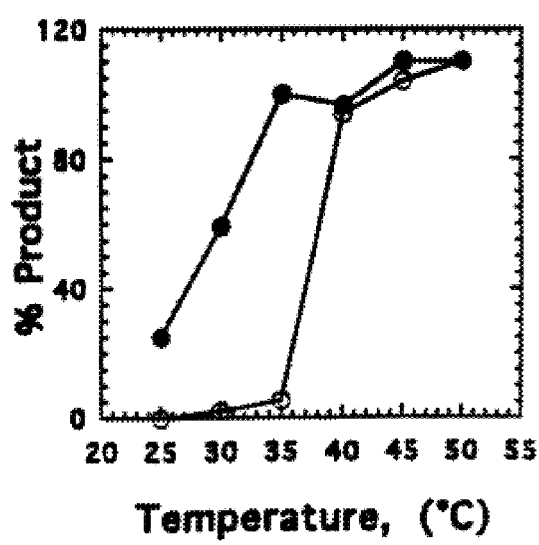

The use of Taqstart antibody is limited to one time in a PCR reaction. Once it is denatured at high temperature it cannot renature back to its native form. Nucleic acid ligands with simple secondary structures, however, have the potential to renature back to their native form after going through a thermal cycle. An experiment was carried out to investigate whether the inhibitory capacity of the DNA pool selected for Taq polymerase can be restored after heating (FIGS. 7D and 7E). FIG. 7D shows the inhibition of Taq activity between 20° C.–40° C. by the selected DNA pool that has not been subjected to thermocycling. Over 45 minutes of incubation, the pool completely inhibits Taq activity at 20° C. and 25° C. Within this relatively short period of incubation, the pool exhibited >70% inhibition at 30° C. A very similar inhibition profile can be seen with the DNA pool that has been subjected to two PCR cycles with the Taq polymerase in the absence of the template DNA.

This result demonstrates that the inhibition mediated by ssDNA is reversibly temperature sensitive and can be restored even after PCR.

FIG. 8 shows the temperature range in which sequences, TQ30 (SEQ ID NO:50) and TQ21 (SEQ ID NO:59) (Table 3), are inhibitory toward the Taq and Tth DNA polymerases. The hairpin extension assays depicted in this figure were performed at the indicated temperatures for 1 hour using 250 nM of the respective ligand (lanes 1–10). As anticipated, the ssDNA ligands did not inhibit either DNA polymerase at temperatures >40° C. (FIGS. 8A and 8B). The temperatures at which 50% of the product is generated during the one-hour assay ($IT_{50}$ values) for ligand TQ30 are 41° C. and 29° C. for Taq polymerase and Tth polymerase, respectively. The respective values for ligand TQ21 are 37° C. and 29° C. (FIGS. 8C and 8D). Binding affinities of the two ligands for these polymerases decrease at higher temperatures (data not shown), in agreement with their decreased inhibitory activity at high temperature. In the hairpin extension assays, approximately 2% of the input hairpin template was not extended by DNA polymerase, presumably due to incorrect folding.

Figure 9A:
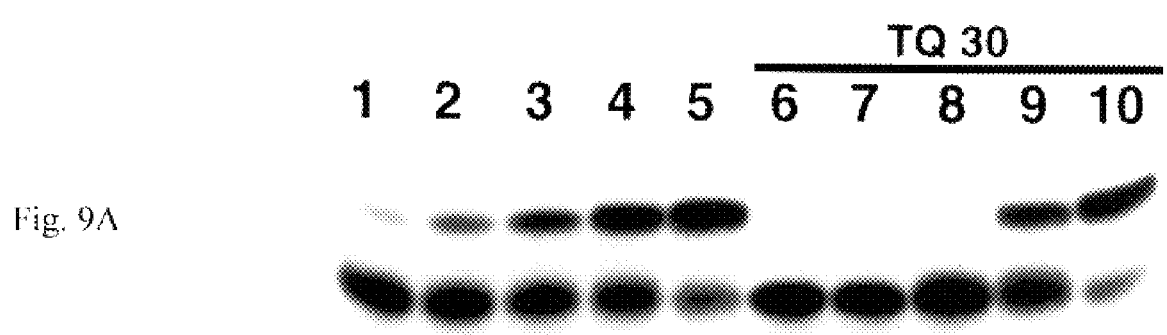
FIGS. 9A and B illustrates the reversible inhibition of Taq polymerase by ligand TQ30 (SEQ ID NO:50). The DNA is resolved on a 10% polyacrylamide gel under denaturing conditions. Lanes 1–5 show the products obtained in the absence of any inhibitor upon incubation between 20° C.–40° C. Lanes 6–10 show the products formed upon incubation between 20° C.–40° C. in the presence of ligand TQ30 that had not been thermocycled (FIG. 9A) and ligand TQ30 that had been subjected to 25 rounds of thermocycling (FIG. 9B).
Figure 9B:
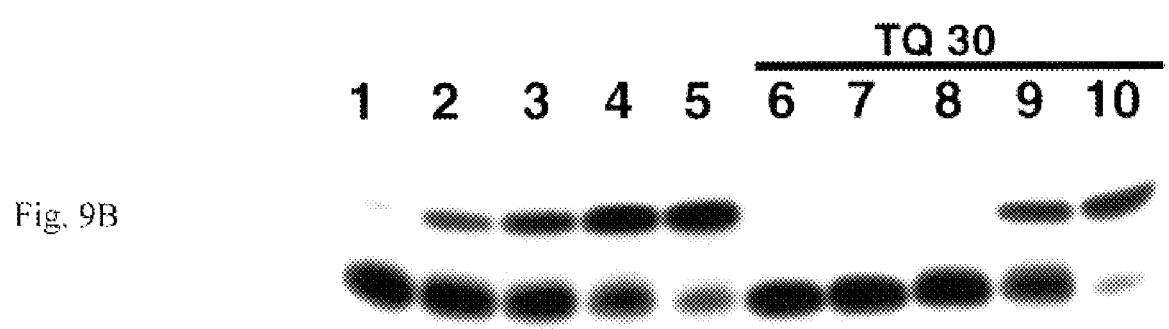

FIG. 9 illustrates that the inhibition of Taq polymerase by ligand TQ30 (SEQ ID NO:50) is thermally reversible and can be restored even after PCR. The hairpin template extension assays depicted in this figure were performed at the indicated temperatures for 10 minutes in a 100 μL reaction volume with 5 U of Taq polymerase, in the absence (lanes 1–5) and in the presence of ligand TQ30 (50 nM) (lanes 6–10). In FIG. 9A, ligand TQ30 had not been subjected to thermocycling. In FIG. 9B, ligand TQ30 was subjected to 25 rounds of thermocycling with Taq polymerase (30 seconds at 90° C.; 1 minute at 50° C., 30 seconds at 72° C.) and cooled to room temperature before adding the radiolabeled hairpin template (250 nM). As can be seen in FIG. 9, in both cases ligand TQ30 inhibited the polymerase at temperatures below 40° C. Additionally, the sample that underwent thermocycling showed identical or more effective inhibition than the sample not subjected to thermocycling.

Figure 10A:
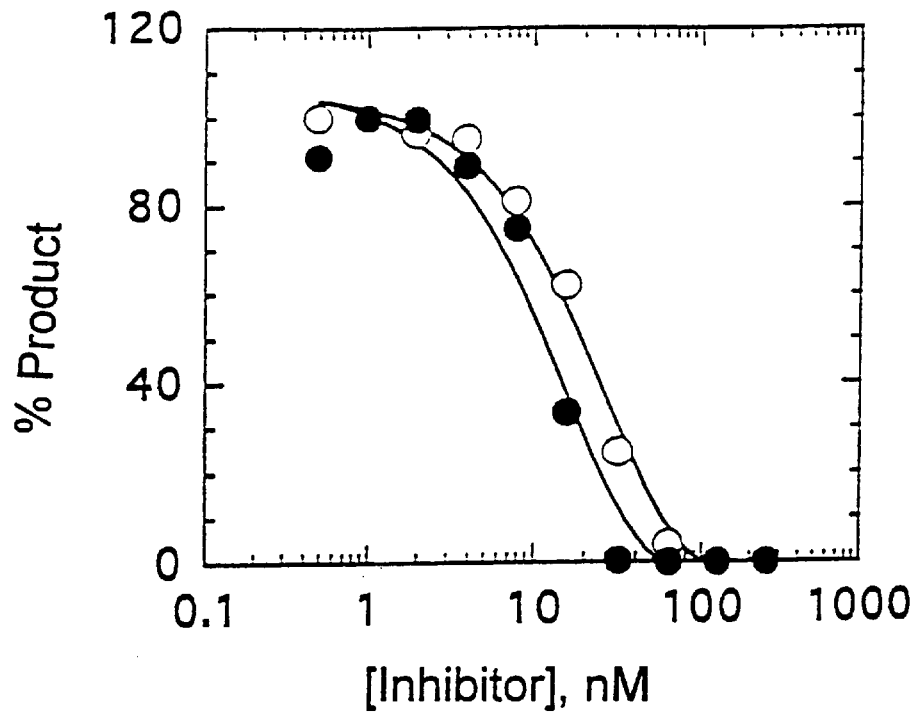
FIGS. 10A and B depict the effect of ligand concentration on the inhibition of Taq polymerase (FIG. 8A) and Tth polymerase (FIG. 8B) by ligands TQ30 (SEQ ID NO:50) (●) and TQ21 (SEQ ID NO:59) (○). The amount of product formed in the presence of varying concentrations of inhibitor in the template extension assays was quantitated by phosphorimager and normalized to the amount of product formed in the absence of an inhibitor to obtain the percent product (abscissa).
Figure 10B:
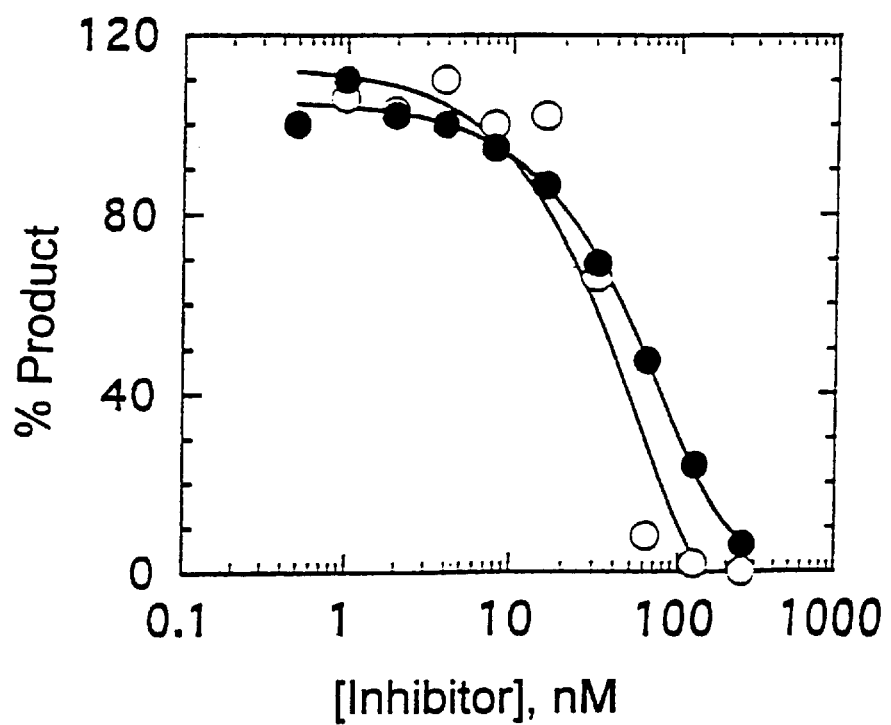

FIG. 10 demonstrates the effect of ligand concentration on the inhibition of the Taq and Tth polymerases. The concentration of inhibitor required to produce 50% of the product in the hairpin assay ($IC_{50}$ values) for TQ30 (SEQ ID NO:50) and TQ21 (SEQ ID NO:59) was 6.5 nM and 10 nM, respectively, for inhibition of Taq polymerase at room temperature (approximately 22° C.) over a 16 hour incubation period (FIG. 10A). Since the concentration of Taq polymerase used in the assay is 12.5 nM, enzyme inhibition by TQ30 (SEQ ID NO:50) is likely to be a result of stoichiometric binding. When assayed at 30° C. over 1 hour, $IC_{50}$ values increased by approximately three fold (22 nM for TQ30 and 67 nM for TQ21; data not shown). The $IC_{50}$ values of TQ30 and TQ21 for the inhibition of Tth polymerase were 60 and 36 nM, respectively, at room temperature (FIG. 10B). Overall, these oligonucleotides are more effective inhibitors for Taq polymerase, the enzyme used in selection, than for Tth polymerase.

To rule out the possibility that the observed inhibition of the extension of the template is due to preferential binding of selected ligands to the polymerase and subsequent utilization as substrates, 5'-end radiolabeled TQ21 and TQ30 ligands were incubated with the two DNA polymerases for 16 hours (Example 2, data not shown). Ligand TQ30 did not show extension products upon incubation with either enzyme, indicating that it is not a substrate for the polymerase activity. TQ21, however, gave a higher molecular weight band indicating sequence extension upon incubating with both polymerases. The observed partial extension of ligand TQ21 was effectively eliminated by blocking the availability of the 3' OH group by capping the 3' end with an ethylene glycol linker using standard conditions. The 3'-capped oligonucleotide constructs are equally effective inhibitors as the uncapped molecules (data not shown). These results indicate that the ssDNA ligands are poor substrates for polymerase activity and that the two types of ligands are likely positioned on DNA polymerases differently; TQ21 binds to the polymerases such that its 3' end can be extended (albeit poorly), whereas TQ30 cannot extended upon binding.

Ligands Selected to Recognize Taq and TZ05 Polymerase at High Temperatures

Figure 11:
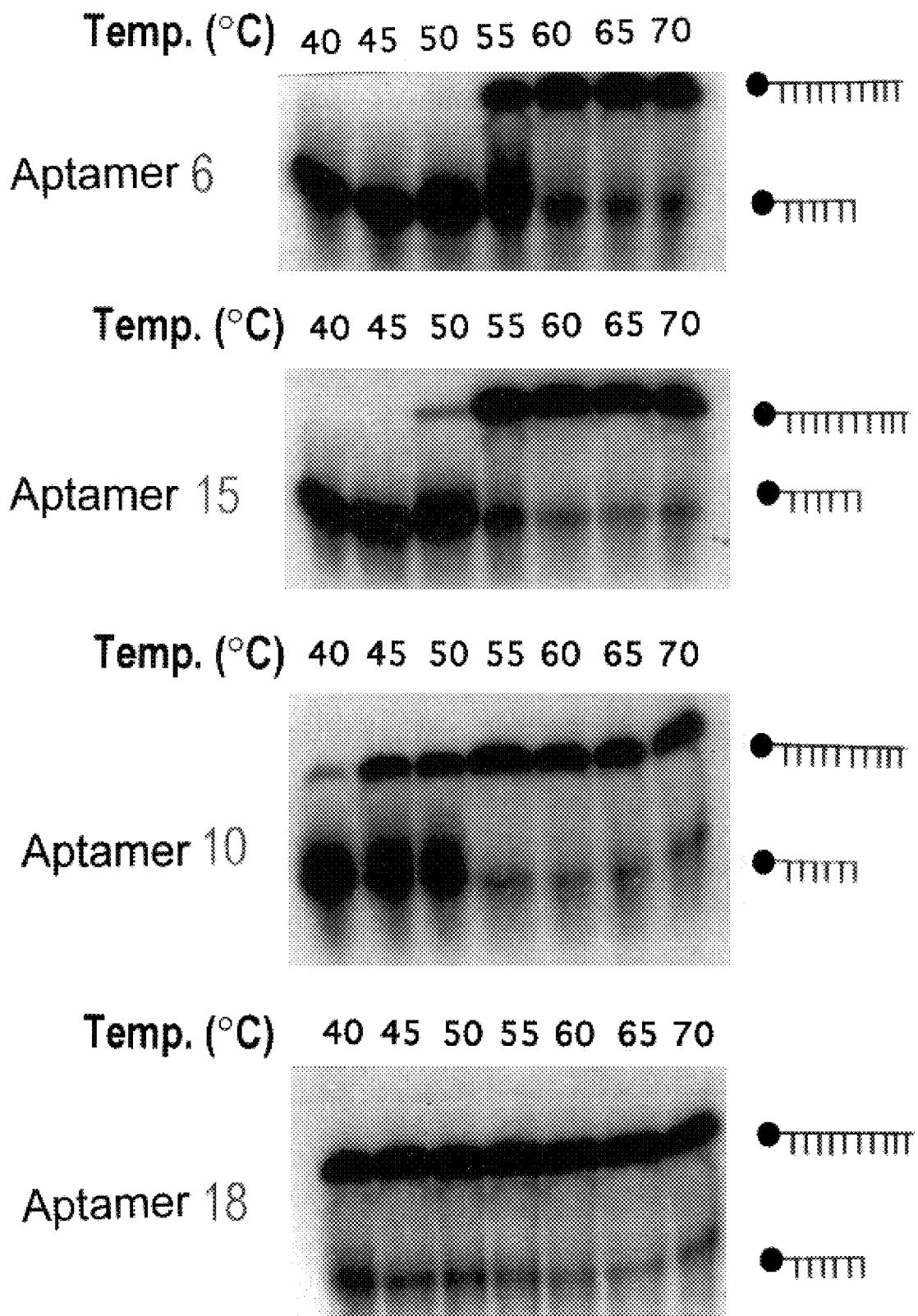
FIG. 11 depicts the effect of temperature on the inhibition of Taq polymerase by ligands 6 (SEQ ID NO:78), 15 (SEQ ID NO:86), 10 (SEQ ID NO:85) and 18 (SEQ ID NO:83). The extension products were analyzed on 10% polyacrylamide gels run under denaturing conditions followed by autoradiography.
Figure 12A:
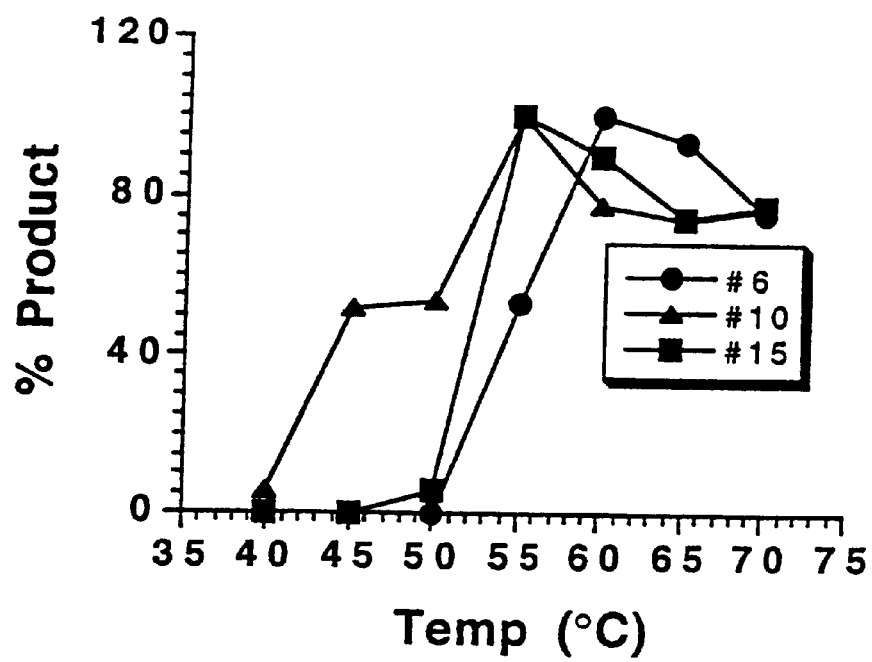
FIGS. 12A and B show the percent of product formed in the presence of ligand 6 (●), ligand 10 (▲) and ligand 15 (■) (Figure DDA) and ligand 18 (●), ligand 19 (▲) and ligand 20 (■) (Figure DDB) using Taq polymerase. The amount of product was quantitated by phosphorimager and normalized to the product formed in the absence of an inhibitor at the same temperature to obtain the percent of product.
Figure 12B:
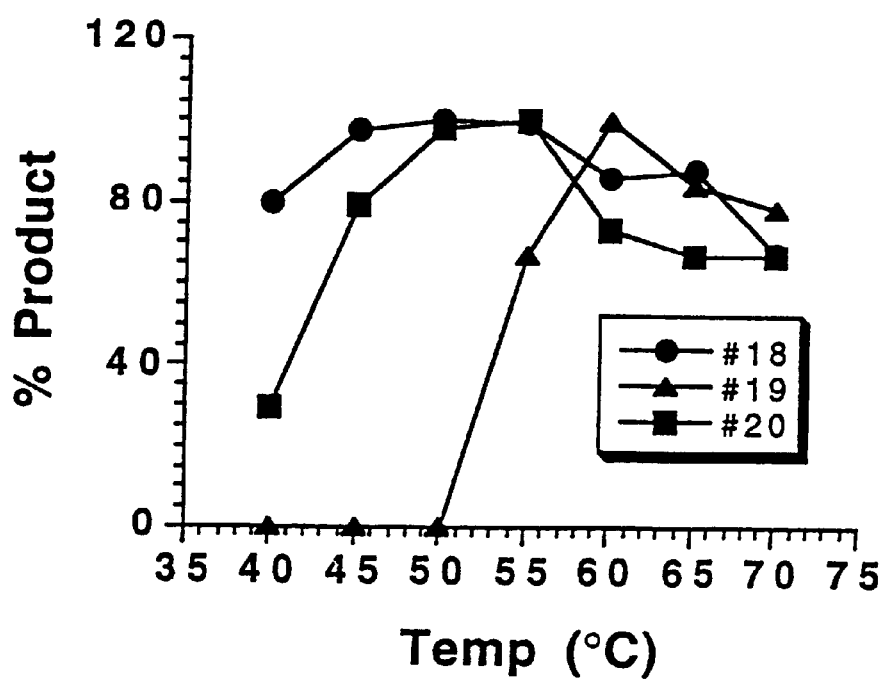
Figure 13A:
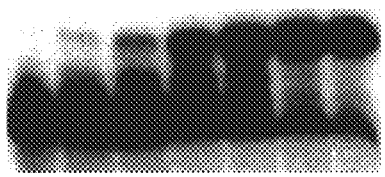
FIGS. 13A–F depict the effect of temperature on the inhibition of TZ05 polymerase by ligands TZ1 (SEQ ID NO:94), TZ2 (SEQ ID NO:96), TZ3 (SEQ ID NO: 106), TZ8 (SEQ ID NO:100), TZ9 (SEQ ID NO:101) and TZ13 (SEQ ID NO:89). The extension products were analyzed by gel electrophoresis under denaturing conditions followed by autoradiography.
Figure 13C:
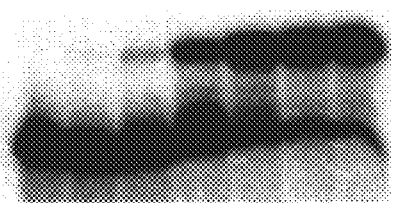
Figure 13E:
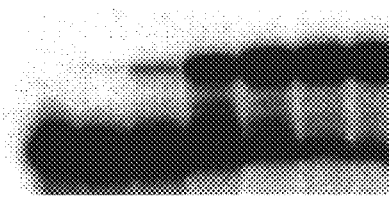
Figure 13B:
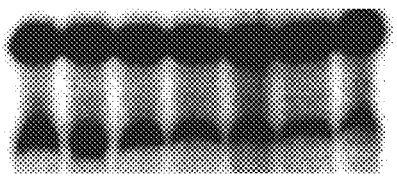
Figure 13D:
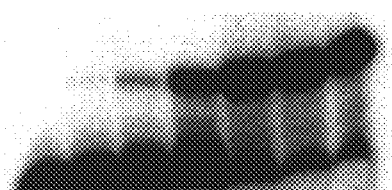
Figure 13F:
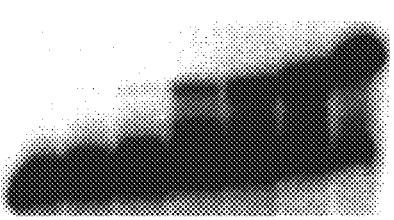

FIG. 11 shows the extension of end-labeled hairpin substrate catalyzed by Taq polymerase over a range of temperatures in the presence of four ligands obtained after affinity selection at high temperature: Clones 6 (SEQ ID NO:78), 15 (SEQ ID NO:86), 10 (SEQ ID NO:85) and 18 (SEQ ID NO:83). Not all four ligands inhibited Taq polymerase to the same degree. Clone 18, which did not show high affinity binding to Taq polymerase, did not show significant inhibition of the enzyme even at 40° C. The potency of polymerase inhibition by these ligands follows the order of their affinities; clone 6>15>10>>>>18. FIGS. 12A and B show the percent of product formed in the presence of these ligands as a function of temperature. The $IT_{50}$ values of these ligands are between 40° C.–56° C., except for ligand 18, which showed a value of <40° C. This result is consistent with its reduced affinity. In accordance with its high-affinity binding, the Family II sequence, clone 19 (SEQ ID NO:84), also showed a high $IT_{50}$ value. Table 9 summarizes $K_d$ values and $IT_{50}$ values for clone 6 (TQH6) and 28 (TQH28). The data in Table 9 clearly demonstrates that the ligands obtained after affinity selection at high temperature possess expected characteristics, namely the binding and inhibition at high temperature. This outcome further reinforces the significance of defining the appropriate selection conditions to obtain ligands with the desired properties.

FIGS. 13A–F show the extension of end-labeled substrate catalyzed by TZ05 polymerase in the presence of various ligands obtained after affinity selection at high temperature over a range of temperatures. The observed high-affinity interaction of ligands with TZ05 polymerase mirror their ability to inhibit the polymerase activity of the enzyme. Except for clone 2 (TZ2 (SEQ ID NO:96)), which did not bind the polymerase with high affinity, the other ligands showed $IT_{50}$ values between 40–59° C. (see Table 8). The TZ2 sequence with shorter random region (four nucleotides shorter than expected) did not effectively inhibit the polymerase even at 35° C. Ligands TZ13 (SEQ ID NO:89) and TZ26 (SEQ ID NO:93), belonging to Family 1, showed two extreme $IT_{50}$ values (58.5° C. vs 41° C.). At the sequence level these two sequences are very similar, however, their inhibitory potency, especially at higher temperature is rather different. Although there is a high degree of sequence similarity between TZ13 and TZ26, the minor differences in the two sequences may account for their difference in the capacity to inhibit the polymerase.

Figure 14:
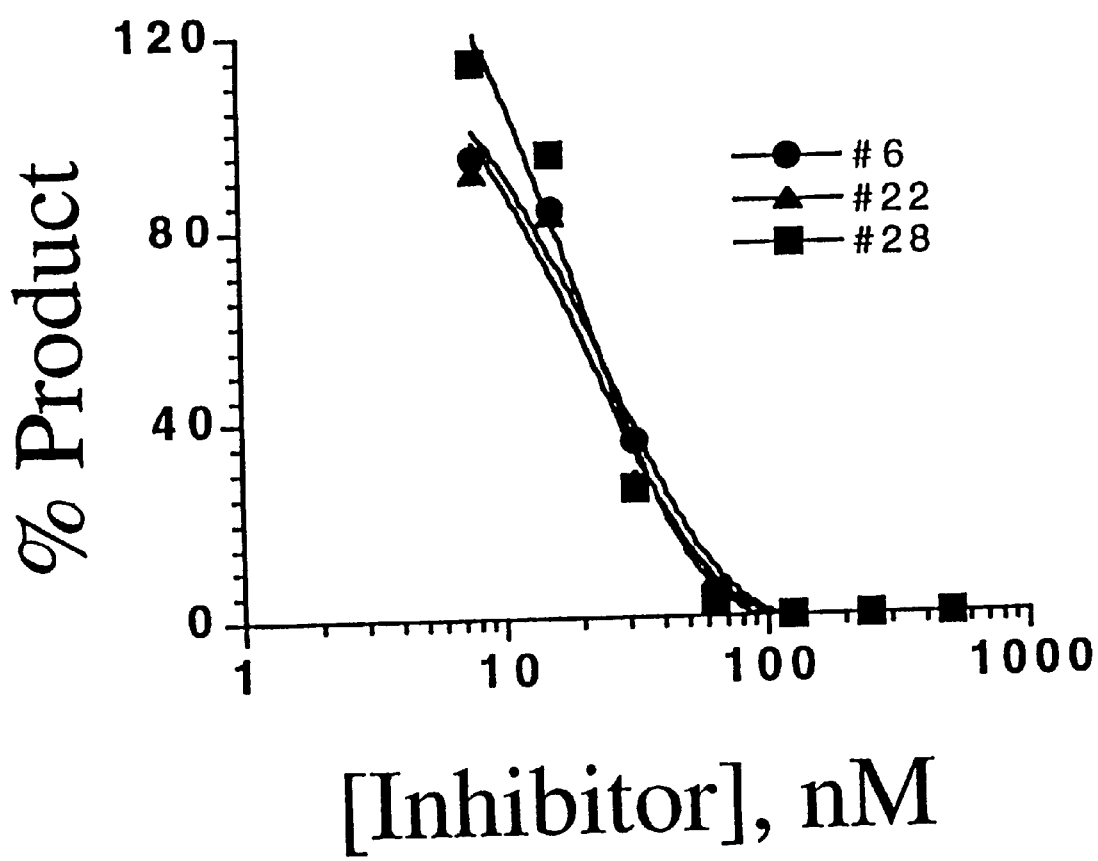
FIG. 14 depicts the effect of ligand concentration on the inhibition of Taq polymerase using various ligands obtained after affinity selection at high temperature (ligand 6 (SEQ ID NO:78) (●), ligand 22 (SEQ ID NO:81) (▲) and ligand 28 (SEQ ID NO:87) (■)). The hairpin extension assay was carried out as described in Example 2. The extension product of the hairpin substrate was quantified by phosphorimager and normalized to the product formed in the absence of an inhibitor to obtain the percent product.

FIG. 14 demonstrates the effect of the concentration of three ligands obtained using high temperature affinity selection on the inhibition of Taq polymerase. The $IC_{50}$ values of the three ligands are approximately 20 nM.

Figure 15A:
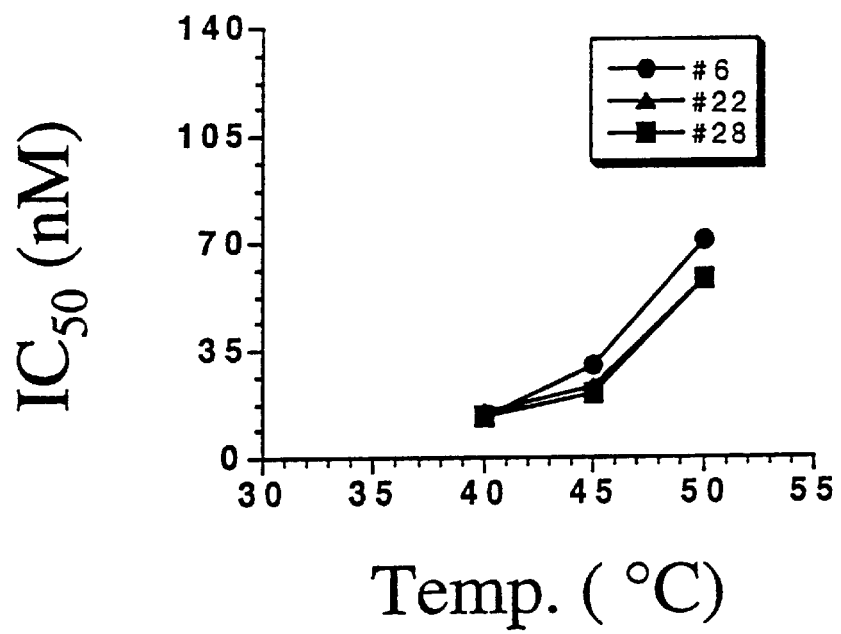
FIGS. 15A and B depict the effect of temperature on the $IC_{50}$ values of ligands 6 (SEQ ID NO:78) (●), 22 (SEQ ID NO:8 1) (▲) and 28 (SEQ ID NO:87) (■) in the Tris buffer (FIG. 15A) and in the Tricine buffer (FIG. 15B).
Figure 15B:
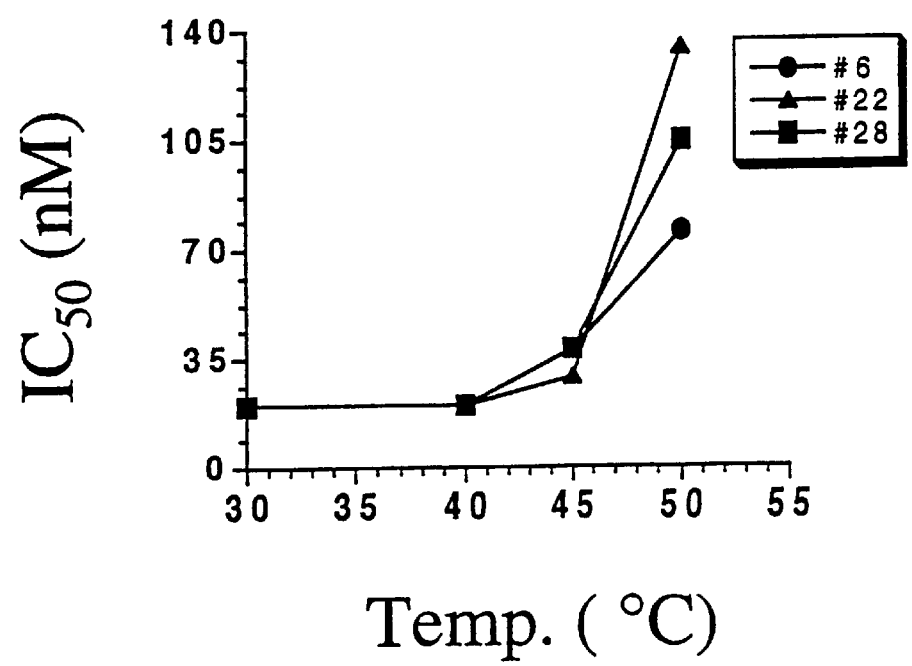

FIG. 15 illustrates the change in $IC_{50}$ values as a function of temperature for ligands 6 (SEQ ID NO:78), 22 (SEQ ID NO:81) and 28 (SEQ ID NO:87) in the Tris buffer (FIG. 15A) and the Tricine buffer (FIG. 15B). In Tris buffer, the $IC_{50}$ values of all three ligands are quite resilient within the temperature range of 40° C. to 50° C. (FIG. 15A). However, in Tricine buffer $IC_{50}$ values are sensitive to temperatures above 45° C. (FIG. 15B). In these assays the concentration of Taq polymerase was 2.5 nM and the $IC_{50}$ values remain 20–40 nM from 30° C. to 45° C. Hence, within this temperature range approximately a 20-fold excess of ligand concentration over the enzyme concentration is sufficient to completely inhibit the enzyme.

Affinity Capture Experiment

The thermal reversibility of the interaction of nucleic acid ligands with the Taq and Tth polymerases raises the possibility of the use of an affinity matrix generated with such ligands, to capture the polymerase after one amplification, for reuse in a subsequent amplification. To investigate the possibility of affinity capture, affinity beads containing ligands TQ30 (SEQ ID NO:50) and TQ21 (SEQ ID NO:59) were prepared as described in Example 1. After extension of the hairpin template with Taq and Tth polymerases in a PCR buffer containing heparin the reaction was mixed with either affinity beads or control beads as described in Example 2, the beads were washed thoroughly and then exposed to a fresh aliquot of reaction mixture containing all of the reagents, except the polymerase. After incubating for an additional 5 minutes at 70° C. to allow the extension on the newly added template, the reaction mixtures were analyzed on an 8% polyacrylamide gel under denaturing conditions. In reaction mixtures that contained the control beads there is no extension of the template in the second round of amplification. In contrast, there is no difference in the extension products in both first and the second rounds of amplification in the reaction mixtures that contained affinity beads, indicating that the affinity beads containing both, ligand TQ30 and TQ21, successfully captured the two polymerases after the first round of PCR.

Effect of Nucleic Acid Ligands on the Exonuclease Activity of the Polymerases

Figure 16:
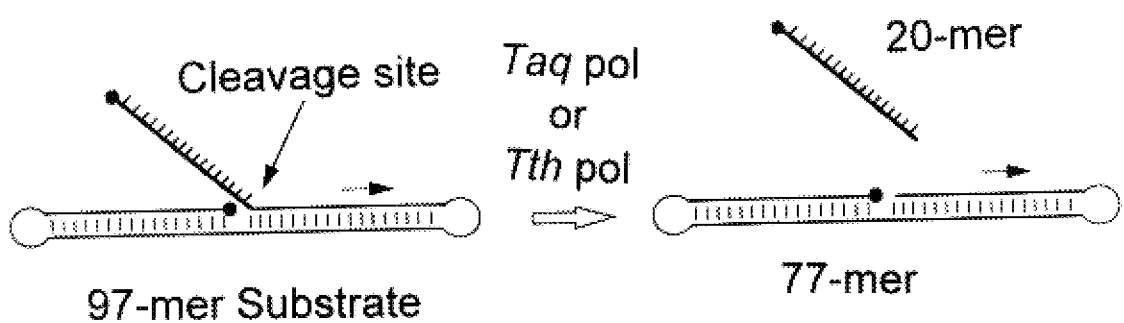
FIG. 16 illustrates schematically cleavage of the 97-nucleotide DNA sequence (Exo-Sub) (5'-TTCGAGCGTGAATCTGAATTCGCG-GCTAGCCAGCTTTTGCTG GCTAGCCGCGGTGG-GAAACTGAGGTAGGTGTTTTCACCTACCTCAG TTTCCCACC-3' (SEQ ID NO:75)), with predicted two stem-loops with a displaced strand, catalyzed by the 5'→3' exonuclease activity of Taq and Tth polymerase. Polarity of the folded sequence is indicated by the small arrow. The cleavage mediated by the exonuclease activity of the DNA polymerases is expected to occur near the junction of the displaced strand and the helix, resulting in two DNA fragments of 20-nucleotides and 77-nucleotides. Solid circles at the two ends of the molecule indicate radiolabels.

In addition to their ability to catalyze polynucleotide synthesis, Taq, Tth and TZ05 polymerase also possess 5'→3' exonuclease activity (Joyce and Steitz (1987) Trends Biochem. Sci. 12:288; Longley et al. (1990) Nucleic Acids Res. 18:7317). The preferred substrate for the 5'→3' exonuclease activity is a displaced ssDNA (or a fork-like structure) with cleavage occurring near the duplex/ssDNA junction. To study the effect of the oligonucleotide inhibitors on the 5'→3' exonuclease activity of the polymerases, DNA substrate (Exo-Sub) containing a displaced ssDNA in a hairpin was designed (Example 3, FIG. 16). Radiolabeling the Exo-Sub substrate at both the 5' and 3' ends allows detection of the two DNA fragments produced by the exonuclease activity.

Effect of Ligands TQ30 (SEQ ID NO:50) and TQ21 (SEQ ID NO:59) on the Exonuclease Activity of Taq and Tth Polymerase The two labeled DNA fragments originating from the exonuclease activity appeared both in the presence and absence of the oligonucleotide inhibitors (data not shown), however, the amount of cleavage products generated in the presence of the oligonucleotide inhibitors was somewhat lower than that produced in the absence of inhibitors, indicating that oligonucleotide inhibitors exert some inhibitory effect toward the exonuclease activity of the enzymes. Since these oligonucleotides completely inhibited the polymerase activities of the two enzymes at 250 nM, their effect on exonuclease activity is considered marginal.

Figure 17:
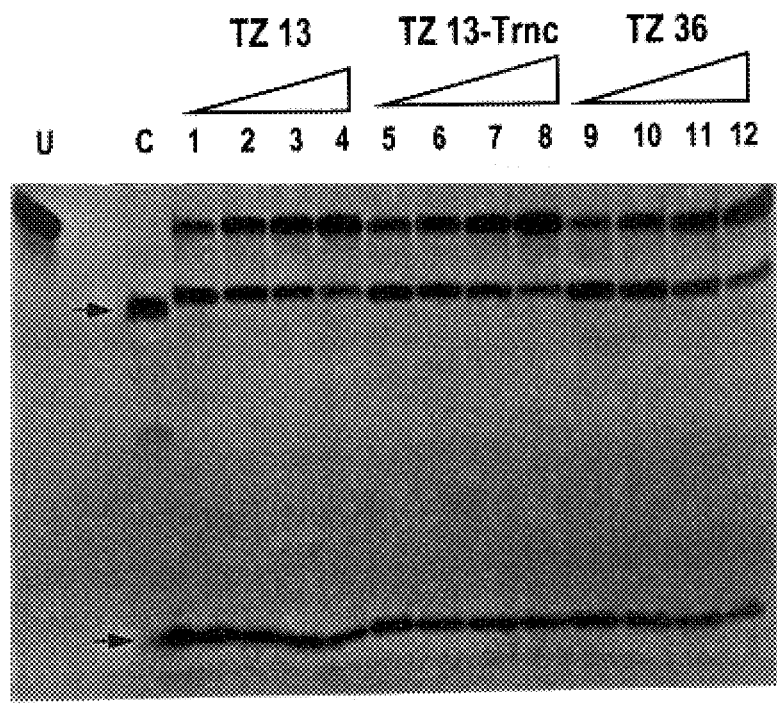
FIG. 17 depicts the analysis of the effect of ligands TZ13 (SEQ ID NO:89), TZ13 truncate (51 nucleotide) and TZ36 (SEQ ID NO:99) on the exonuclease activity of TZ05 polymerase. Lane U shows the mobility of the untreated Exo-Sub labeled at two termini. Lane C shows the cleavage products (78 nucleotides and 24 nucleotides) resulting from the exonuclease cleavage of TZ05 polymerase in the absence of ligands. Lanes 1–4, 5–8 and 9–12 show the cleavage of the Exo-Sub in the presence of increasing concentrations of TZ13, TZ13-Trnc and TZ36 ligands, respectively. Aptamer concentrations ranged from 250 nM to 2000 nM. All reactions indicated in lanes C through 12 were carried out under identical conditions.

Effect of Ligands TZ13 (SEQ ID NO:89) truncated TZ13 (51 nucleotides) and TZ36 (SEQ ID NO:99) on the Exonuclease Activity of TZ05 Polymerase FIG. 17 shows the results of an assay carried out with three ligands to TZ05 polymerase: full-length TZ13 truncated TZ13 (51 nucleotides) (see below) and full-length TZ36. Lane C shows the cleavage products (78 nucleotides and 24 nucleotides) resulting from the exonuclease cleavage of TZ05 polymerase in the absence of ligands. Lanes 1–4, 5–8 and 9–12 show the cleavage of the Exo-Sub in the presence of increasing concentrations of TZ13, TZ13-Trnc and TZ36 ligands, respectively. The cleavage of the substrate by exonuclease activity of the enzyme was inhibited by all three ligands. The inhibition of exonuclease activity is not 100% even at ligand concentrations of 2 $\mu$M. It is worth noting that at ligand concentrations of 250 nM, the polymerase activity is completely inhibited. Hence, based on the concentration of ligands required for complete inhibition of the polymerase activity and exonuclease activity, these ligands are not as effective as inhibitors of the exonuclease activity of the enzyme as they are for the polymerase activity.

Effect of Taq polymerase and TZ05 polymerase on the Ligands

Figure 18:
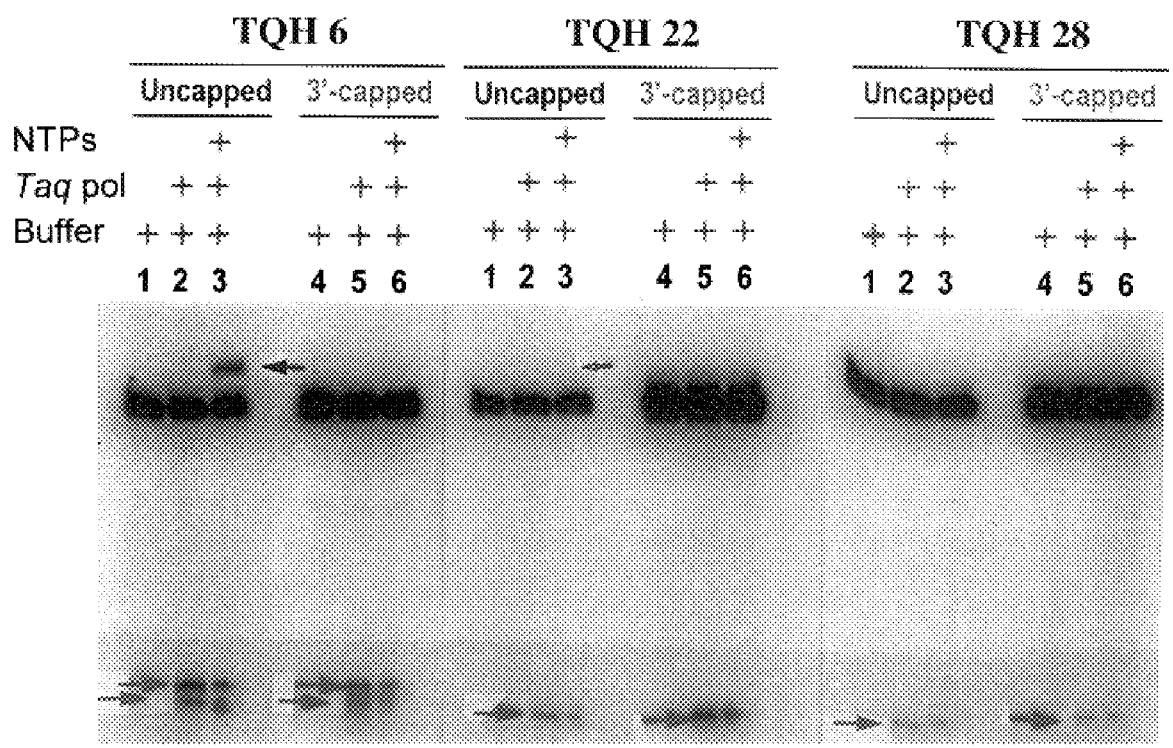
FIG. 18 illustrates the effect of Taq polymerase on 5'-labeled ligands 6 (SEQ ID NO:78), 22 (SEQ ID NO:81) and 28 (SEQ ID NO:87). For each ligand lanes I and 4 are the controls in which incubation was carried out in buffer only. Lanes 2 and 5 show the results after incubation with Taq polymerase and lanes 3 and 6 show the outcome after incubation with Taq polymerase and all four dNTPs. The bottom arrows indicate the cleavage products resulting from exonuclease cleavage, whereas the top arrows indicate the extension products of ligands.

Ideally, the nucleic acid ligands will function only as inhibitors for the polymerase activity of the enzyme, thereby making them suitable reagents to control undesirable nonspecific amplification in PCR. Depending on the nature of their folded structures, however, the ligands themselves may be substrates for either polymerase activity or 5'→3' exonuclease activity or both. To study the effect of Taq polymerase on the ligands, 5'-end labeled ligands 6 (TQH6 (SEQ ID NO:78)), 22 (TQH22 (SEQ ID NO:81)) and 28 (TQH28 (SEQ ID NO:87)) were incubated with Taq polymerase in the presence and absence of dNTPs and the reaction products were analyzed by polyacrylamide gel electrophoresis under denaturing conditions. FIG. 18 illustrates the effect of Taq polymerase on each of these ligands. For each ligand lanes 1 and 4 are the controls where incubation was carried out in the buffer. Lanes 2 and 5 show the results after incubation with Taq polymerase and lanes 3 and 6 show the outcome after incubation with Taq polymerase and all four dNTPs. As can be seen in FIG. 18, when incubated with Taq polymerase, lanes 2, 3, 5 and 6, all three ligands have served as substrates for exonuclease activity, as indicated by the appearance of fast-moving small DNA fragments. What is in fact observed, is the structure-specific endonuclease activity of the 5'→3' exonuclease activity of Taq polymerase that has been described by Holland et al. (1991) Proc. Natl. Aca. Sci, U.S.A. 88:7276–7280. In addition to being substrates for exonuclease activity, each of the ligands was also extended by the polymerase activity when incubated in the presence of dNTPs (lane 3). This is clearly noticeable in ligand 6, in which a slow-moving band was generated upon incubation with the polymerase and dNTPs. As shown in lanes 4–6, the polymerase extensions were completely stopped by blocking the availability of the 3' OH groups of each ligand. In this study, the 3' ends were capped with phosphate groups during the chemical synthesis of ligands. In addition to phosphate groups, other molecular entities such as ethylene glycol linkers and 3'—3'dT linkage can also be used for capping the 3' ends of the ligands effectively. The capping of the 3' ends of the ligands eliminates the potential problem of ligands acting as nonspecific primers in PCR. The capping of 3' ends of ligands did not affect the function of ligands (Dang and Jayasena (1996) J. Mol. Biol. 264:268).

To study the effect of TZ05 polymerase on the ligands, 5'-end labeled ligands to TZ05 were incubated with TZ05 polymerase in the presence of dNTPs. Most of the ligands when incubated with dNTPs and TZ05 polymerase showed extension products, indicating that ligands serve as substrates for polymerase activity. Additionally, all of the ligand sequences tested were cleaved into two fragments by the 5'→3' exonuclease activity of TZ05 polymerase (data not shown). Though the exact site of cleavage was not mapped, it appeared to be somewhere in the 5'-fixed region. As discussed above, polymerase extension on ligands can be effectively controlled by blocking the 3' hydroxyl groups of the ligands. However, the cleavage of ligands by the exonuclease activity of polymerase will generate novel 3' ends in situ, leading to two possible consequences. First, the cleavage may potentially inactivate the finction of ligands, and second, the DNA fragments with novel uncapped 3' ends can act as nonspecific primers in PCR. These observations led to the identification of the truncated ligands described below.

Inhibition of Various DNA Polymeraes by TQ21
(SEQ ID NO:59) and TQ30 (SEQ ID NO:50

Inhibition assays using several other commercially available DNA polymerases and ligands TQ21 (SEQ ID NO:59) and TQ30 (SEQ ID NO:50) as inhibitors are described in Example 4. Four thermostable enzymes (Tbr polymerase from *Thermus brockianus,* Tfl polymerase from *Thermus flavus* Tma polymerase from *Thermotoga maritima* and Tfl polymerase from *Thermococcus litoralis*); three mesophilic enzymes (Klenow fragment of *E. coli* DNAP1 (KF), T4 DNA polymerase and T7 DNA polymerase); and four reverse transcriptases (RT) (HIV-I RT, AMV (avian myeloblastosis virus) RT and M-MLV (moloney murine leukemia virus) RT and its mutant lacking RNase H activity (SuperScript II) were examined.

Of the six thermostable polymerases examined (including Taq and Tth polymerase), the four polymerases derived from Thermus species (Taq, Tth, Tbr and Tlf) were inhibited by both of the selected oligonucleotides, suggesting that these enzymes share a high degree of similarity. As stated above, Tth polymerase and Taq polymerase are reported to be 93% similar and 88% identical at the amino acid sequence level (Abramson (1995) in *PCR Strategies* (Academic Press, New York). Tfl polymerase is reported to be 93% similar and 86% identical to Taq polymerase at the amino acid level (D. Gelfand, personal communication). Tma polymerase from *Thermotoga maritima* and Tli polymerase from *Thermococcus litoralis,* on the other hand, were not inhibited by either of the ligands. Tli polymerase shares little sequence homology with eubacterial enzymes (Ito and Braithwaite (1991) Nucleic Acids Res. 19:4045). Tma polmerase is reported to be 61% similar and 44% identical to Taq polymerase at the amino acid level (Abramson (1995) in *PCR Strategies* (Academic Press, New York), yet the oligonucleotide ligands do not inhibit Tma polymerase.

Of the four reverse transcriptases tested, RTs from HIV-I and AMV (avian myeloblastosis virus) were not inhibited. On the other hand, RT from M-MLV (moloney murine leukemia virus) and its mutant lacking RNase H activity (SuperScript II) were inhibited by the two oligonucleotide ligands.

Mesophilic DNA polymerases, such as, Klenow fragment of *E. coil* DNAP1 (KF), T4 DNAP and T7 DNAP were not inhibited by either ligand at 0.5 $\mu$M concentration, despite the similarity of the polymerase domains of Taq polymerase and KF (Kim et al. (1995) Nature (London) 376:612; Lawyer et al. (1989) J. Biol. Chem. 264: 6427). Thus, it appears that the oligonucleotide inhibitors are generally fairly specific. These results are similar to the behavior of nucleic acid ligands identified by in vitro selection for other reverse transcriptases (Tuerk and MacDougal (1994) Proc. Natl. Acad. Sci, U.S.A. 89:6988; Chen and Gold (1994) Biochemistry 33:8746; Schneider et al. (1995) Biochemistry 34:9599).

Inhibition of Various DNA Polymerases by TQH6
(SEQ ID NO:78) and TQH22 (SEQ ID NO:81)

Figure 19A:
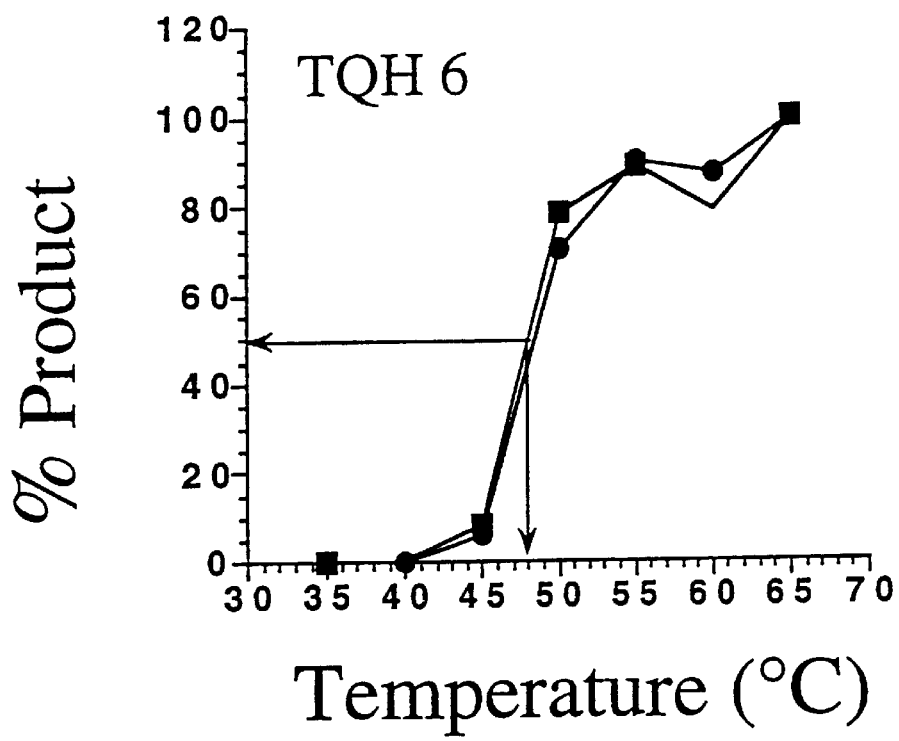
FIGS. 19A and B depict the inhibition of the Stoffel fragment by full-length (●) and truncated (■) ligands of TQH6 (SEQ ID NO:78) (FIG. 19A) and TQH22 (SEQ ID NO:8 1) (FIG. 19B). The extension product of the hairpin substrate was quantified by phosphoimager and normalized to the product formed in the absence of an inhibitor at the same temperature to obtain the percent product. The temperature at which 50% of the product was formed is the $IT_{50}$ value of a ligand.
Figure 19B:
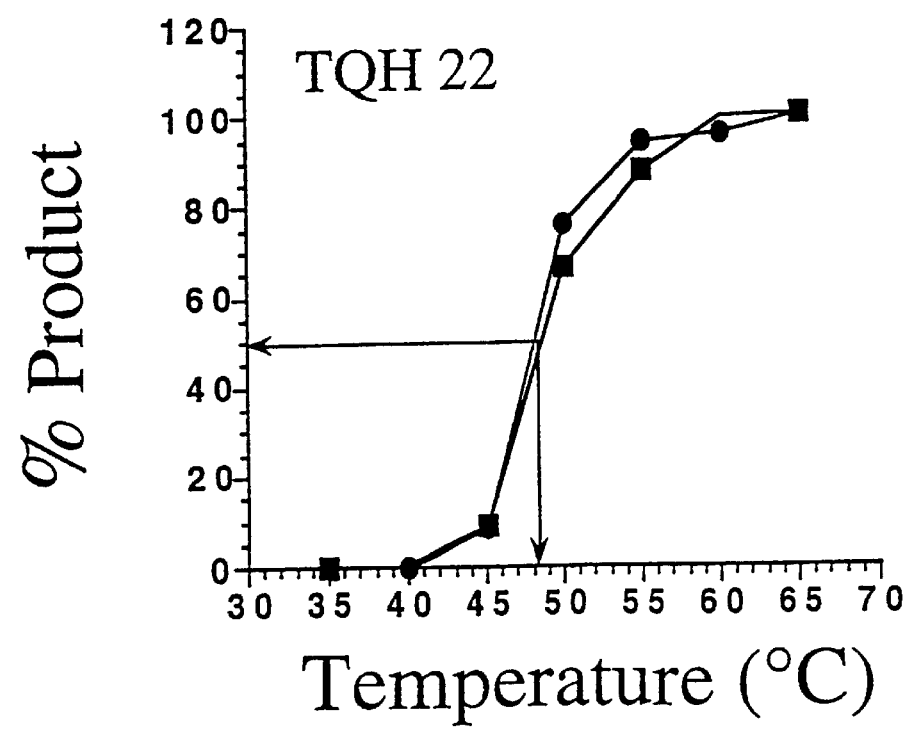

Both full-length and truncated forms of TQH6 and TQH22 were studied to determine their ability to inhibit the Stoffel fragment of Taq polymerase, Tth polymerase and TZ05 polymerase. Both ligands inhibited the Stoffel fragment with an $IT_{50}$ value of 48° C. (FIGS. 19A and B). In both cases full-length and truncated ligands exhibited identical $IT_{50}$ values. This result is quite different from the inhibition of Taq polymerase by these two ligands in which the truncated ligands exhibited lower $IT_{50}$ values than the full-length molecules.

Figure 20A:
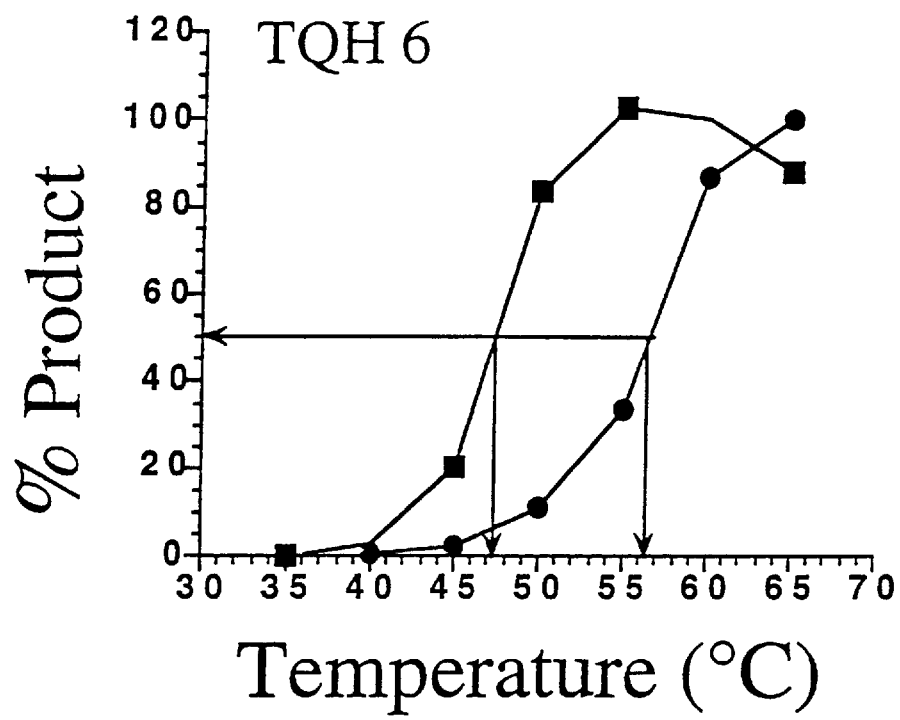
FIGS. 20A and B depict the inhibition of Tth polymerase by full-length (●) and truncated (■) ligands of TQH6 (FIG. 20A) and TQH22 (FIG. 20B). The extension product of the hairpin substrate was quantified by phosphoimager and normalized to the product formed in the absence of an inhibitor at the same temperature to obtain the percent product. The temperature at which 50% of the product was formed is the $IT_{50}$ value of a ligand.
Figure 20B:
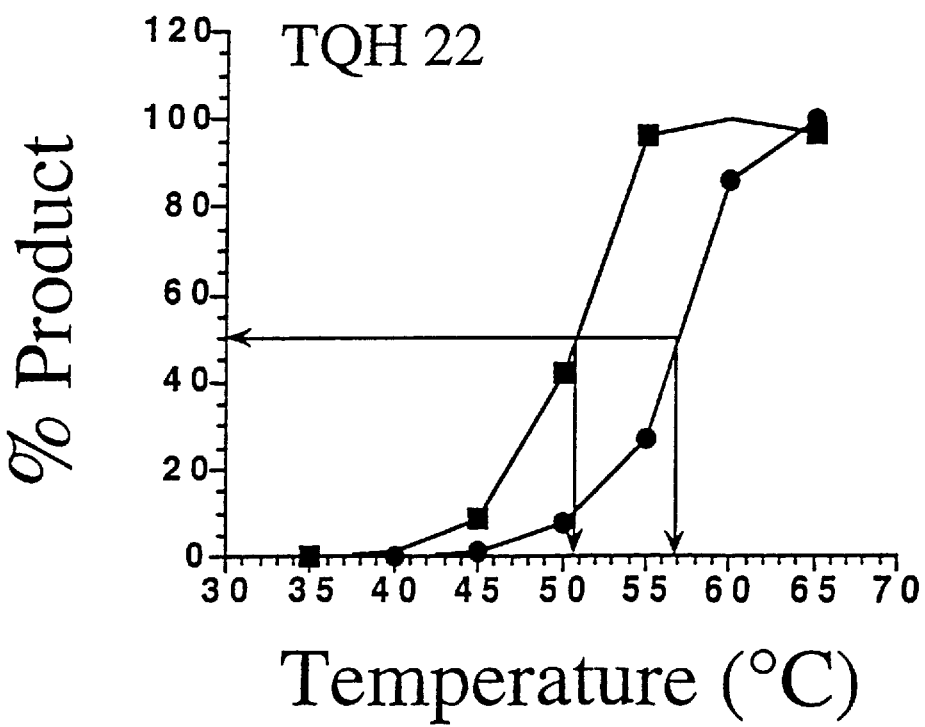

The inhibitory characteristics of the full-length and the truncated forms of the two ligands on Tth polymerase is very similar to those on Taq polymerase. In both cases truncated ligands showed lower $IT_{50}$ values (6° C. or 10° C.) (FIGS. 20A and B).

Figure 21A:
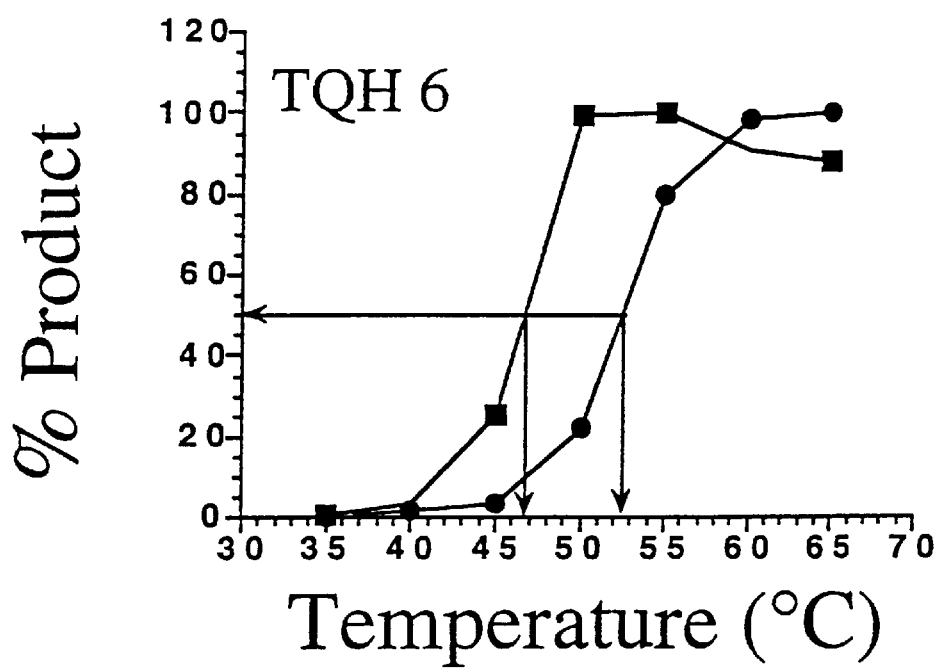
FIGS. 21A and B depicts the inhibition of TZ05 polymerase by full-length (●) and truncated (■) ligands of TQH6 (FIG. 21A) and TQH22 (FIG. 21B). The extension product of the hairpin substrate was quantified by phosphoimager and normalized to the product formed in the absence of an inhibitor at the same temperature to obtain the percent product. The temperature at which 50% of the product was formed is the $IT_{50}$ value of a ligand.
Figure 21B:
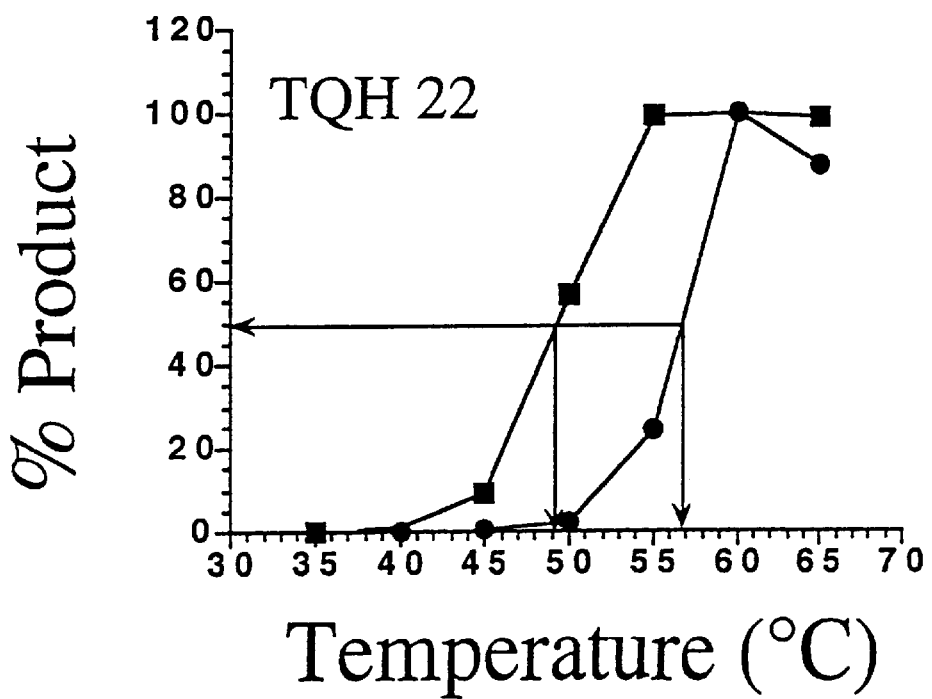

The inhibition of TZ05 polymerase by the two ligands was investigated in the presence of either $Mg^{2+}$ or $Mn^{2+}$ ions. Very similar results were observed in the presence of either metal ion. FIGS. 21A and B show the inhibition of TZ05 polymerase in the presence of $Mg^{2+}$ ions.

Inhibition of Various DNA Polymerases by TZ1
(SEQ ID NO:94), TZ8 (SEQ ID NO:100), TZ13
(SEQ ID NO:89) and TZ54 (SEQ ID NO:103)

Figure 22A:
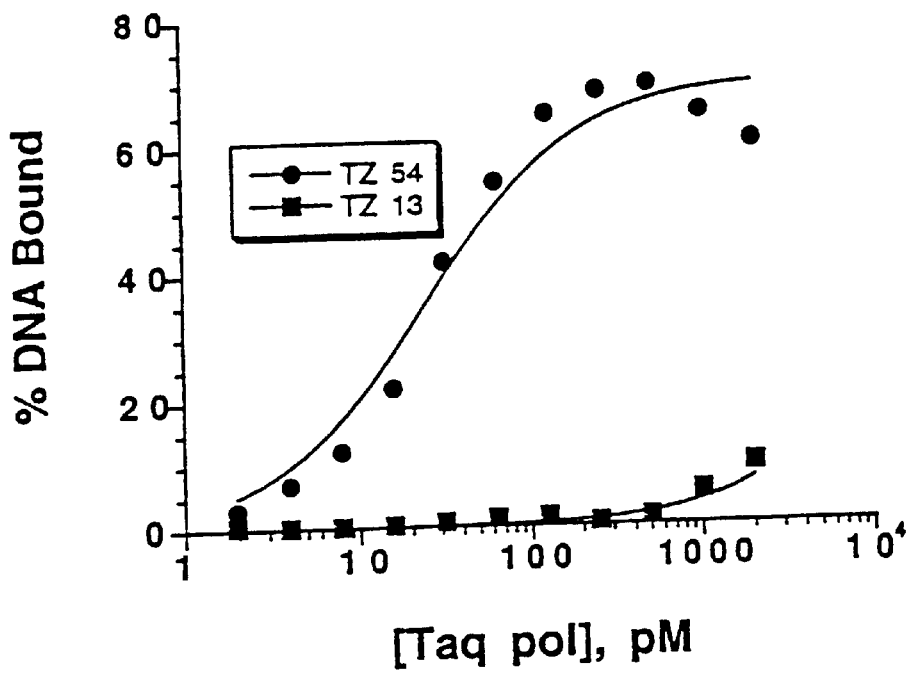
FIGS. 22A and B depict the binding analysis of TZ13 (SEQ ID NO:89) (■) and TZ54 truncate (51 nucleotide) (●) to Taq polymerase (FIG. 22A) and Tth polymerase (FIG. 22B).
Figure 22B:
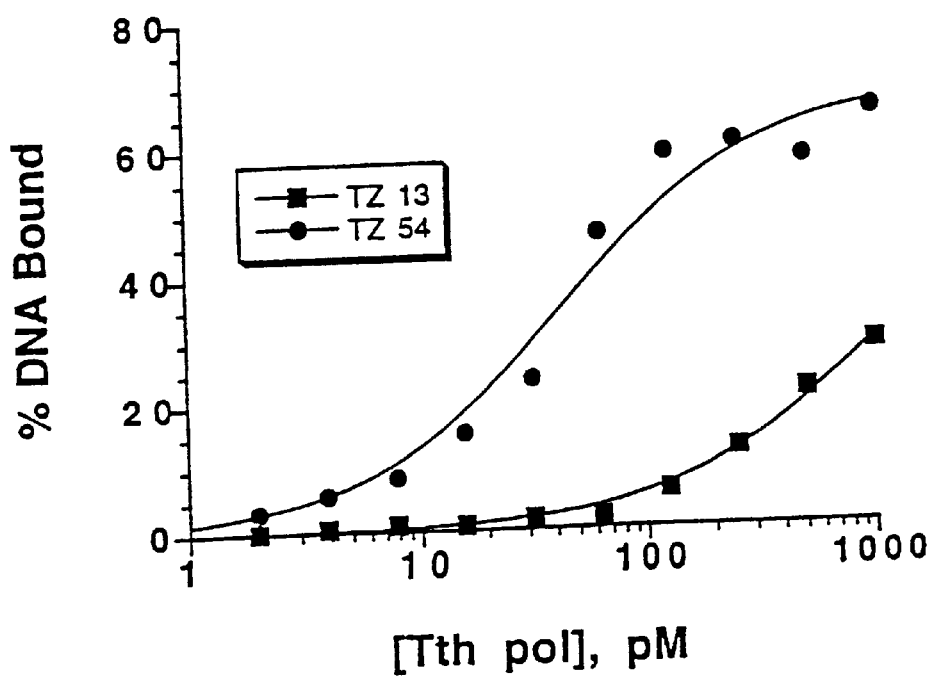
Figure 23A:
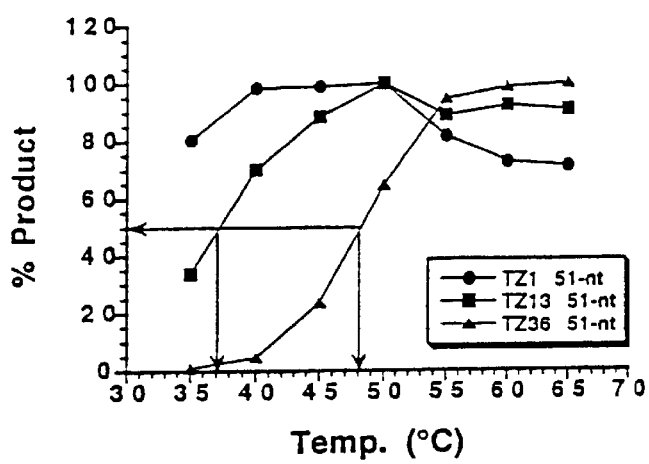
FIGS. 23A–C depict the analysis of the inhibition of various thermostable DNA polymerases by ligands TZ1 (SEQ ID NO:94) (●), TZ13 (SEQ ID NO:89) (■) and TZ36 (SEQ ID NO:99) (▲), which were selected to bind TZ05 polymerase at high temperature.
Figure 23B:
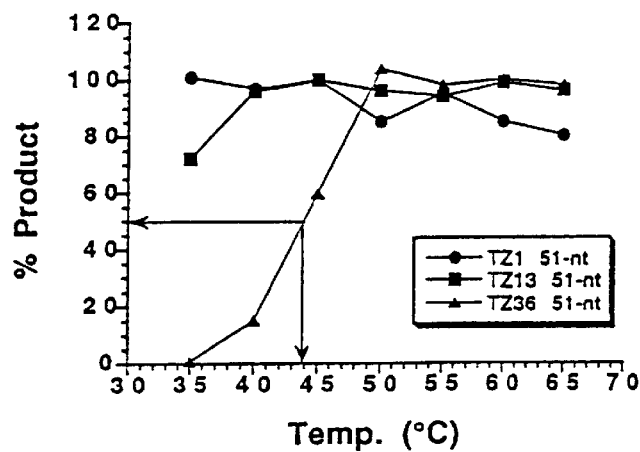

Several ligands derived from the affinity selection of TZ05 polymerase were used to investigate the inhibition of Taq polymerase, Tth polymerase and the Stoffel fragment by these ligands. Out of several full-length ligands tested from different families, ligands carrying the consensus with four contiguous thymines, i.e. sequences categorized under Family III, (TZ8 (SEQ ID NO:100) and TZ54) effectively inhibited both Taq and Tth polymerases (data not shown). This result is not all that surprising based on the fact that Family II ligands identified by affinity selection on Taq polymerase (Table 4) also inhibited Tth polymerase, as well as, polymerases from *Thermus brokianus* and *Thermus flavus.* The observed inhibition by TZ54, a ligand containing a consensus motif with four thymines, but not by TZ13, a ligand with seven contiguous guanines mirrors their binding affinities to Taq and Tth polymerases (FIGS. 22A and B). As shown in FIG. 22, TZ13 does not bind with high affinity to either polymerase, whereas TZ54 does. On the other hand, TZ1 and TZ13, which contain seven contiguous guanines do not show effective inhibition of these two polymerases above 30° C. (FIGS. 23A and B). Ligand TZ36 is unique in that it has neither the seven contiguous guanosines nor the contiguous four thymines and it inhibits both Taq and Tth polymerases effectively. Hence, it is likely that ligands containing seven contiguous guanines are specific to the TZ05polymerase, the polymerase that was used in the affinity selection.

Figure 23C:
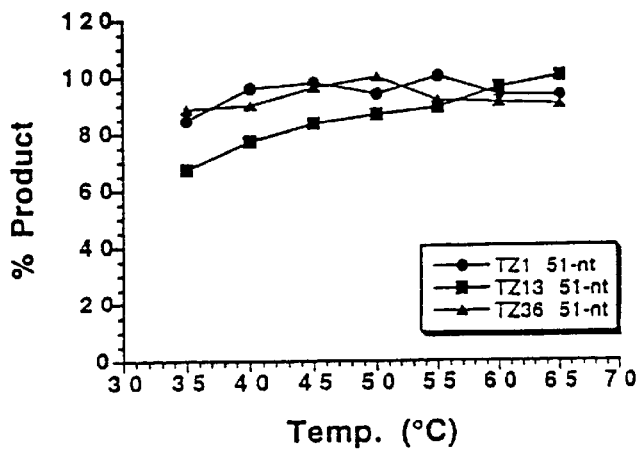

None of the three ligands tested (TZ1, TZ13 and TZ36) inhibited the Stoffel fragment (FIG. 23C). This result is surprising for TZ36, which effectively inhibited Taq polymerase. This suggests that the binding site of TZ36 on Taq polymerase is either deleted or reorganized in the Stoffel fragment.

Amplification of Low Copy Number Targets

Example 5 describes a number of PCR amplifications comparing stardard PCR techniques, "hot start" PCR and PCR using the ligands identified by the method of this invention to facilitate the detection of a low copy number target by PCR in the absence of "hot start" conditions. A primer-template system designed to detect a 203-base pair (bp) DNA fragment from the HIV-2 LTR (long terminal repeat) as described by Respess et al. (1994) in *Interscience Conference on Antimicrobial Agents and Chemotherapy* 94:110 was utilized.

Figures 24A, 24B, 24C:
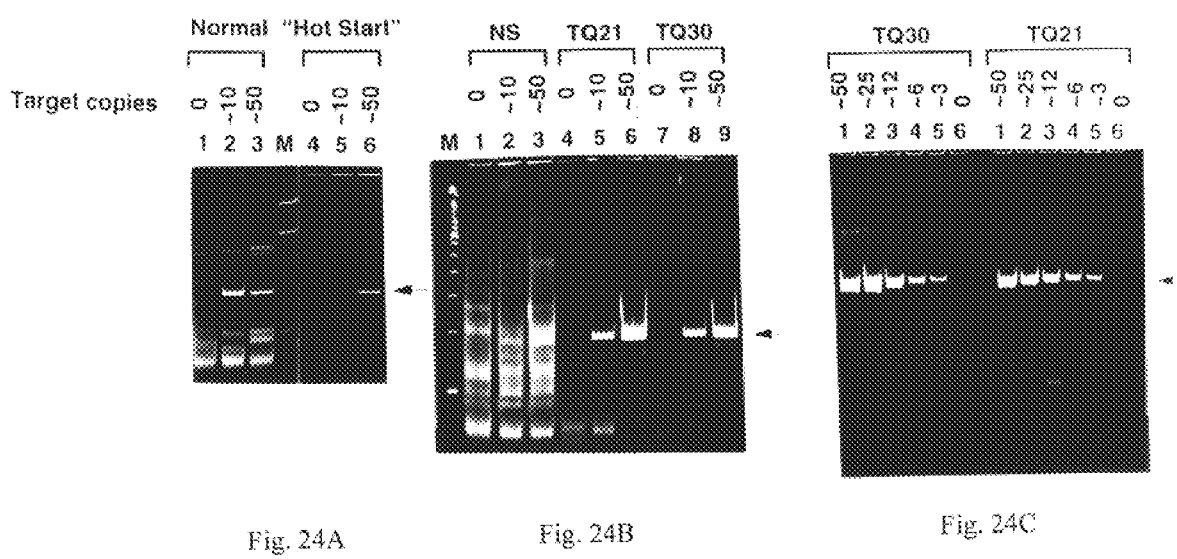
FIGS. 24A–C illustrate the detection of a low copy number target using standard PCR amplification, "hot start" PCR and PCR amplification in the presence of oligonucleotide inhibitors TQ30 (SEQ ID NO:50) and TQ21 (SEQ ID NO:59) ("NeXstart PCR").

FIG. 24 illustrates the results using ligands TQ30 (SEQ ID NO:50) and TQ21 (SEQ ID NO:59). The PCR amplifications were carried out with 0, 10 and 50 copies of HIV-2 LTR target. Under normal PCR conditions, the identification of the correct target band was compromised by the presence of a number of nonspecific bands (FIG. 24A, lanes 1–3). Amplification carried out under "hot start" conditions eliminated the nonspecific bands (FIG. 24A, lanes 4–6). The results of amplification performed in the presence of a nonspecific 78-nucleotide ssDNA sequence containing identical 5'- and 3'-fixed sequences as TQ21 and TQ30 (FIG. 24B, lanes 1–3) were similar to those obtained by PCR without using "hot start" conditions. However, the addition of either TQ21 (FIG. 24B, lanes 4–6) or TQ30 (FIG. 24B, lanes 7–9) carried out under standard conditions (without "hot start") eliminated the nonspecific bands without affecting the yield of the target-specific band. Of particular importance was the observation that when the target copy number was low, signal detection was very efficient (FIG. 24B, compare lane 2 with lanes 5 and 8). The effect of oligonucleotide inhibitors was similar when Tth polymersase was used in place of Taq polymerase (data not shown) in detecting low copy number HIV-2 LTR. The enhanced yield of the target-specific band obtained with the oligonucleotide inhibitors in PCR increases the sensitivity of the reaction, facilitating detection of the target present with only approximately 3 copies (FIG. 24C).

The oligonucleotide inhibitors used in the experiment described in FIG. 24 were uncapped at their 3' ends, potentially permitting them to initiate amplification nonspecifically, and further complicating the outcome of PCR. However, no adventitious bands were detected, suggesting that in this system, 3'-capping of oligonucleotide inhibitors was not required to eliminate the generation of nonspecific bands.

Figure 25:
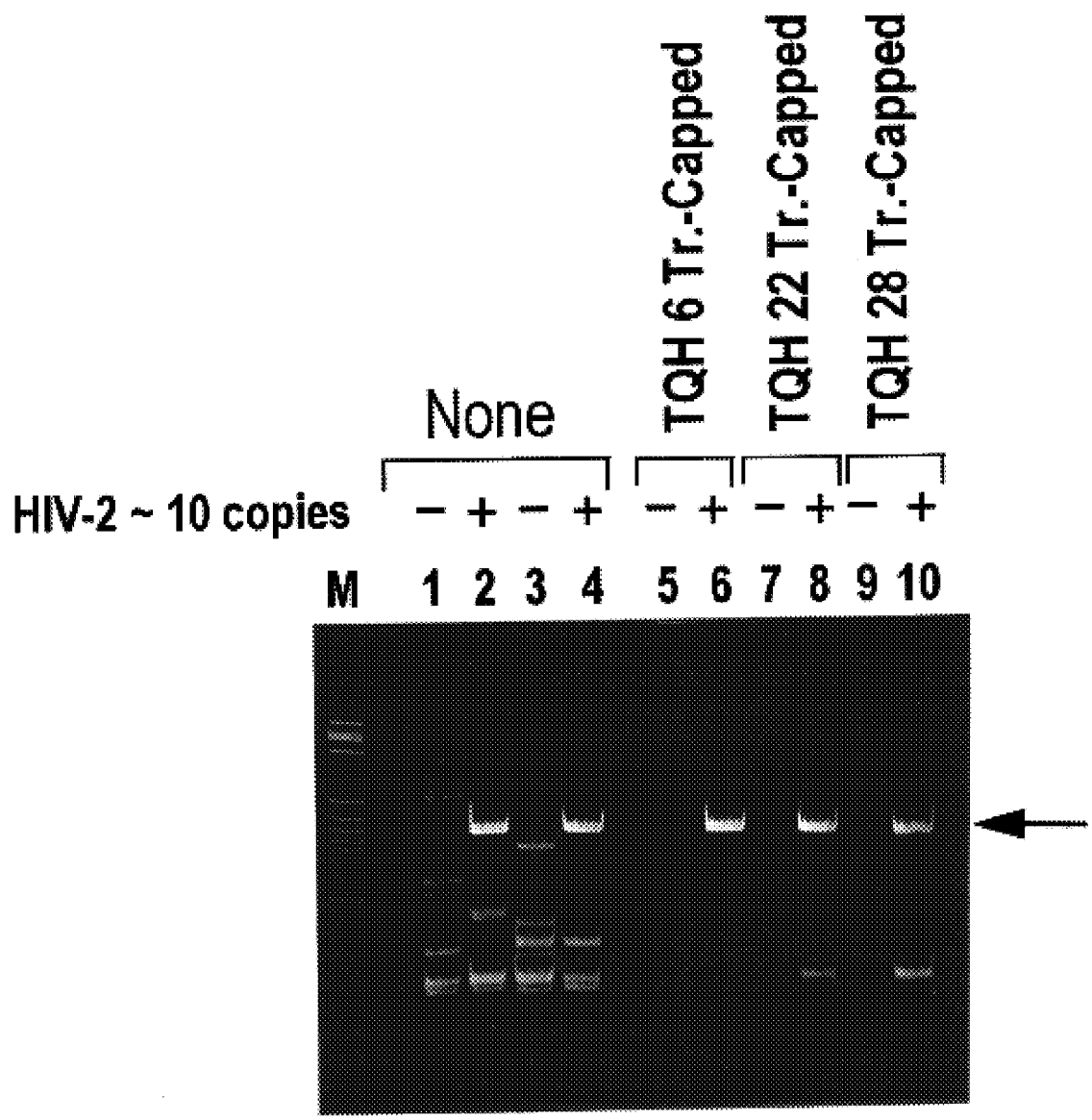
FIG. 25 illustrates the detection of a low copy number target using PCR amplification in the presence of truncated oligonucleotide inhibitors of ligands TQH6 (SEQ ID NO:78), TQH22 (SEQ ID NO:81) and TQH28 (SEQ ID NO:87) ("NeXstart PCR"). All PCR amplifications were carried out in the presence of 1 μg of human placental DNA with no manual "hot start." Lanes 1–4 show the results of the PCR amplification carried out in the absence of a ligand. Reactions shown in lanes with odd numbers contained no HIV-2 template DNA, whereas those indicated in even numbers contained 10 copies of HIV-2 genomic DNA. The arrow indicates the specific amplicon.

FIG. 25 illustrates the results using 3' capped truncated ligands: TQH6, TQH22 and TQH28. The amplifications were carried out with and without 10 copies of HIV-2 LTR target mixed with 1 μg of human placental DNA. All of the amplifications depicted in FIG. 25 were performed in the absence of hot start conditions. Lanes 1–4 show the outcome of control reactions that did not contain ligands. In these reactions multiple DNA bands were generated due to nonspecific amplification. These nonspecifically amplified products are present in reactions with and without the template DNA. The outcome is clearly different when the ligands are added to the reaction mixture (lanes 5–10). In the case of all three ligands, there was not a single product of amplification in reactions that did not contain the target (lanes 5, 7 and 9). In PCR reactions that contained target only the specific amplicon was amplified when ligand TQH6 (lane 6) was added to the reaction mixture and when ligands TQH22 and TQH28 were added, an additional low molecular weight band was present, presumably due to the nonspecific annealing of the primer to the target (lanes 8 and 10). These results indicate that these truncated ligands are effective in controlling the nonspecific amplification by generating in situ hot start conditions.

Figure 26:
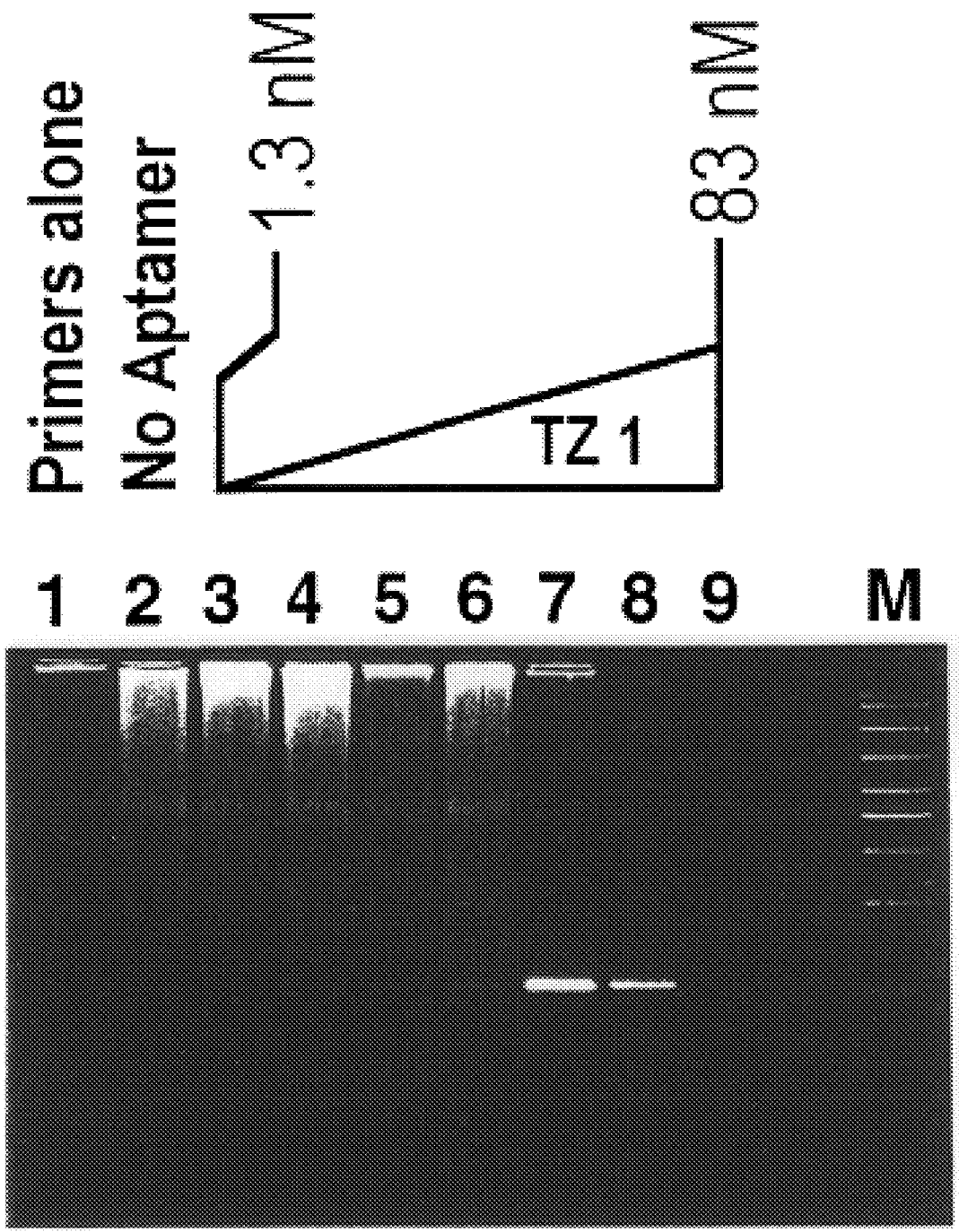
FIG. 26 illustrates the detection of a low copy number target using a PCR system that amplifies 104 bp amplicon from the human K-ras gene. All amplification reactions containing TZ05 DNA polymerase were carried out without manual hot start conditions. In lane 1 no template DNA was added; in lane 2 no aptamer was added; in lanes 3–9 complete PCR was performed using increasing concentrations of the 51 nucleotide truncated TZ1 ligand. The ligand concentration was doubled from one reaction to the next starting with a concentration of 1.3 nM. Lane M depicts DNA size standards.

To test the ability of ligands to TZ05 polymerase to improve the outcome of PCR that amplify a low copy number target sequence, a PCR system designed to amplify K-ras gene from human genomic DNA was used. (Nilsson et al (1997) BioTechniques 22:744–751). The 51 nucleotide truncated ligands of TZ1 (TZ1-Tr (SEQ ID NO:107)), TZ13 (TZ13-Tr (SEQ ID NO:108)) and TZ36 (SEQ ID NO:109)) (FIG. 33) were tested. The 3' OH group of these ligands were capped with a 3'—3'dT residue to prevent polymerase extension of the ligands. Moreover, these ligands contained eight phosphorothioate linkages at the 5' terminus to block the exonuclease cleavage by TZ05 polymerase. In amplification reactions, the ligand was present in the complete reaction buffer containing the polymerase and primers prior to the addition of template human genomic DNA. After PCR, amplified products were analyzed on a 3% agarose gel. The results of PCR performed in the presence of truncated TZ1 ligand over a range of concentration is shown in FIG. 26. In the absence of or at low concentration of ligand, the K-ras gene was not amplified (lanes 2–6). As the concentration of the ligand is increased, the generation of the specific amplicon with decreasing amount of background can be seen (lanes 7–8). PCR was completely inhibited upon further increase in the ligand concentration (lane 9). The results indicate that an optimum concentration of ligand that falls between 20–40 nM is required for desirable amplification. The results using the other two ligands were very similar to the results shown in FIG. 26.

Figure 27A:
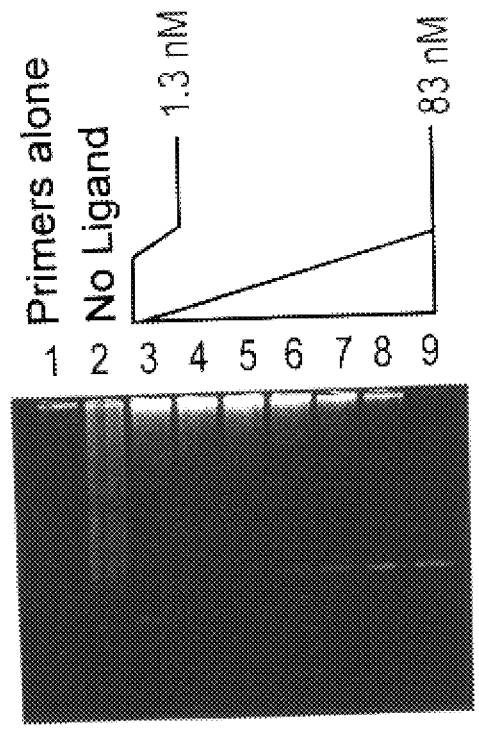
FIGS. 27A and B depict the amplification of the human K-ras gene by TZ05 polymerase in the presence of the 30 nucleotide truncates of TZ1 (FIG. 27A) and TZ13 (FIG. 27B). All amplification reactions containing TZ05 DNA polymerase were carried out without manual hot start conditions. In lane 1 no template DNA was added. In lane 2 no ligand was added. Lanes 3–9 show complete PCR with increasing concentration of the respecitve ligand. The ligand concentration was doubled in each successive reaction starting with a concentration of 1.3 nM.

Similar results were obtained with the 30 nucleotide truncates of TZ1 and TZ13 (FIGS. 27A and B). These truncates did not have phosphorothioate linkages at 5' ends, but were capped at the 3' ends. With the 30 nucleotide truncates the concentration required to achieve desirable outcome was approximately twice of that required for 51 nucleotide truncates. Similar results were observed with the 26 nucleotide truncate of TZ13 at an even higher concentration (660 nM) than the 30 nucleotide truncate. The effective concentrations of truncated ligand required to produce the target-specific amplicon decreases with the decrease in length of a ligand. This result correlates with their $IT_{50}$ values, which also decrease with the decrease in length of a ligand.

Figure 27B:
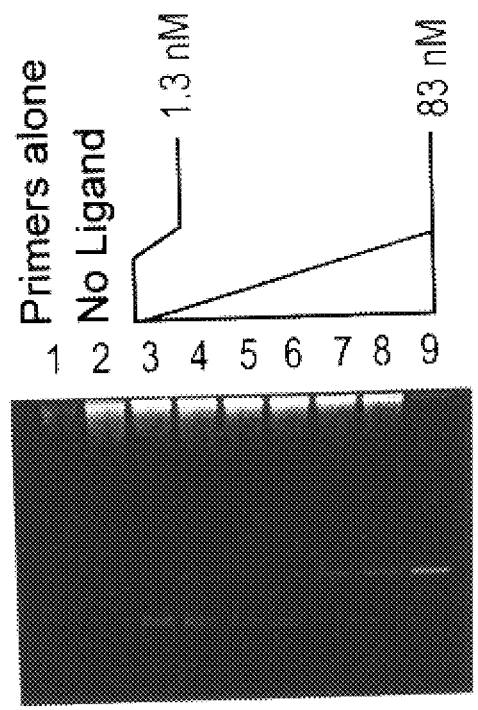
Figure 28:
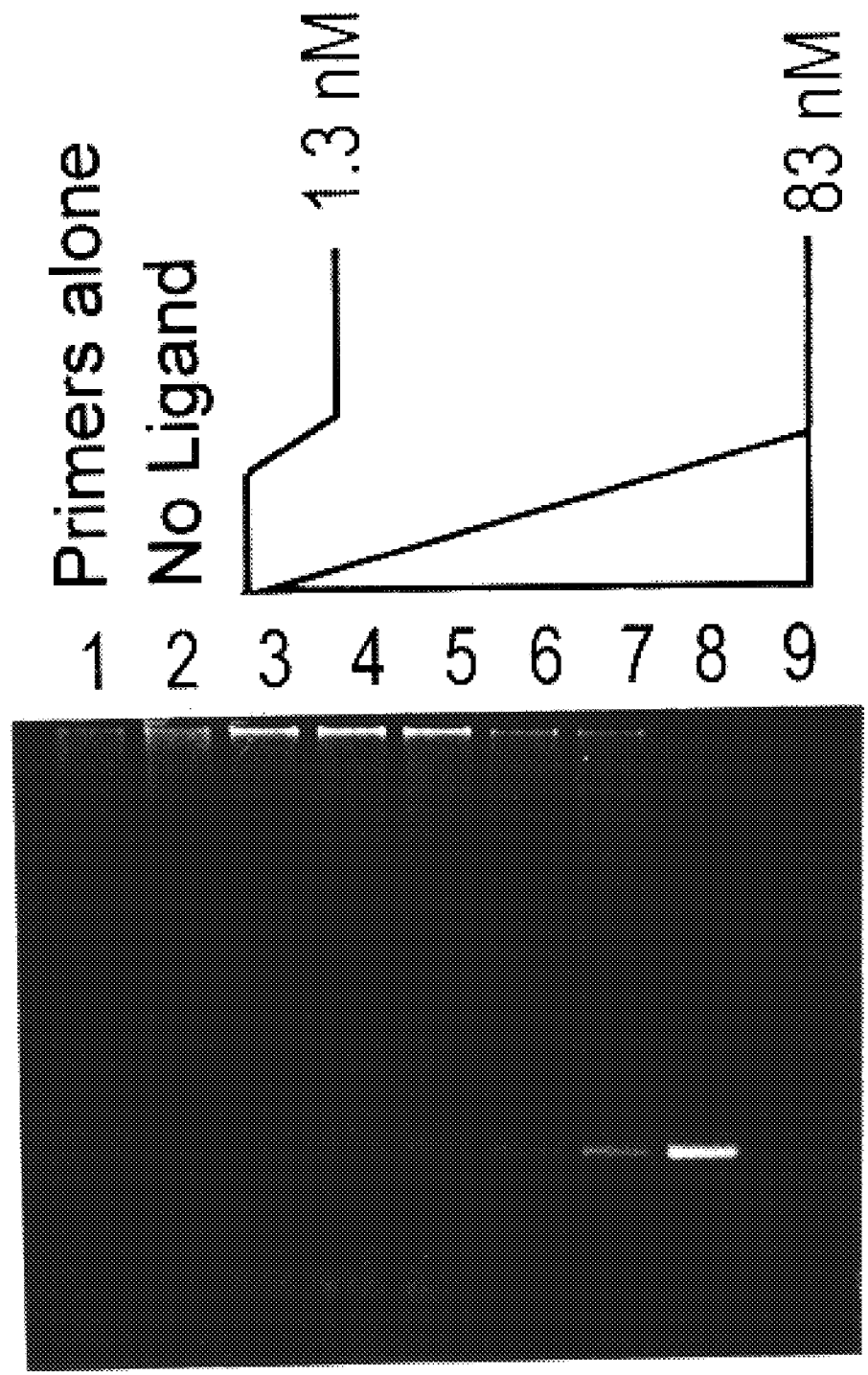
FIG. 28 depicts the amplification of the human K-ras gene by Tth DNA polymerase in the presence of the 51 nucleotide truncate of TZ36. All amplification reactions contained Tth DNA polymerase and were carried out without manual hot start conditions. In lane 1 no template DNA was added. In lane 2 no aptamer was added. Lanes 3–9 show the results of complete PCR with increasing concentration of ligand. The ligand concentration was doubled in each successive reaction starting with a concentration of 1.3 nM.

The amplifications shown in FIGS. 26 and 27 were carried out with TZ05 polymerase. Several ligands selected to recognize TZ05 polymerase also inhibited Tth polymerase. The ligand TZ36 (51 nucleotide truncate) was tested in the same PCR system carried out with Tth polymerase. As shown in FIG. 28, the ligand is quite effective in generating specific amplicons with Tth polymerase as well.

Identification of Truncated Ligands with Inhibitory Activity

Typically, not all nucleotides in a full-length sequence are necessary for its finction. Identification of truncated DNA sequences that retain the finction of the whole sequence, therefore, is desirable. Additionally, as discussed above, the full-length sequences undergo site-specific cleavage by the structure-specific endonuclease activity associated with the polymerase. This poses a potential problem in PCR applications due to either the generation of extendable 3' ends or the possible inactivation of ligand function upon cleavage or both. As a result, ligands that are not substrates for exonuclease activity are desirable. Since the cleavage site is near the 5' end of the sequence, truncation may eliminate this site. Truncation is also desirable due to the economics of manufacturing the ligands.

Identification of Truncated Ligands of TQ30 and TQ21

Ligands TQ30 (SEQ ID NO:50) from Family I and TQ21 (SEQ ID NO:59) from Family II (see Table 10) were chosen for truncation experiments. Affinity selections on end-labeled nested fragments generated from the full-length sequences of both ligands, followed by sequencing gel analysis, as described in Example 2, did not give identifiable boundaries. The two ligands were therefore subjected to deletion analysis. Sequentially deleted forms were tested for their ability to inhibit polymerases in the hairpin extension assay to identify functional truncates.

Truncates of ligand TQ30 (SEQ ID NO:50)

The variable 30-nucleotide region of TQ30 containing the conserved sequence motif with the predicted stem-loop structure (Trnc.A-30 (SEQ ID NO:74); Table 5) inhibits Taq polymerase at 25° C. to the same extent as the full-length sequence (data not shown). At higher temperatures, however, the efficiency of inhibition is lower than the full-length sequence. At 30° C., for example, the inhibition of Taq polymerase by Trnc.A-30 (250 nM) is approximately 82%, whereas the full-length sequence completely inhibited the enzyme at this temperature and concentration. The increased thermal sensitivity of Trnc.A-30 may be due to the presence of an interrupted helix with A-T base pairs, a helix with propensity to melt at a low temperature.

Figure 29:
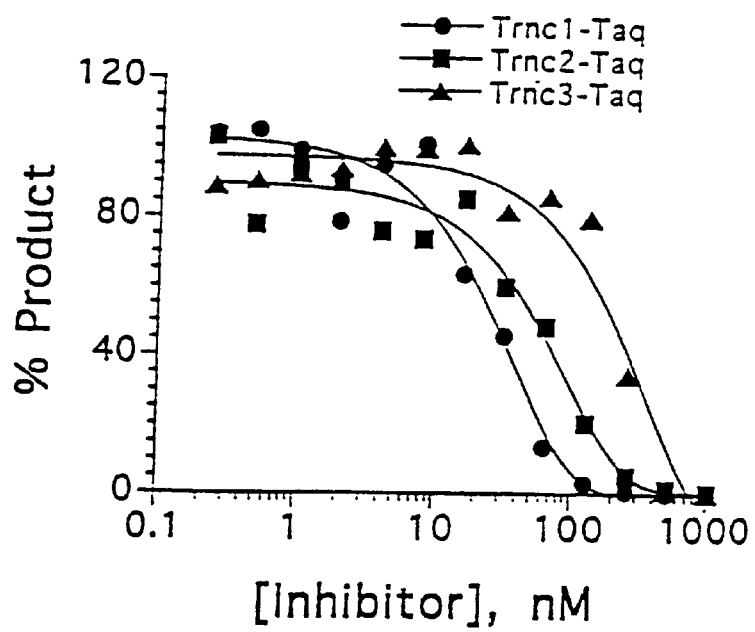
FIG. 29 depicts the effect of the concentration of truncated ligands Trunc. 1–30 (SEQ ID NO:75) (●), Trnc.2–30 (SEQ ID NO:76) (■) and Trnc.3–30 (SEQ ID NO:77) (▲) on the activity of Taq polymerase. The amount of product formed in the presence of varying concentrations of inhibitor was quantitated by phosphorimager and normalized to the amount of product formed in the absence of an inhibitor to obtain the percent product (abscissa).

Three stem-loop variants of Trnc.A-30 containing uninterrupted stems with high G-C base pairs were therefore designed. In these variants the conserved sequence motif identified in Family I was unaltered (Table 5), but the stems had varying lengths. At 250 nM inhibitor concentration, Trnc.1–30 (SEQ ID NO:67) and Trnc.2–30 (SEQ ID NO:68) inhibited approximately 95% of the activity of Taq polymerase, whereas Trnc.3–30 (SEQ ID NO:69) inhibited only about 60% of the polymerase activity (see below). Trnc.3–30 containing the shortest stem (7-base pairs) of the three variants was a poor inhibitor for Taq polymerase, indicating that additional contacts in the stem are required for productive interaction. To determine whether the decreased inhibition observed with Trnc.3–30 is due to its reduced affinity to bind to the polymerase, the affinities of all three variants for binding to Taq polymerase were calculated. The $K_d$ values fell between 2–3 nM (Table 5), indicating that all three variants had similar binding affinities. Hence, the lack of inhibition caused by Trnc.3–30 was not due to lack of binding, but presumably due to its inability to block the active site. Affinities of the three variants for binding to Taq polymerase are about 75-fold lower than the full-length molecule ($K_d$ of the full-length sequence is 40 pM), and about 3–5-fold lower than Trnc.A-30. The $IC_{50}$ values for the three constructs decreased with the decrease in length of the stem; 25, 50 and 186 nM for Trnc.1–30, Trnc.2–30 and Trnc.3–30, respectively (FIG. 29). This result is in agreement with the notion that the ligands with longer stems are more effective inhibitors. The $IC_{50}$ value of the full-length sequence is 22 nM. Hairpin extension assays were preformed at 30° C. for 1 hour. Neither Trnc.1–30 nor Trnc.2–30 inhibit Tth polymerase, despite the fact that the enzyme is completely inhibited by the full length ligand.

Figure 30:
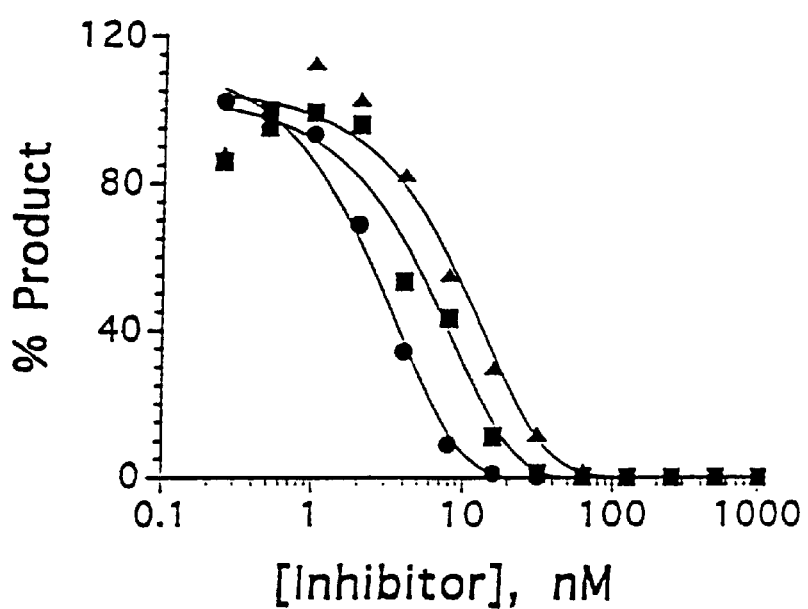
FIG. 30 depicts the effect of inhibitor concentration of truncated ligands Trunc. 1–30 (●), Trnc.2–30 (■) and Trnc.3–30 (▲) on the activity of the Stoffel fragment. The amount of product formed in the presence of varying concentrations of inhibitor was quantitated by phosphorimager and normalized to the amount of product formed in the absence of an inhibitor to obtain the percent product (abscissa).

Stoffel fragment (61 kD) is a truncated form of Taq polymerase that lacks the 5'→3' exonuclease activity and is similar to 67 kD KlenTaq DNA polymerase (67 kD). The polymerase activity of the Stoffel fragment was completely inhibited by the full-length, as well as, the three truncated forms of TQ30. $IC_{50}$ values of the three truncates are Trnc.1–30=2.7 nM, Trnc.2–30=5.9 nM and Trnc.3–30=10.3 nM (FIG. 30). Overall, the three truncated forms of TQ30 are more effective in inhibiting the Stoffel fragment than Taq polymerase (compare FIG. 29 with FIG. 30). The $IC_{50}$ values of these truncates for the inhibition of the Stoffel fragment are an order of magnitude better than those for Taq polymerase. The $IT_{50}$ value for inhibition of the Stoffel fragment by Trnc.2–30 was 38° C. (data not shown). Surprisingly, the TQ21 sequence, which inhibits both Taq and Tth polymerase does not inhibit the Stoffel fragment. This suggests that the binding site of TQ21 on the Stoffel fragment is either partially or completely deleted or has been reorganized upon truncation of the protein.

Truncates of Ligand TQ21 (SEQ ID NO:59)

Figure 31A:
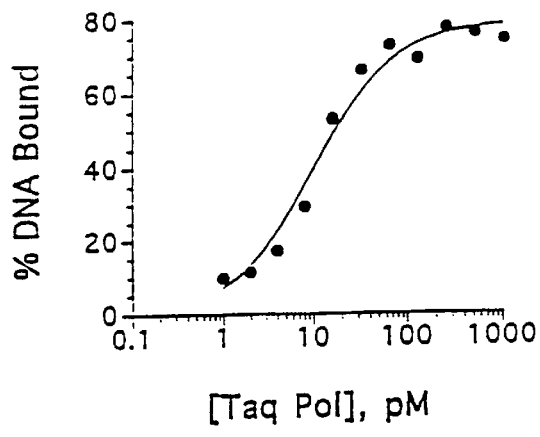
FIGS. 31A–C illustrate the affinity and inhibition characteristics of truncated ligand Trnc.21 (SEQ ID NO:70).
Figure 31B:
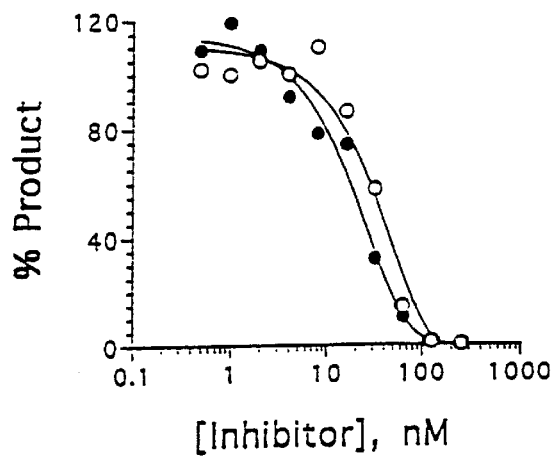
Figure 31C:
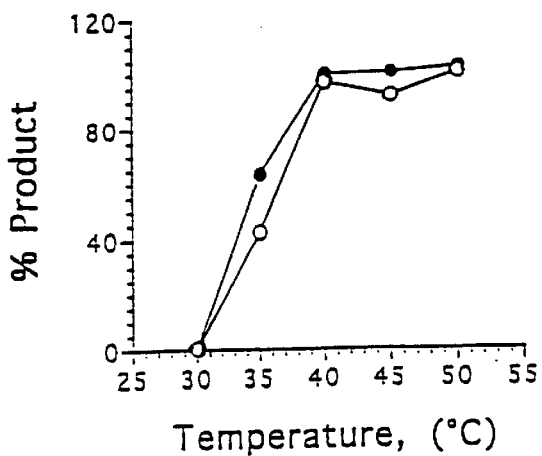

Unlike the Family I ligands, such as TQ30, the 30-nucleotide variable region of the Family II ligand, TQ21, does not inhibit either Taq or Tth polymerase (data not shown), indicating that the additional nucleotides from fixed regions are required for inhibition. Deletion analysis of the full-length TQ21 sequence led to the identification of a 51-mer sequence (Trnc.21 (SEQ ID NO:70) (Table 10)) that retained the ability to inhibit both Taq and Tth polymerases. In addition to the entire 30-nucleotide random region, the Trnc.21 sequence contained 9 and 12 nucleotides from the 5' and 3' fixed regions, respectively (Table 10). In contrast, to the TQ30 truncates, which showed decreased affinity for Taq polymerase, Trnc.21 showed increased affinity; the $K_d$ of Trnc.21 for binding to Taq polymerase is 9 pM (FIG. 31A), about 4-fold higher affinity than the full-length sequence. The $IC_{50}$ value of Trnc.21 for inhibition of Taq polymerase is 21 nM (FIG. 3 1B), about 3-fold lower than the value for the full-length sequence. The calculated $IT_{50}$ values for Taq polymerase and Tth polymerase are 34° C. and 35.6° C., respectively (FIG. 31C). The hairpin extension assays were carried out between the temperatures of 35 and 50° C. for 1 hour with 250 mM Trnc.21. Thus, based on the affinity and the values of $IC_{50}$ and $IT_{50}$, the truncated form of TQ21 is a better inhibitor than the full-length sequence. Similar to the full-length sequence, Trnc.21 did not inhibit the activity of the Stoffel fragment.

Truncates of Ligands 6 (TQH6 (SEQ ID NO:78)), 22 (TQH22 (SEQ ID NO:81)) and 28 (TQH28 (SEQ ID NO:87))

Figure 32:
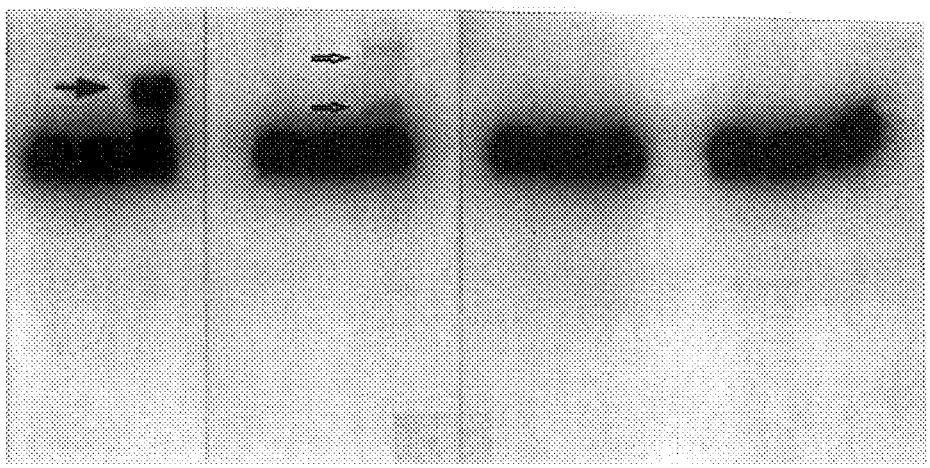
FIG. 32 illustrates the effect of Taq polymerase on truncated forms of ligands 6 (SEQ ID NO:78), 22 (SEQ ID NO:81) and 28 (SEQ ID NO:87). 5'-end labeled ligands were used in this experiment. For each ligand lanes 1 and 4 are the controls, wherein incubation was carried out in buffer only. Lanes 2 and 5 show the results after incubation with Taq polymerase and lanes 3 and 6 shows the outcome after incubation with Taq polymerase and all four dNTPs. Arrows indicate the extension products of ligands.

Functional truncates were identified by systematic deletion analysis of the full-length sequences. The truncates contained 9 and 12 nucleotides from the 5' and 3' fixed regions, respectively, linked to the variable region, resulting in 50 or 51 nucleotide sequences. Hence, in each truncate the variable region is flanked by 5'-TGGCGGAGC- and -TCTTGTGTATGA-3'. The truncated ligands were not cleaved by the 5'→3' exonuclease activity when incubated with Taq polymerase (FIG. 32), which suggests that upon truncation, either cleavage sites were eliminated or ligands adapt a structure not recognized by the exonuclease activity.

The affinities of truncated ligands TQH6-Tr and TQH28-Tr to Taq polymerase were measured in the Tris and Tricine buffers. The $K_d$ values of the full-length and truncated ligands in the two buffers at 55° C. are set forth in Table 9. The affinity of ligand 6 (TQH6) decreased by 3–4 fold in both buffers upon truncation and the affinity of ligand 28 (TQH28) decreased by 3–4 fold in the Tris buffer. Overall, the moderate decrease in affinity upon truncation indicates that deleted nucleotides contribute some level of binding energy in the full-length sequences, presumably through non-specific interaction.

As set forth in Table 12, the $IT_{50}$ values of truncated ligands TQH6-Tr, TQH22-Tr and TQH28-Tr were decreased by 5–9° C. upon truncation. Comparison of $TC_{50}$ values measured in Tricine buffer at 45° C. for truncated and full-length ligands reveals that $TC_{50}$ values (the concentration at which 50% of the input hairpin substrate is converted to fully extended product at a given temperature) increased by 2–3 fold upon truncation (Table 12).

Overall, the results of this analysis indicate that truncated ligands are not cleaved by the 5'→3' exonuclease activity of Taq polymerase. Moreover, they exhibit high affinity-binding to Taq polymerase and inhibit the polymerase activity with at higher temperatures. These characteristics of truncated ligands are desirable for PCR applications to control nonspecific amplifications.

Truncates of Nucleic Acid Ligands to TZ05 Polymerase

Truncated ligands that inhibit the polymerase activity of TZ05 polymerase were identified by systematic deletion analysis of the full-length sequences. These ligands lack the majority of the two fixed regions and are 51 nucleotides long (FIG. 33). The truncates require 9 and 12 nucleotides from the 5' and 3' fixed regions, respectively, for effective inhibition of polymerase activity.

Table 13 compares the $K_d$ values of truncated ligands to TZ1, TZ13 and TZ36 to those of the respective full-length ligand. It can be seen that the affinities of these ligands were not drastically changed upon truncation down to 51 nucleotides. The binding reactions depicted in Table 13 were performed in TZ05 buffer at 55° C. This result indicates that the deleted nucleotides in the two fixed regions are not critical for ligand binding to the polymerase. In addition to the 5 1 nucleotide truncates, the 30 nucleotide truncates containing just the variable regions of the full-length ligands were also tested for their ability to inhibit the polymerase (FIG. 33).

The $IT_{50}$ values of the 51 and 30 nucleotide truncates of ligands TZ1, TZ13 and TZ36 are set forth in Table 14. To calculate $IT_{50}$ values the hairpin extension assays were carried out as described in Example 2. As can be seen in Table 14, all three of the 51 nucleotide truncates inhibited polymerase activity above 40° C. The $IT_{50}$ values of TZ13 and TZ36 were decreased by 7.5° C. and 4° C. upon truncation, whereas the $IT_{50}$ value of TZ1 did not change upon truncation. Overall, the $IT_{50}$ values and affinities of the 51 nucleotide truncates make them attractive candidates for PCR applications.

Figure 34A:
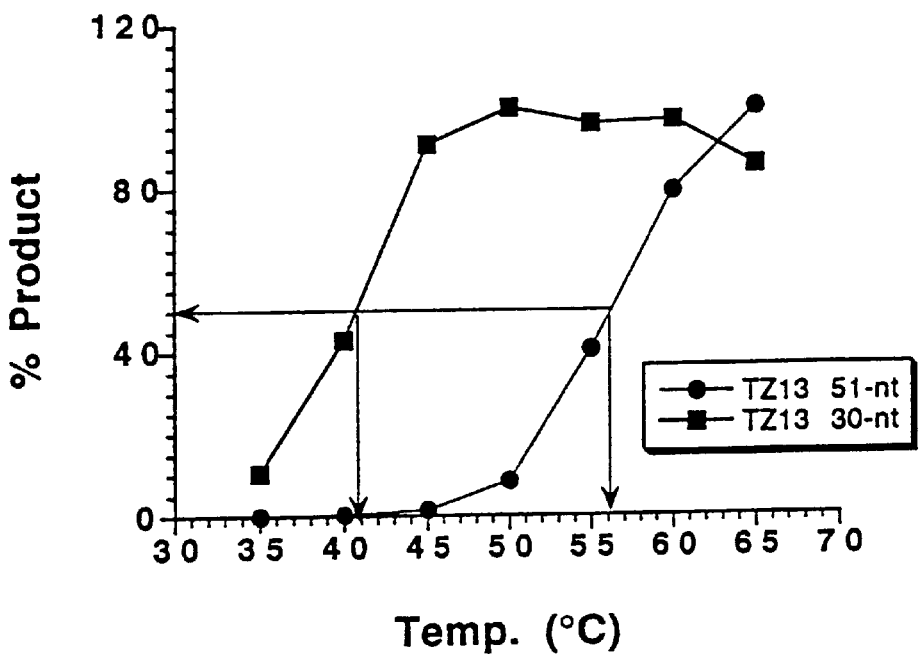
FIGS. 34A and B illustrate the effect of temperature on inhibition of TZ05 polymerase by different truncates of ligand TZ13 (SEQ ID NO:89). The extension product of the hairpin substrate was quantified by phosphorimager and normalized to the product formed in the absence of an inhibitor at the same temperature to obtain the percent of product. Temperature at which 50% of the product was formed is the $IT_{50}$ value of an aptamer.
Figure 34B:
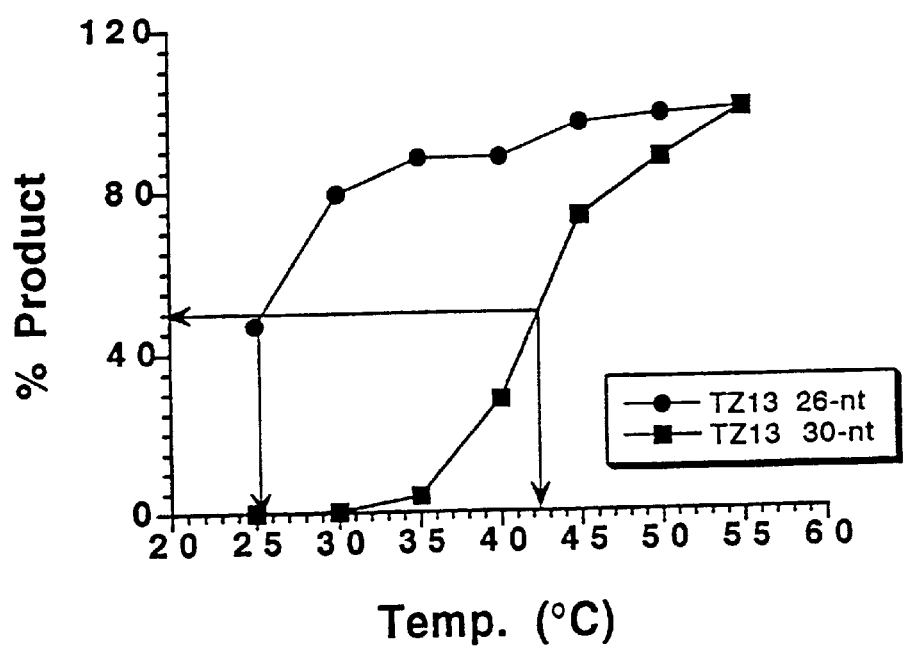

In the case of ligand TZ 13, further truncation down to 30 nucleotides decreased the affinity by approximately 5-fold ($K_d$=145 pM). The affinity of this truncate parallels with its low $IT_{50}$ value (42° C.). Deletion of four additional nucleotides from the 3' end of the 30 nucleotide truncate of TZ13 decreased the $IT_{50}$value by 17° C. (FIG. 34). Interestingly, 30 nucleotide truncates of TZ1 and TZ13 exhibited $IT_{50}$ values above 40° C., whereas the 30 nucleotide truncate of TZ36 did not. Hence, 30 nucleotide truncates of TZ1 and TZ13 with $IT_{50}$ values >40° C. may also be useful in PCR applications.

Figure 35:
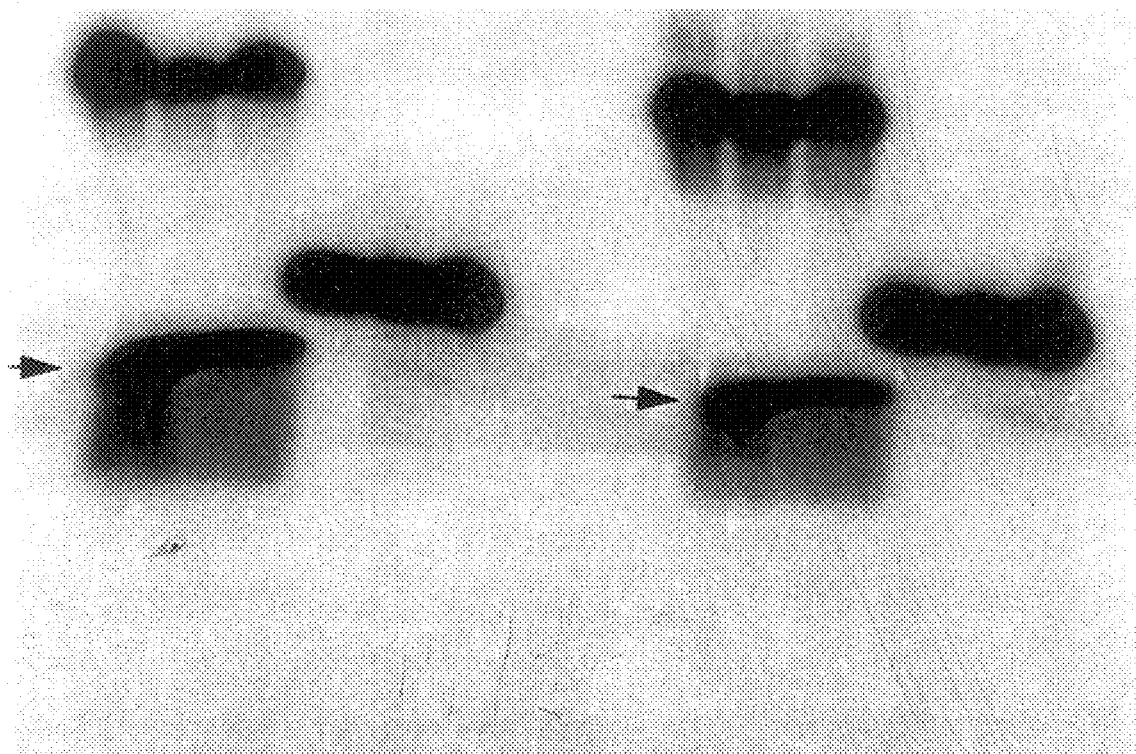
FIG. 35 illustrates the effect of TZ05 polymerase on 5' end-labeled truncated ligands of TZ1 and TZ13. Lanes 1–3 and lanes 4–6 show the results obtained with the 51-nucleotide and 30 nucleotide truncate of each respective ligand. Reactions in lanes 1 and 4 did not have dNTPs, whereas those in lanes 2, 3, 5 and 6 contained dNTPs. Arrows indicate the cleavage products resulting from exonuclease cleavage.

The 51 nucleotide truncates of these ligands retain desirable values for affinity ($K_d$) and polymerase inhibition ($IT_{50}$). As shown in FIG. 35, the 51 nucleotide truncates were cleaved by the exonuclease activity of the polymerase. Incubation of the 30 nucleotide truncates with TZ05 polymerase, however, did not result in cleavage, suggesting that the cleavage site on the 51 nucleotide truncate is likely to be within the nine nucleotide span of the 5'-fixed region. Although the 30 nucleotide truncate was not cleaved by the enzyme, its $K_d$ value (145 pM) and $IT_{50}$ value (42° C.) may not be attractive for certain PCR applications in which polymerase activation is desirable at temperatures close to 50° C. In an attempt to block the cleavage of the 51 nucleotide truncates, phosphorothioate linkages were introduced. It was found that the truncates containing phosphorothioate linkages in the first eight nucleotides of their 5' ends (FIG. 33) were resistant to exonuclease cleavage. The $IT_{50}$ values of truncates with phosphorothioate linkages were comparable with those that lack phosphorothioates, suggesting that the introduction of eight phosphorothioate linkages in these truncate did not affect their ability to inhibit TZ05 polymerase.

Dimeric Forms of Truncates

Multimerization of ligands increases effective local concentration, resulting in a longer resident time with the target (avidity). Based on its moderate affinity for Taq polymerase Trnc.2–30 was selected for synthesis of a homodimer (Table 10). Homodimer (D.30—D.30) (SEQ ID NO:71) (Table 10) of Trnc.2–30 (SEQ ID NO:68) was synthesized in tail-to-tail orientation (linked at 3' ends) using the symmetric dimer CPG as the support in solid phase chemical synthesis using standard methods.

Figure 36A:
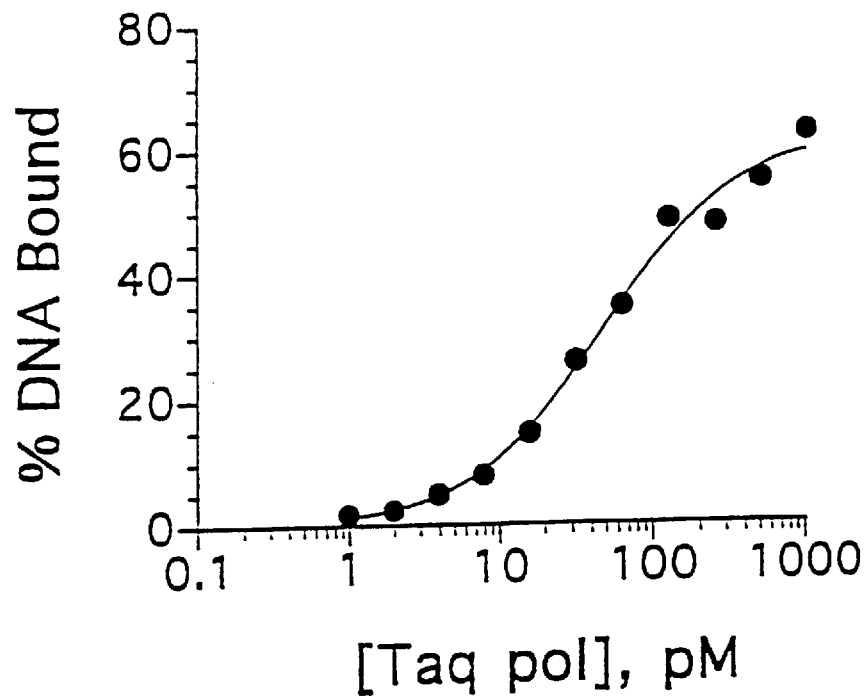
FIG. 36A depicts a binding curve for homodimer (D.30–D.30) to Taq polymerase ($K_d$=47.5±5 pM).
Figure 36B:
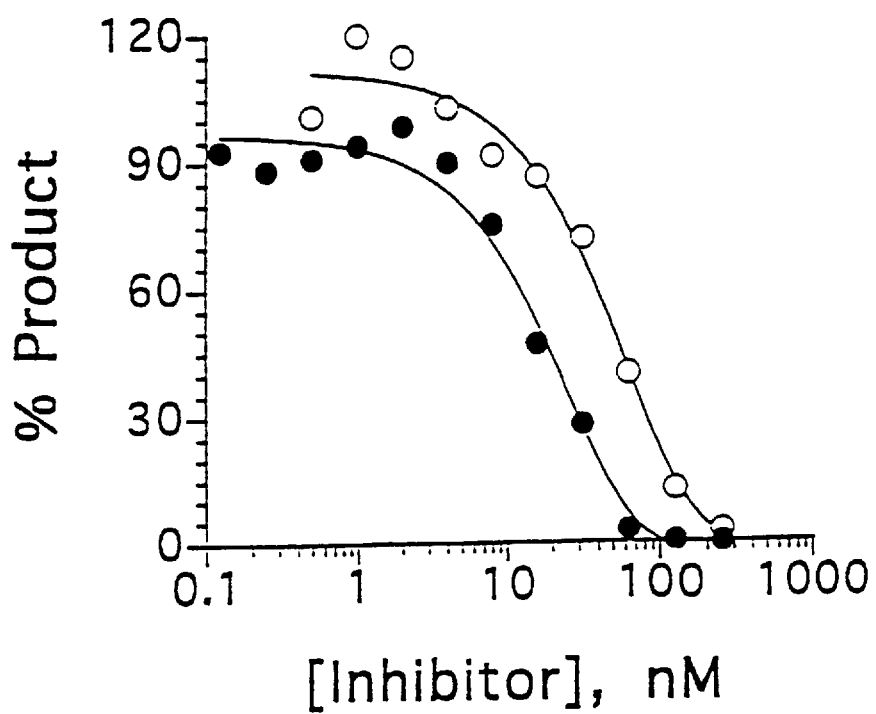
FIG. 36B illustrates the effect of dimeric (■) and monomeric (○) ligand concentrations on the activity of Taq polymerase. The $IC_{50}$ value of Trnc.2–30 (monomer) is 48 nM, whereas that of D.30–D.30 (dimer) is 14 nM.

The affinity of D.30—D.30 dimer for binding to Taq polymerase is 40 pM (FIG. 36A), about 75-fold higher than its monomeric form. The $IC_{50}$ value of the homodimer is 14 nM, about 3.5-fold lower than the monomeric form (FIG. 36B). Thus, the dimerization of the truncated TQ30 produced a more effective inhibitor for Taq polymerase.

Two heterodimeric sequences in which the two monomeric truncates, Trnc.2–30 and Trnc-21 (Table 10), were joined by a linker containing 3 thymines were also prepared. In D.21–D.30 (SEQ ID NO:72) the Trnc-21 sequence is placed at the 5' end of the molecule, whereas in D.30–D.21 (SEQ ID NO:73) it occupies the 3' end of the molecule. Unlike the full-length TQ30, its truncated forms did not inhibit Tth polymerases. Trnc-2, on the other hand, inhibited both Taq and Tth polymerases, but not the Stoffel fragment. Assuming that the monomeric units are able to function independently, after being thethered into a single sequence, the combination of the two truncated ligands would provide a single sequence that could inhibit all three polymerases. At the lowest inhibitor concentration (62.5 nM) the inhibitory effect of the two heterodimers on Taq polymerase is higher than the two monomers. The effect of heterodimers on Tth polymerase is identical to that of the Trnc-21 monomer. The Stoffel fragment could not completely extend the hairpin template in the presence of the two heterodimers. In contrast, partially extended products were less abundant in the presence of the monomeric Trnc.2–30 sequence. The lack of the complete extension of the hairpin template suggests that the heterodimers do suppress the activity of the Stoffel fragment.

Figure 37A:
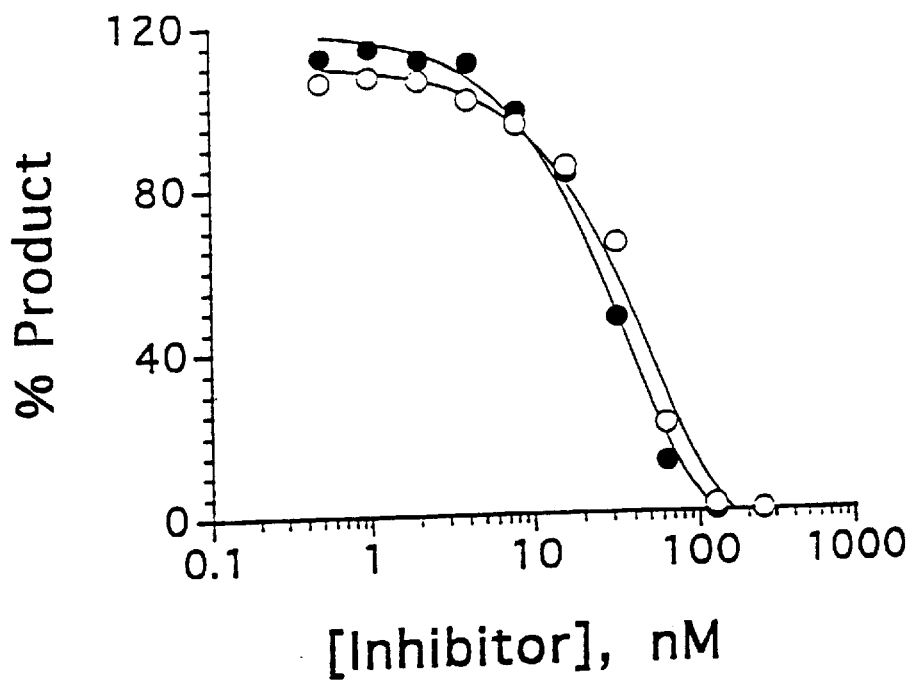
FIG. 37A illustrates the effect of D.21–D.30 concentration on the activity of Taq polymerase (●) and Tth polymerase (○). $IC_{50}$ values for the inhibition of these two polymerases are approximately 30 nM.
Figure 37B:
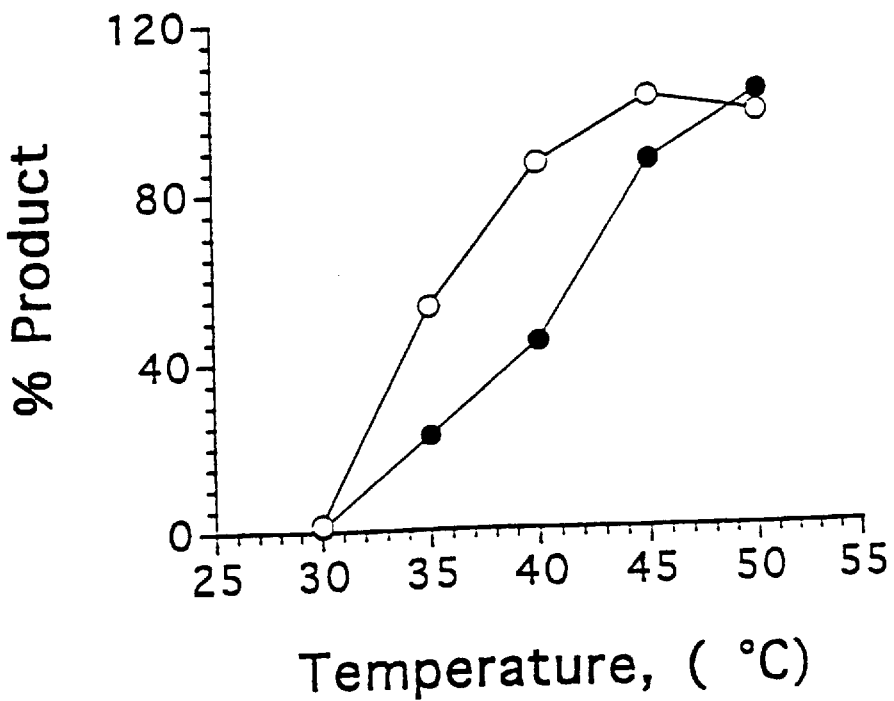
FIG. 37B illustrates the effect of temperature on the inhibition of Taq polymerase (■) and Tth polymerase (○) by heterodimer D.21–D.30. The $IT_{50}$ value for Taq polymerase is 41° C., whereas that for Tth polymerase is 34.5° C.

The heterodimer D.21–D.30 has an $IC_{50}$ value of approximately 30 nM for the inihibition of the Taq and Tth polymerases (FIG. 37A). The $IT_{50}$ values for the inhibition of the Taq and Tth polymerase are 41 and 34.5° C., respectively (FIG. 37B). D.21–D.30 inhibits the Stoffel fragment with an $IC_{50}$ value of 15.5 nM and an $IT_{50}$ value of 38° C. (data not shown). The $K_d$ of ligand D.21–D.30 heterodimer for binding to Taq polymerase is similar to that of the Trnc-21 (10 pM), suggesting that the protein preferentially binds to the sequence motif with high-affinity binding.

The positioning of the two monomeric units in the dimer seems to have no overall effect on the inhibition on any of the three polymerases. The two different monomeric units did not show adverse effect when they were combined into a dimer. As expected, the heterodimers showed the ability to inhibit all three polymerases quite effectively, indicating that by and large, functions of monomeric units in heterodimers are mutually exclusive.

Figure 38:
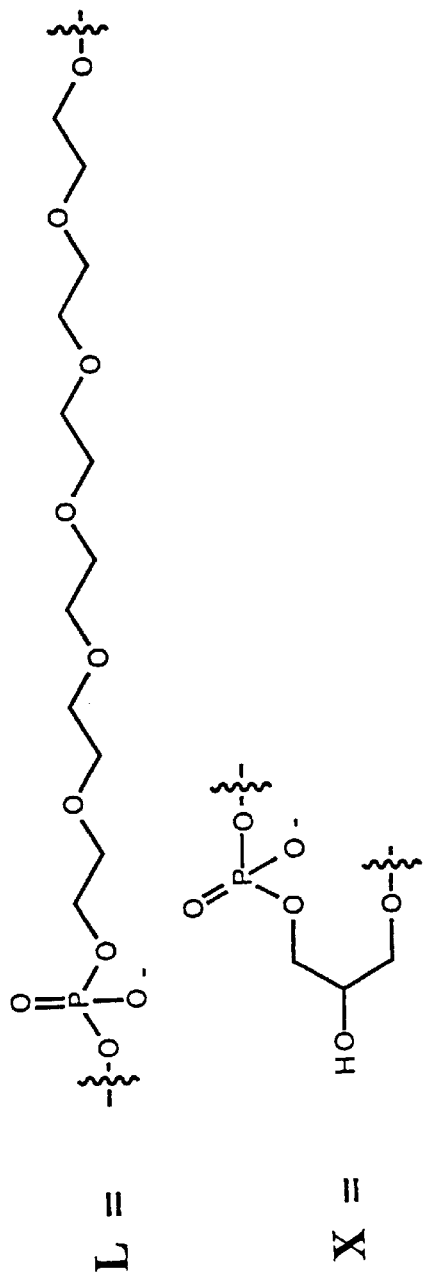
FIG. 38 depicts the sequences and linker structures of three dimers of the TZ13 (SEQ ID NO:89) nucleic acid ligand.
Figure 39A:
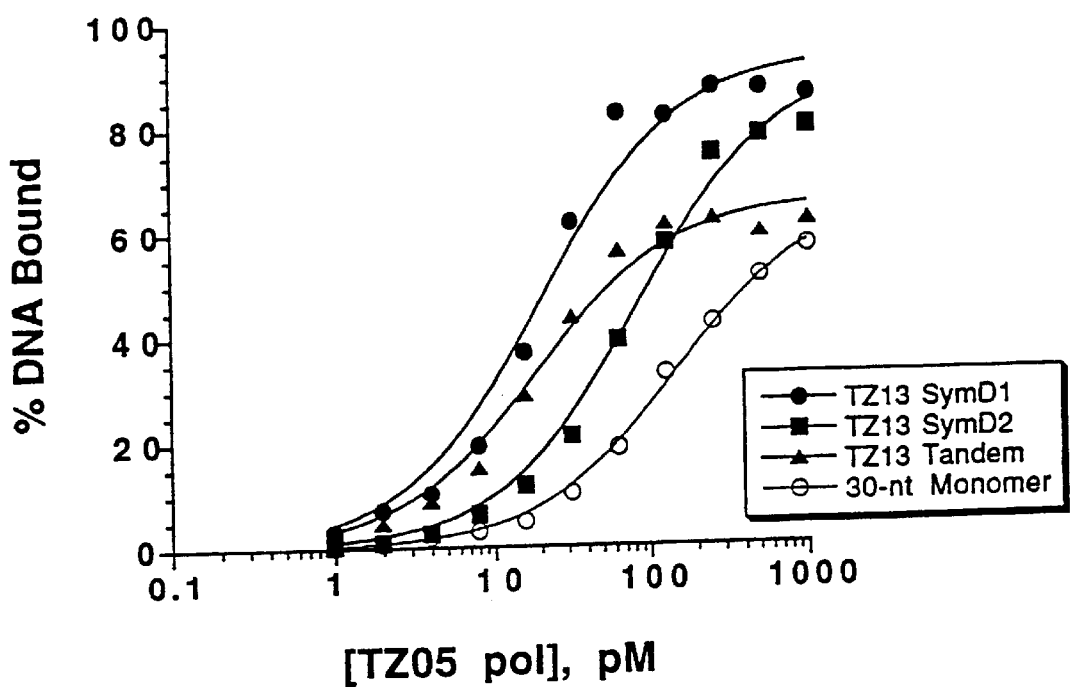
FIGS. 39A and B depict the binding and inhibition analysis of the TZ13 (SEQ ID NO:89) monomer and the three dimers set forth in FIG. 38.
Figure 39B:
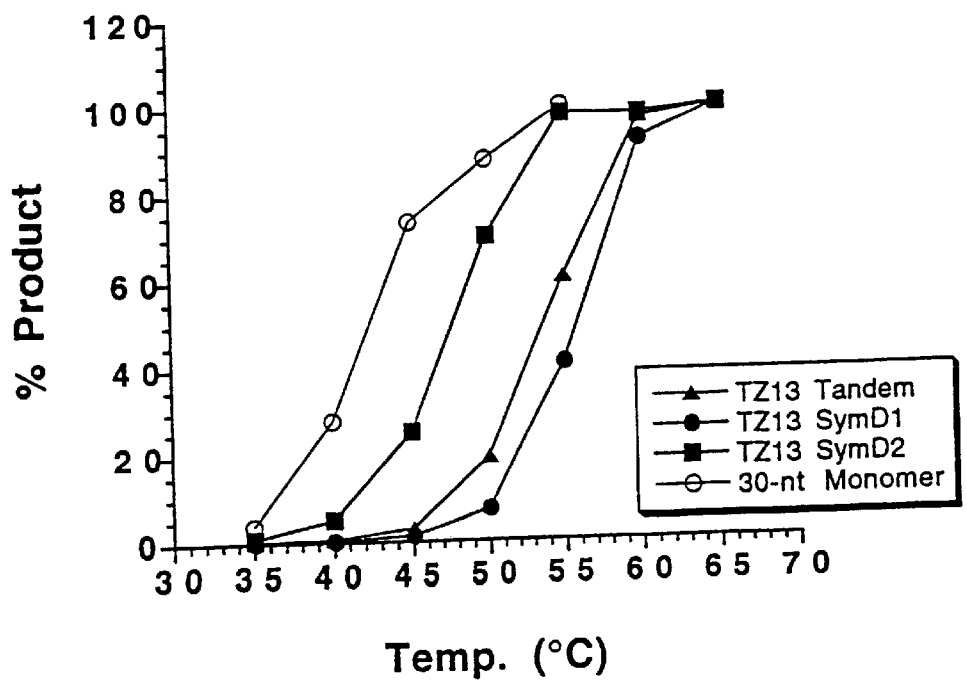
Figure 40A:
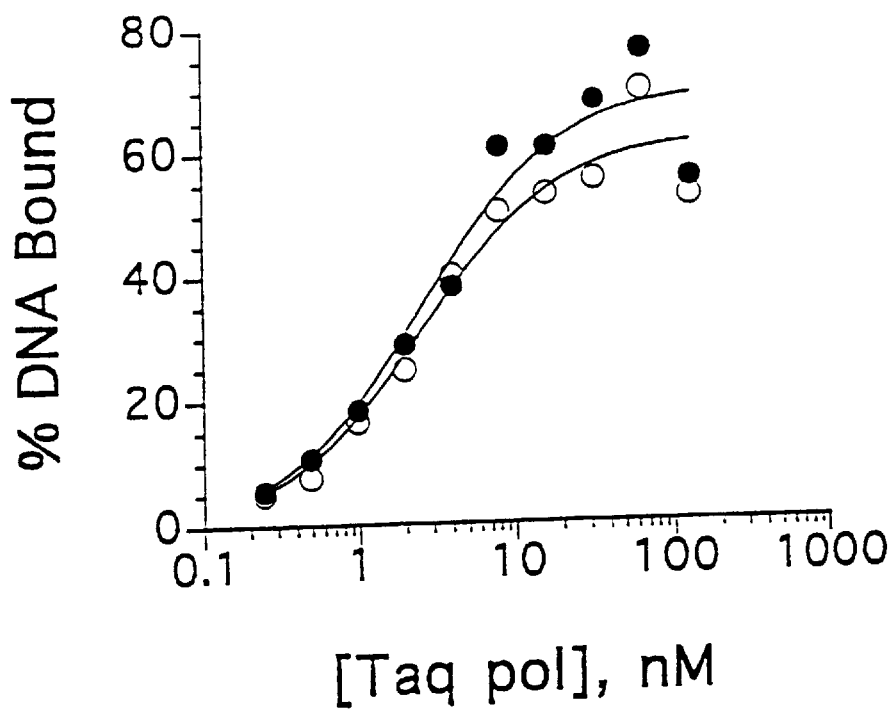
FIG. 40A depicts the nitrocellulose filter binding analysis of Trnc.21 in the presence of 1 mM dNTPs. Closed circles (■) indicate the binding in the absence of hairpin DNA template, whereas open circles (○) indicate the binding in the presence of 250 nM hairpin DNA template. The calculated $K_d$ values under these conditions are approximately 2.5 nM.
Figure 40B:
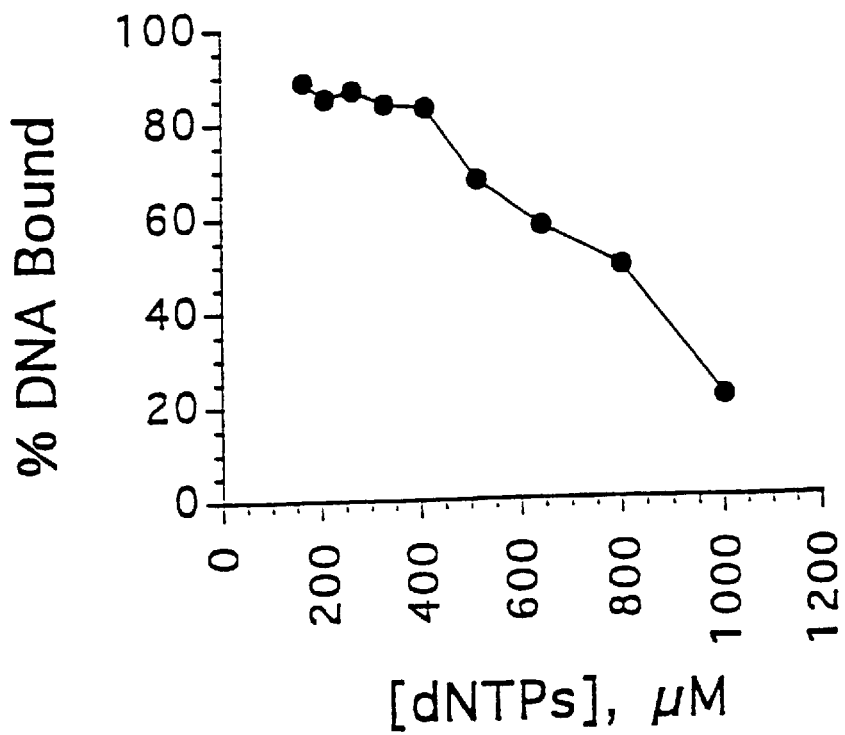
FIG. 40B illustrates the effect of dNTP concentration on the binding of Trnc.21 to Taq polymerase. In this experiment binding of the radiolabeled Trnc.21 to 1 nM Taq polymerase was monitored in the presence of varying concentration of dNTPs.

The 30 nucleotide truncate of nucleic acid ligand TZ13 (SEQ ID NO:89) was synthesized as a dimer in three different forms (FIG. 38). TZ13-Tandem (SEQ ID NO:116) was obtained by placing two units of the 30 nucleotide truncate in a tandem fashion, linked by three thymine units. TZ13-Symmetric dimer-1 (SEQ ID NO:117) was synthesized by linking the 3' ends of the two ligands by a glycerol moiety. In the third dimer, TZ13-Symmetric dimer-2 (SEQ ID NO: 118), the two monomeric units were linked at their 3' ends through a glycerol moiety, but a linker consisting of six ethylene glycol units was placed between the 3' end and the glycerol moiety. As shown in FIG. 39A and Table 15, all three dimers show higher affinity ($K_d$ values between 18–80 pM) for binding to TZ05 polymerase than the monomeric ligand whose $K_d$ value was 145 pM. It is expected that avidity plays a role in the interactions of the dimers with the polymerase and thereby increases the affinity. The three dimer constructs of the same monomer display different affinities. Symmetric dimer-1 without the linker showed the highest affinity, whereas Symmetric dimer-2 with the ethylene glycol linker has the lowest affinity of the three dimers. The observed affinities of the three dimers correlate well with their potency of inhibition as measured by $IT_{50}$ values (FIG. 39B and Table 15).

The following examples are provided to explain and illustrate the present invention and are not intended to be limiting of the invention.

EXAMPLES

Example 1

Experimental Procedures

A. Materials and Methods

Recombinant Taq polymerase (rTaq; Mr 94 kDa) suspended in a buffer consisting of 100 mM KCl, 20 mM Tris-HCl (pH 8.0), 0.1 mM EDTA, 50% glycerol (v/v) and 0.2% Tween 20; recombinant Tth polymerase (rTth; Mr 94 kDa) suspended in a buffer consisting of 50 mM Bicine-KOH (pH 8.3), 90 mM KCl and 50% glycerol (v/v); and Thermus species Z05 (TZ05 pol) were purchased from Roche Molecular Systems, Inc. (Alameda, Calif.). Taq, Tth and UlTma DNA polymerases were obtained from Perkin Elmer. Ultma polymerase is a deleted form of Tma polymerase that lacks the wild type 5'→3' exonuclease activity. Tli and Tfl DNA polymerases were purchased from Promega. Tbr polymerase (Thermalase Tbr) was obtained from Amresco Inc. Symmetrical branching 3'—3' linking CPG and C-6 Thiolmodifier phosphoramidites were obtained from Clontech (Palo Alto, Calif.). ULTRALINK™ Iodoacetyl beads were purchased from Pierce Chemicals (Rockford, Ill.). Enzymes used in radiolabeling of DNA were obtained from Boehringer Mannheim (Indianapolis, Ind.). All other reagents and chemicals were analytical grade and purchased from standard commercial sources.

Preparation of Oligonucleotides. Oligonucleotides were synthesized by standard solid phase cyanoethyl phosphoramidite chemistry and purified by either denaturing polyacrylamide gel electrophoresis to size homogeneity or reverse phase high pressure liquid chromatography. The symmetrical homodimer was synthesized with Symmetrical Branching 3'—3' linking CPG. DNA concentrations were based on 33 µg/mL=1 $A_{260}$ Unit.

Preparation of Affinity Beads. Twenty five nanomoles of either ligand TQ21 (SEQ ID NO:59) or TQ30 (SEQ ID NO:50) (Table 3) containing a thiol group at the 5' end was deprotected with $AgNO_3$ and dithiothreitol (DTT) according to manufacturer's instructions. Excess DTT was removed by four sequential extractions with equal volumes of ethyl acetate. The deprotected ligand was then mixed with 500 µL of ULTRALINK™ iodoacetyl beads that had been washed two times in a buffer consisting of 50 mM Tris-HCl (pH 8.3) and 5 mM EDTA. The reaction mixture was incubated at room temperature for 2 hours on a rotating platform. Unreacted sites on the iodoacetyl beads were capped by reacting the mixture with 50 µL of a 0.5 M cysteine solution in the same buffer for 15 minutes. Control beads were prepared by reacting 500 µL of iodoacetyl beads with 500 µL of 0.5 M cysteine. After the reaction, the beads were washed five times with 500 µL of a PCR buffer consisting of 75 µM heparin, 12.5 mM $MgCl_2$, 50 mM KCl and 10 mM Tris-HCl (pH 8.3).

B. SELEX

The SELEX procedure has been described in detail in U.S. Pat. No. 5,270,163, which is incorporated herein by reference in its entirety. The SELEX experiments were performed at room temperature and at elevated temperatures using the template and primers shown in Table 1.

Room Temperature. The selection on Taq polymerase was carried out at room temperature in a buffer consisting of 10 mM Tris-HCl (pH 8.3; at 22° C.), 50 mM KCl and 2.5 mM $MgCl_2$ (Taq binding buffer). The selection on Tth polymerase was carried out in a buffer containing 50 mM Bicine-KOH (pH 8.3; at 25° C.), 90 mM KCl and 3.5 mM $Mn(OAc)_2$ (Tth binding buffer).

Each SELEX experiment was initiated with 5 nmoles of synthetic, gel-purified random sequence pool single stranded DNA (ssDNA) consisting of 30 nucleotide randomized region, flanked by 5' and 3' regions of fixed structure (Table 1). In a typical round of selection, ssDNA suspended in the appropriate binding buffer was heated to 90° C. for 3 minutes, chilled on ice, and then brought to room temperature. Once equilibrated at room temperature, the DNA was incubated for 15 minutes with the appropriate target polymerase in the presence of 2 nmoles of tRNA as a competitor and 0.01% human serum albumin (hSA). Polymerase-DNA complexes were separated from unbound DNA by nitrocellulose filtration through a prewet nitrocellulose filter (0.45 µM, Millipore) under suction. The filter was immediately washed with 20 mL of the binding buffer, 20 mL of 0.5 M urea in the binding buffer, and 0.5 M urea in water. Filter retained DNA was eluted and isolated by ethanol precipitation in the presence of carrier tRNA (5 µg).

The isolated DNA was amplified by PCR with Primer Set I (Table 1). One of the primer strands contained three contiguous biotins at the 5' end. The unbiotinylated strand of the resulting duplex DNA was isolated by gel electrophoresis under denaturing conditions (Pagratis (1996) Nucleic Acid Res. 24:3645–3646) and used for the next round of selection. In subsequent rounds, prior to incubating with the target polymerase, DNA pools were passed through nitrocellulose filters (counter selection) to remove DNA sequences that bind to the nitrocellulose filter. The number of picomoles of target polymerase was gradually decreased during the course of SELEX to increase the selective pressure for sequences with high affinity binding. The amount of DNA in each selection was kept at least five-fold higher than the amount of protein to ensure competition for high affinity binding DNA sequences.

The progress of SELEX was monitored by nitrocellulose filter binding analysis of enriched pools. The enriched pools that showed the highest affinity binding were PCR amplified with Primer Set II to incorporate BamHI and EcoRI restriction sites at the termini of the resulting duplex DNA. This DNA was gel purified and digested with BamHI and EcoRI and cloned into plasmid pUC 18 vector previously digested with the same enzymes using standard techniques. (Sambrook et al. (1989) in *Molecular Cloning: A laboratory Manual*, 2nd ed., Part 3, pC.1, Cold Spring Harbor Laboratory Press, Cold Spring Harbor, N.Y.). Clones were isolated and sequenced by standard dideoxy sequencing technique (Sequenase kit from U.S. Biochemical, Cleveland, Ohio).

High Temperature SELEX. Affinity selection at high temperature on Taq polymerase was performed in a binding buffer consisting of 50 mM Tricine-KOH (pH 8.0), 50 mM KOAc (pH 7.5), 2.5 mM Mg(OAc)$_2$ and 10% glycerol at 55° C. (Tricine buffer). The starting library for this selection was the 12th round ssDNA library derived from the affinity selection performed at room temperature in the binding buffer consisting of 10 mM Tris-HCl (pH 8.3), 50 mm KCl and 2.5 MM MgCl$_2$ (Table 3 (Dang and Jayasena (1996) J. Mol. Biol. 264:268). The upper case letters indicate the 30 nucleotitde (nt) random region that is flanked by 5'-TTCTCGGTTGGTTCTCTGGCGGAGC- and -TCTTGTGTATGATTCGCTTTTCCC-3' fixed sequences. Underlined regions in Family I sequences are complementary for base pairing). The latter library was enriched from a synthetic random sequence ssDNA library using the sequence 5'-TTCTCGGTTGGTCTCTGGCGGAGC-[N]$_{30}$-TCTTGTGTATGATTCG CTTTTCCC-3' (SEQ ID NO: 1; Table 1).

The high temperature affinity selection was initiated with 5 nmoles of the 12th round ssDNA library suspended in the Tricine binding buffer. This suspension was heated to 95° C. for 3 minutes, chilled on ice for 5 minutes and brought to 55° C. Two nmoles of tRNA (used as a competitor), 0.01% (w/v; final concentration) of hSA (human serum albumin) and Taq polymerase (125 nM) were added to the DNA suspension and incubated for 15 minutes at 55° C. Polymerase-bound DNA was recovered by a quick filtration through a prewet nitrocelluose filter (0.45 $\mu$m; Millipore) under suction. The filter was immediately washed with 20 mL volumes of binding buffer, followed by an equal volume of 0.5 M urea in the binding buffer. Both wash buffers were pre-warmed to 60° C. prior to use. Filter-retained DNA was eluted and isolated by ethanol precipitation in the presence of 5 $\mu$g of tRNA used as a carrier. The isolated DNA was amplified by PCR using Primer Set I (Table 1) as described above.

To ensure the enrichment of high affinity binding DNA sequences to Taq pol, the selective pressure was gradually increased during the course of selection. This was accomplished by gradual decrease in the amount of both Taq polymerase and the DNA used in each round, as well as, stringent washing of the filter-retained DNA. The affinity of enriching libraries was monitored by nitrocellulose filter binding (described below). No significant affinity improvement was noticed after eight rounds of selection. The 8th round library was PCR amplified with Primer Set II (Table 1) as described above. The complexity of the enriched library was analyzed by sequencing the DNA inserts of the transformants by dideoxy sequencing technique (Sequenase kit from USB).

Affinity selection on TZ05 polymerase was performed at 55° C. in a binding buffer consisting of 50 mM Tricine-KOH, 125 mM KOAc, 2.5 mM Mn(OAc)$_2$ and 8% glycerol (TZ05 pol buffer). The binding buffer was prepared by mixing the stock solutions of 1 M Tricine-KOH (pH 8.0), 3 M KOAc (pH 7.5), 25 mM Mn(OAc)$_2$ and 80% glycerol. Two affinity selections were performed under identical conditions, starting with different ssDNA libraries. One selection was initiated with 5 nmoles of synthetic random sequence ssDNA library; 5'-TTCTCGGTTGGTCTCTGGCGGAGC-[N]$_{30}$-TCTTGTGTATGATTCGCTTTT CCC-3' (SEQ ID NO: 1; Table 1). The starting library for the other selection was the 12$^{th}$ round ssDNA library derived from affinity selection performed on Taq polymerase at room temperature (Table 3).

ssDNA libraries suspended in the binding buffer were heated to 95° C. for 3 minutes, chilled on ice for 5 minutes and then brought to 55° C. Two nanomoles of tRNA (used as a competitor), 0.01% (w/v; final concentration) of hSA (human serum albumin) and TZ05 polymerase (125 nM) were added to the DNA suspension and incubated for 15 minutes at 55° C. Polymerase-bound DNA was recovered by a quick filtration through a prewet nitrocelluose filter (0.45 $\mu$m; Millipore) under suction. The filter was immediately washed with 20 mL of binding buffer and 20 mM of 0.5 M urea in the binding buffer. Both wash buffers were pre-warmed to 60° C. prior to use. Filter-retained DNA was eluted and isolated by ethanol precipitation in the presence of 5 $\mu$g of tRNA used as a carrier.

The isolated DNA was amplified by PCR using Primer Set I (Table 1) as described above. Standard PCR amplification was used for the selection initiated with the completely randomized library, whereas mutagenic PCR conditions were used for the selection initiated with the pre-selected library on Taq pol. Mutagenic PCR, which was intended to increase the nucleotide diversity in the resulting PCR products, was carried out as follows. The recovered DNA was first amplified by PCR in 100 $\mu$L volume containing 50 mM KCl, 10 mM Tris-HCl (pH 8.3), 1.1 mM MnCl$_2$, 7 MM MgCl$_2$, 1 mM dCTP, 1 mM dTTP, 0.2 mM dGTP, 0.2 mM ATP and 1 U of Taq polymerase with cycling parameters of 50 seconds at 94° C., 45 seconds at 45° C. and 45 seconds at 72° C. for 5 cycles. Thirteen $\mu$L from the above PCR was used as the template for a new 100 $\mu$L PCR carried out for 5 cycles under the same conditions as described above. The latter step was repeated three more times. Thirteen $\mu$L from the fourth mutagenic PCR was used as the template for 500 $\mu$L PCR to generate the ssDNA pool to be used in the next selection. The unbiotinylated strand of the resulting duplex PCR products separated on a denaturing polyacrylamide gel was isolated and used for the next round of selection.

To ensure the enrichment of high affinity binding DNA sequences to TZ05 pol, the selective pressure was gradually increased during the course of selection. This was accomplished by gradual decrease in the amount of both TZ05 polymerase and the DNA used in each round, as well as, stringent washing of filters. The affinity enrichment was monitored by measuring equilibrium dissociation constants of enriching libraries.

The enriched library was then PCR amplified using Primer Set II (Table 1) as described above. The complexity of the enriched library was analyzed by sequencing the DNA inserts of the transformants by dideoxy sequencing technique (Sequenase kit from USB).

C. Nitrocellulose Filter Binding Assay

Room Temperature. To assess the affinity of oligonucleotide libraries and individual ligands the nitrocellulose filter binding technique was used. Briefly, gel-purified $^{32}$P ss-DNA pools labeled at the 5' end were suspended in the binding buffer, heated to 80° C., chilled on ice and then brought to room temperature. The DNA (5–10 pM) was then incubated for 15 minutes at room temperature with varying amounts of the target polymerase in 50 $\mu$L of the appropriate binding buffer containing 0.1 $\mu$g of tRNA and 0.01% hSA. The DNA concentrations were kept lower than 100 pM to ensure equilibrium in the presence of excess protein concentrations. After 15 minutes the binding reaction mixtures were passed through pre-wet nitrocellulose/cellulose acetate mixed matrix filters (0.45 $\mu$m pore size, Millipore Corporation, Bedford, Mass.) and the filters were immediately washed with 5 mL of binding buffer. The amount of DNA bound to the filters was quantitated by measuring the radioactivity of the filters by liquid scintillation counting. The quantity of DNA bound to filters in the absence of protein was used for background correction. The percentage of input DNA retained on each filter was plotted against the corresponding log of the polymerase concentration (FIGS. 1 and 2). The nonlinear least square method was used to obtain the dissociation constants ($K_d$) of the DNA ligands to the Taq and Tth polymerases, respectively. (Schneider et al (1995) Biochemistry 34:9599; Jellinek et al. (1993) Proc. Natl. Acad. Sci., U.S.A. 90:11227–11231).

Figure 1B:
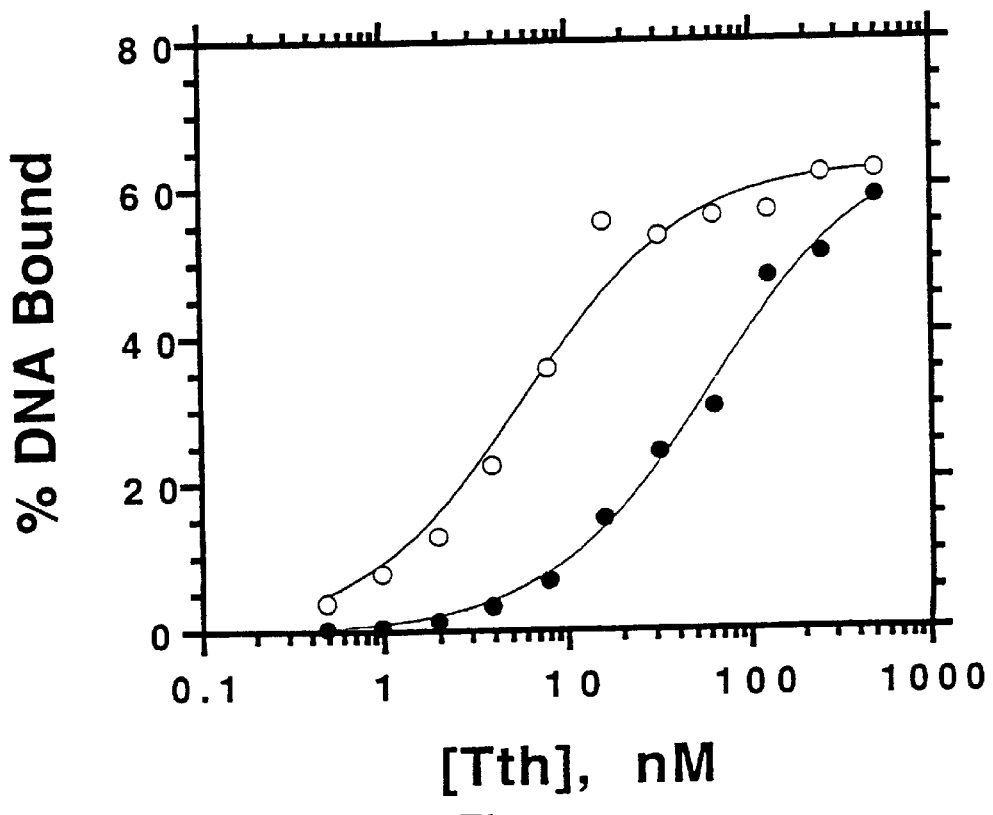
FIG. 1B shows the binding affinities of enriched pools of DNA after 10 rounds of SELEX (○) and the unselected random pool (●) of DNA for the Tth polymerase.

The unselected random sequence pool bind Tth polymerase with an estimated $K_d$ of approximately 70 nM (FIG. 1B, (■)), whereas the $K_d$ of this pool binding to Taq polymerase is approximately 50–100 nM (FIG. 1A, (○)). After 12 rounds of selection, the $K_d$ of binding to Taq polymerase was 3.5 nM (FIG. 1A, (○)). Additional rounds of selection did not result in further improvement of affinity. Thus, the resulting affinity of the enriched pool to Taq polymerase was significantly improved as compared to the unselected random pool. Similar results were obtained with the Tth polymerase where the pool from the 10th round showed a $K_d$ of 5 nM (FIG. 1B, (○)).

Figure 2A:
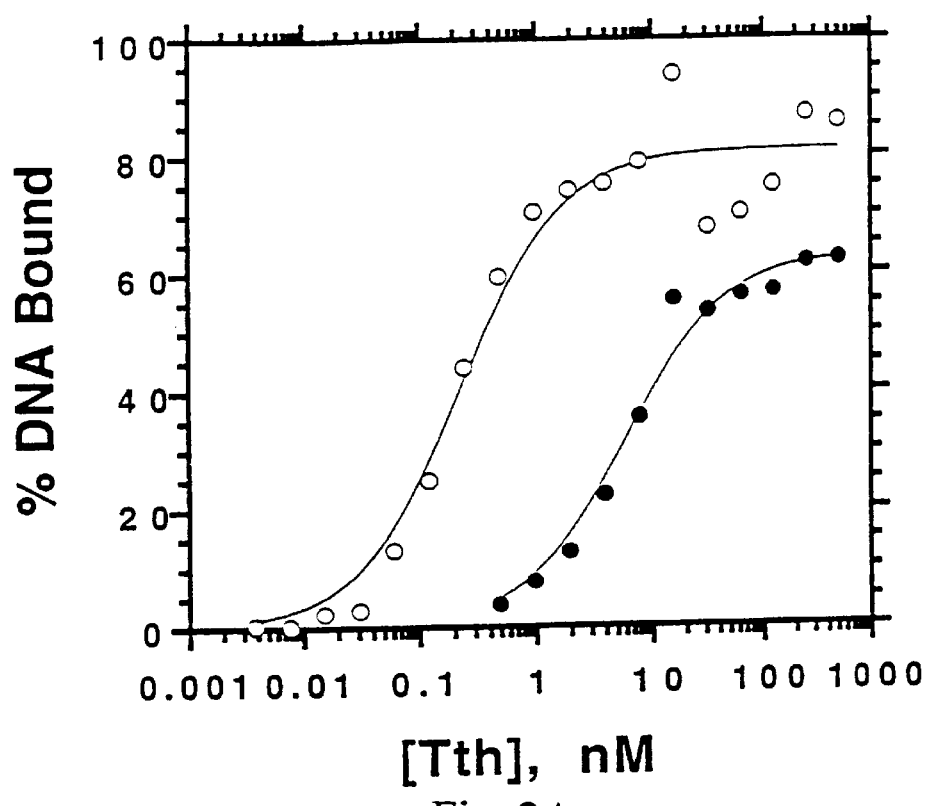
FIG. 2A shows a cross binding analysis of the enriched DNA pool for the Taq polymerase (○) and the enriched DNA pool for the Tth polymerase (●) to the Tth polymerase.
Figure 2B:
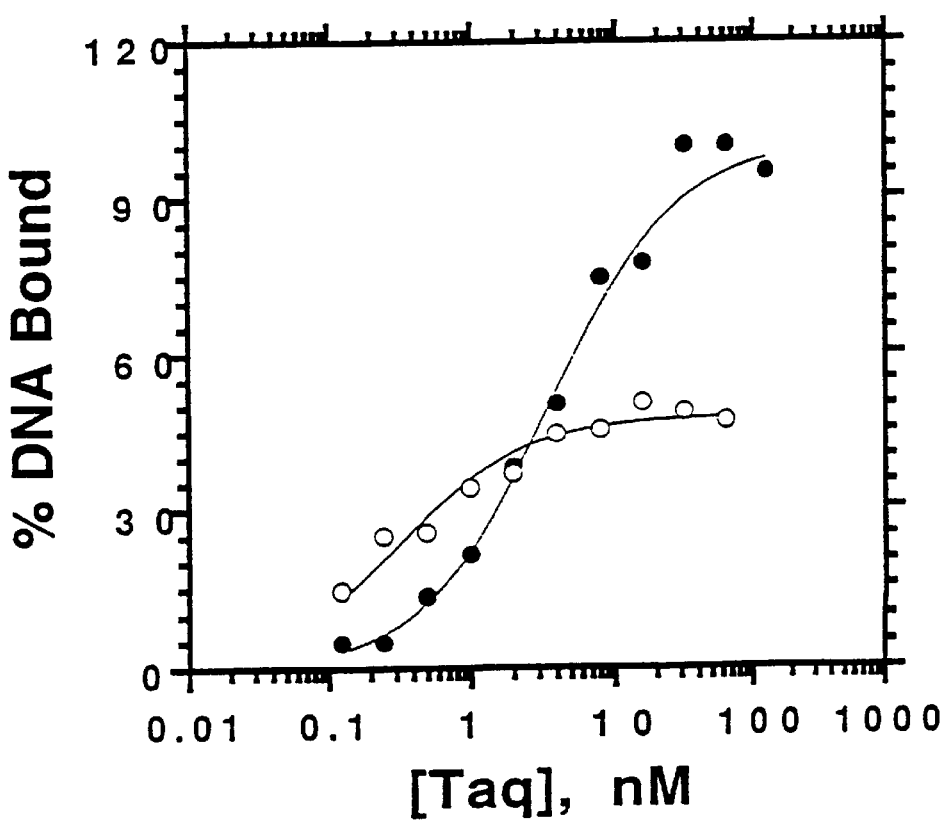
FIG. 2B shows a cross binding analysis of the enriched DNA pool for the Taq polymerase (○) and the enriched DNA pool for the Tth polymerase (●) to the Taq polymerase.

The ssDNA pool selected for Taq polymerase showed very tight binding to Tth polymerase with a $K_d$ of 0.2 nM (FIG. 2A, (○)). This result is not surprising, since the amino acid sequence identity between the two polymerases is approximately 87% (Asakura et al. (1993) J. Ferment. Bioeng. 76:265–269). The pool selected for Tth polymerase bound Taq polymerase in a different manner, with the binding saturating at around the 50% level (FIG. 2B, (○)), suggesting that about one half of the sequences in the pool are not interacting with Taq polymerase. Based on 50% saturation the estimated $K_d$ is 0.3 nM.

The ss-DNA sequences obtained from 10 rounds of selection performed with Tth polymerase are set forth in Table 2. Twenty nine individual clones were sequenced from the Tth polymerase selection (only the variable 30-nt region is shown in Table 2). The sequences were grouped into two families based upon sequence similarity. The ss-DNA sequences obtained from 12 rounds of selection performed with Taq polymerase are set forth in Table 3. Thirty three unique sequences were isolated. The lowercase letters in some of the sequences depict the 5'-fixed sequence and the upper case letters depict the 30 nucleotide random region. The sequences were grouped into three families based on sequence similarity.

High Temperature. Binding affinities of aptamers to Taq and TZ05 polymerase were measured by nitrocellulose filter binding technique at 55° C. Briefly, an end-labeled aptamer was incubated in 50 µL of binding buffer at 55° C. for 15 minutes with varying concentrations of Taq or TZ05 polymerase, respectively. Aptamer-polymerase mixtures were passed through nitrocellulose filters (0.45 µm) prewet with the binding buffer prewarmed to 55° C. Filters were immediately washed with 5 mL of the same buffer heated to 55° C. Two buffers were used for each polymerase: Tris buffer consisting of 50 mM KCl, 2.5 mM MgCl$_2$, 10 mM Tris-HCl (pH 8.3 at 22° C.), 2 ng/µL of tRNA and 0.01% hSA; and Taq buffer consisting of 50 mM Tricine-KOH (pH 8.3), 50 mM KOAc (pH 7.5), 2.5 mM Mg(OAc)$_2$, 10% glycerol, 2 ng/µL of tRNA and 0.01% hSA or TZ05 buffer consisting of 50 mM Tricine-KOH, 125 mM KOAc, 2.5 mM Mn(OAc)$_2$, 8% glycerol 2 ng/µL of tRNA and 0.01% hSA. Equilibrium dissociation constants ($K_d$ values) were calculated by using nonlinear least squares method.

The ss-DNA sequences and their frequency of occurrence obtained after 8 rounds of selection performed with Taq polymerase at 55° C. are set forth in Table 4. Individual sequences are set forth in Table 5. Only the 30-nt random region is shown for each sequence. In the full-length aptamers the random region is flanked by the fixed sequences set forth in Table 1 (SEQ ID NO: 1). As can be seen in Table 4, the complexity of the starting library was significantly reduced; and surprisingly, only six sequences were found. The data in Table 4 was derived from the analysis of 63 readable individual sequences. The aptamers were grouped into two families based on their sequence similarity. Family I aptamers are closely related to Family II sequences of the starting library (compare Tables 3 and 4); these two families bear similar consensus sequence motifs as shown within boxes in each table. All of the Family I sequences present in the starting library (Table 3) had completely disappeared after the selection at high temperature, indicating that their interaction with Taq polymerase was highly temperature sensitive. The single sequence grouped as Family II in the final library represents approximately 10% of the sequences analyzed. This sequence is quite different from the Family I sequences and lacks the consensus motif. Comparison of the sequence complexities of the starting and final libraries indicates that certain sequences in the starting library did not survive the new selection conditions and certain other sequences adapting nucleotide changes sustained new conditions.

During the course of the two selections performed using TZ05 polymerase, enriching libraries were tested for their ability to both bind and inhibit TZ05 polymerase. The selection initiated with the random sequence library showed significant improvement of the affinity and the ability to inhibit TZ05 polymerase after fourteen rounds of selection. Compared to this selection, the enriched library of the selection obtained through mutagenic PCR showed even greater improvement in the ability to inhibit TZ05 polymerase after only 4 rounds of selection. The ss-DNA sequences obtained after 4 rounds of selection followed by PCR under mutagenic conditions at 55° C. are forth in Table 5. The 30-nt random region shown in the table is flanked by the fixed sequences set forth in Table I (SEQ ID NO:1). The number in parenthesis indicate the number of times that sequence was identified. The sequences were grouped into three families based upon sequence similarity. Close inspection reveals that these sequences fall into two broad categories; sequences that are rich in guanine (Families I–II) and sequences that are poor in guanine (Family III). The distribution of guanine in guanine rich sequences is such that they can be folded into intramolecular G-quartet structures. Interestingly, these guanine-rich sequences were not present (most likely they were not detected by cloning due to their low abundance) in the starting library whose complexity is shown in Table 3. The sequences in Family III are not rich in guanine, but carry CGTTTTG consensus motif near the 3' end of the randomized region. A similar consensus motif was identified in the Family II sequences in the starting library (Table 3), suggesting that these two families are related and derived one from the other. The Family I sequences present in the starting library had disappeared upon high temperature selection on TZ05 polymerase. A similar result was observed when the same library was subjected to high temperature affinity selection on Taq polymerase, suggesting that the interaction of Family I aptamers found in the starting library with the two polymerases were temperature sensitive, and did not survive selections at high temperature. Thirteen other sequences with no sequence similarities among themselves or to those shown in Table 5 were also identified and classified as orphan sequences (data not shown).

Example 2

Polymerase Inhibition Assays

The polymerase inhibition assays were performed using the template DNA (DNA-HP;

5'-ATGCCTAAGTTTCGAACGCGGCTAGCCAGCTT TTGCTGGCTAGCCGCGT-3' (SEQ ID NO:6)), end-labeled at the 5' end with T4 polynucleotide kinase and $^{32}$P-γ-ATP and purified by gel electrophoresis under denaturing conditions (FIG. 6). In a representative experimental procedure, either 0.25 pmoles of Taq polymerase (5 U) or 0.125 pmoles (2.5U) of Tth polymerase was mixed with 5 pmoles (250 nM) of the enriched pool, random pool or a specific DNA ligand in the standard PCR buffer (20 μL). Five pmoles (250 nM) of labeled template DNA-HP was added and the mixture was incubated at different temperatures for a given period of time. The reaction was stopped by adding EDTA to a final concentration of 125 mM (5 μL of 0.5 M EDTA). The DNA was resolved on a polyacrylamide gel under denaturing conditions. Gels were visualized by autoradiography and the percent DNA bound was quantitated by phosphoimager. Variations in this general procedure for specific reactions are noted in the Specification.

The order in which the oligonucleotide inhibitors are added to the reaction mixture is irrelevent, as long as, the template is added last. The oligonucleotides require $Mg^{++}$ ions, an essential component of PCR, to function and appear to tolerate many buffer systems.

FIG. 7 illustrates the results of the polymerase activity assays using the enriched pools of DNA. FIGS. 8–10 illustrate the results of the polymerase activity assays using ligands TQ30 (SEQ ID NO:50) and TQ21 (SEQ ID NO:59).

Measurement of $IC_{50}$ Values. $IC_{50}$ values (the concentration of inhibitor required to produce 50% of the product in the assay) were obtained using hairpin extension assays. In a typical inhibition assay, a 20 μL reaction contained either 0.25 (0.04) pmoles of Taq polymerase (5 U) (1 U), 0.125 pmoles of Tth polymerase (2.5 U) or 0.05 pmoles of TZ05 polymerase (1 U), oligonucleotide inhibitor (at varying concentrations), 0.2 M dNTPs in either Tris or Tricine buffer (Taq and Tth pol) or TZ05 buffer (TZ05 pol). Gel purified, 5'-end-labeled hairpin DNA substrate (DNA-HP; 5'-ATGCCTAAGTTTCGAACGCGGCTAG CCAGCTTTTGCTGGCTAGCCGCGT-3' (SEQ ID NO:6)) was then added to a final concentration of 250 nM and the reactions were incubated for a given time at the desired temperature as indicated in the figure legends (30 minutes for TZ05 pol). The reaction was stopped by adding 5 μL of 0.5 M EDTA (pH 8.0) followed by formamide gel loading buffer. Extension products were resolved on 10% polyacrylamide gels under denaturing conditions and quantitated by phosphorimager. The amount of products formed in the presence of inhibitor was normalized to the product formed in the absence of an inhibitor to obtain the percent of product.

Measurements of $IT_{50}$ Values

Hairpin extension reactions were the same as descibed above, except that the inhibitor concentration was 250 nM and the TZ05 polymerase reactions were run at 37° C. Incubation time at each temperature was 1 hour for Taq and Tth pol and 30 minutes for TZ05 pol. The amount of product was quantitated by phosphorimager and normalized to the product formed in the absence of an inhibitor at the same temperature to obtain the percent of product.

Determination of Ligand TQ30 and Ligand TQ21 Substrate Activity

In a representative experimental procedure 5'-end labeled ligand TQ30 (SEQ ID NO:50), TQ21 (SEQ ID NO:59) or TQ21 (3'-capped with an ethylene glycol linker) (approximately 3 pmole) was incubated in 20 μL of the binding buffer and 1 mM each dNTPs in the absence and presence of either 5 U of Taq polymerase or 2.5 U of Tth polymerase for 16 hours at room temperature. Capping of the 3'-end of TQ21 was accomplished with an ethylene glycol linker (3'-Spacer C3 support from Glen Research) using standard conditions known in the art.

Affinity Capture Assays

The affinity capture reactions were performed at 70° C. for 5 minutes in a 100 μL reaction volume that contained: 75 μM heparin, 12.5 mM $MgCl_2$, 1 mM each dNTPs, 50 mM KCl, 10 mM Tris-HCl (pH 8.3), 5 U of Taq polymerase or 2.5 U of Tth polymerase and 250 nM 5'-end labeled hairpin assay template (DNA-HP). After 5 minutes the reaction mixture was diluted by three fold and cooled to 4° C. After round 1 synthesis, 15 μL of beads (either affinity beads or control beads, prepared as described above) were added to the reaction mixture at 4° C. and gently mixed for 10 minutes. Supernatants containing the labeled template were recovered after centrifugation and saved for gel analysis. The beads were then washed five times with 100 μL of a buffer consisting of 75 μM heparin, 12.5 mM $MgCl_2$, 50 mM KCl and 10 mM Tris-HCl (pH 8.3). After round 2 synthesis, the washed beads were mixed with a fresh aliquot of the reaction mixture containing all of the reagents except the polymerase. After incubating at 70° C. for 5 minutes, the reaction mixture was recovered and analyzed by gel electrophoresis.

Example 3

Exonucleoase Inhibition Assay

The exonucleoase inhibition assays were performed using the designed template, 5'-TTCGAGCGTGAATCTGAATTCGCGGCTAGCCAG CTTTTGCTGGCTAGCCGCGGTG GGAAACTGAGG-TAGGTGTTTTCACCTACCTCAGTT TCCCACC-3' (Exo-sub) (SEQ ID NO:75), radiolabeled at the 5' end (using [γ$^{32}$P]-ATP and T4 polynucleotide kinase) and at the 3' end using ([α$^{32}$P]-ddATP and deoxyterminaltransferase). In a representative experimental procedure for Taq and Tth pol, 5 U of Taq polymerase or 2.5 U of Tth polymerase, respectively, was mixed with 250 nM of ligand TQ30 or ligand TQ21 in the standard PCR buffer (20 μL), followed by the addition of the double-labeled Exo-Sub (250 nM, added last). After incubating for 16 hours at room temperature, the reactions were quenched by addition of EDTA to 0.1 mM final concentration. Cleavage products were resolved on 8% polyacrylamide gels run under denaturing conditions.

In a representative experimental procedure for TZ05, 1 U of TZ05 polymerase was mixed with the ligand in the TZ05 buffer (50 mM Tricine-KOH, 125 mM KOAc, 2.5 mM $Mn(OAc)_2$, 8% glycerol; 20 μL), followed by the addition of the double-labeled Exo-Sub (250 nM, added last). After incubating for 20 minutes at 45° C., the reactions were quenched by addition of EDTA to 0.1 mM final concentration. Cleavage products were resolved on 8% polyacrylamide gels run under denaturing conditions.

Example 4

Polymerase Inhibition Assays

Inhibition by TQ21 (SEQ ID NO:59) and TQ30 (SEQ ID NO:50) was tested on (A) thermophilic DNA polymerases, (B) mesophilic DNAPs (Taq polymerase as a control), and reverse transcriptases, and (C) reverse transcriptases (RTs). All reactions were carried out in 20 μL volume with the HP hairpin template (Example 2) in the presence of 1 mM each dNTPs, using either 250 or 500 nM of ligand TQ21 or TQ30. Specific reaction conditions for each polymerase were as follows:

Thermostable Polymerases: Tma polymerase: UlTma polmerase (6 U), 10 mM Tris-HCl, pH 8.8, 10 mM KCl, 2.5 mM MgCl$_2$ and 0.002% Tween 20 (v/v); Tbr polymerase (2U), 10 mM Tris-HCl, pH 8.8, 50 mM KCl, 1.5 mM MgCl$_2$ and 0.01% Triton X-100; Tli polymerase (3U) and Tfl polymerase (5 U), 10 mM Tris-HCl; pH 9.0, 50 mM KCl and 0.1% Triton X-100.

Mesophilic Polymerases: All incubations including Taq polymerase (5U) (an internal control for the buffer) were performed in a buffer consisting of 10 mM Tris-HCl, pH 7.5, 40 mM KCl, 5 mM MgCl$_2$ and 7.5 mM DTT (Klenow fragment (5U); T4 DNA polymerase (4U); T7 DNA polymerase (7U)).

Reverse Transcriptases. All incubations were performed in a buffer consisting of 50 mM Tris-HCl, pH 8.3, 60 mM NaCl, 6 mM Mg(OAc)$_2$ and 10 mM DTT. (HIV-1 RT (0.56 pmoles); AMV RT (1 U); M-MLV RT (10 U); Superscript II (Ssript II) (10 U).

Example 5

Detection of Low Copy Number Target

PCR amplifications were performed using a system that amplifies a 203-bp target-specific product from HIV-2 LTR as described by Respess et al. (1994) Interscience Conference on Antimicrobial Agents and Chemotherapy 94:110, without "hot start" conditions. All PCR amplifications were carried out in the presence of 1.3 µg of human placental DNA, 0.4 mM each dNTP, 25 pmoles of each primer, 10 mM Tris-HCl[000c](pH 8.3), 2.5 mM MgCl$_2$, 10% glycerol, 0.2 pmoles (5 U) of Taq polymerase and the template (approximate number of copies as indicated in FIGS. 10A–10C) in 100 µL reaction volume. Thermocycling was performed in a TC9600 thermocycler (PE Applied Biosystems) at 50° C. for 2 minutes followed by 94° C. for 30 sec; 60° C. for 30 seconds; 72° C. for 30 seconds and then autoextended 60° C. annealing in 1° C. increments for 5 cycles. This followed a 35-cycle amplification at 90° C. for 30 seconds; 65° C. for 30 seconds; 72° C. for 30 seconds.

Alternatively, PCR amplifications designed to detect the long terminal repeat (LTR) of HIV-2 were carried out in the presence of 1 µg of human placental DNA (Respess et al. (1994) Interscience Conference on Antimicrobial Agents and Chemotherapy 94:110) without "hot start" conditions. PCR contained 15 mM Tricine-KOH (pH 8.0), 48 mM KOAc (pH 7.5), 3.5 mM Mg (OAc)$_2$, 10% glycerol, 0.4 mM dNTPs and 0.2 pmoles (5 U) of Taq polymerase in 100 µL volume. Ligands were used at 50 nM concentration and were present in the reaction mixture before the template was added. The template contained zero or approximately 10 copies of HIV-2 template DNA mixed with 1 µg of human placental DNA in 50 µL volume. Thermocycling was performed in a TC9600 thermocycler (PE Applied Biosystems) at 50° C. for 2 minutes, 94° C. for 30 seconds, 60° C. for 30 seconds (with autoextention at 1° C./cycle for five cycles), 72° C. for 30 seconds followed by 35 cycles of 90° C. for 30 seconds, 65° C. for 30 seconds and 72° C. for 30 seconds. At the end, reactions were incubated at 72° C. for 10 minutes. Twenty microliters from PCR were analyzed on 8% polyacrylamide gels electrophoresed under native conditions. Gels were visualized by ethidium bromide staining.

Performance of aptamers selected on TZ05 pol was evaluated in a PCR system designed to amplify human K-ras gene from human genomic DNA (Nilsson et al., 1997) without "hot start" conditions. PCR amplification was carried out using primers, 5'-TGAAAATGACTGAATATAAACTT-3' and 5'-GATCATATTCGTCCAC AAAATGA-3'. All PCR were carried out in 30 µL reaction volume on GeneAmp PCR System 9600 (Perkin-Elmer). PCR contained either 10 mM Tris-HCl (pH 8.3), 50 mM KCl, 2.5 mM MgCl$_2$, 1 µM each primer, 200 µM each dNTPs or 50 mM Tricine-KOH, 125 mM KOAc, 2.5 mM Mn(OAc)$_2$, 8% glycerol, 1 µM each primer and 200 µM each dNTPs. Aptamers were present in reactions containing the buffer and 2.5 U of TZ05 polymerase, before 25 ng of human placental DNA was added as the template. After 2 minutes denaturation at 94° C., 34 cycles of amplification were performed at 94° C. for 30 sec, 55° C. for 30 sec, 75° C. for 45 sec. This was followed by a single incubation at 72° C. for 5 minutes. Amplified products were analyzed by running 5 µL of PCR on 3% agarose (NuSieve GTG; FMC BioProducts) gels in TBE buffer. Gels were visualized under UV light after staining with ethidium bromide.

"Hot start" PCR was performed by using "AmpliWax" beads (from Perkin Elmer) according to manufacture's instructions. All other PCR amplifications were carried out without "hot start" conditions.

"NeXstart" PCR was performed using ligands TQ30 and TQ21, (50 nM final concentration) as inhibitors. One amplification was performed in the presence of a nonspecific oligonucleotide (50 nM final concentration) for purposes of comparison.

TABLE 1

Starting Random Sequence Pool of ssDNA:

5'-TTCTCGGTTGGTCTCTGGCGGAGC-[N]$_{30}$-TCTTGTGTATGATTCGCTTTTCCC-3'     (SEQ ID NO:1)

SELEX PCR Primer Set I:

5'-TTCTCGGTTGGTCTCTGGCGGAGC-3'     (SEQ ID NO:2)

5'-BBBTAGGGAAAAGCGAATCATACACAAGA-3'     (SEQ ID NO:3)

(B represents Biotin)

SELEX PCR Primer Set II:

5'-GGC<u>GAATTC</u>TTCTCGGTTGGTCTCTGGCGGAGC-3'     (SEQ ID NO:4)
    EcoRI

5'-CGC<u>GGATCC</u>TAATACGACTCACTATAGGGAAAAGCGAATCATACACAAGA-3'     (SEQ ID NO:5)
    BamHI

TABLE 2

| SEQ ID NO: | CLONE NO: | SEQUENCE (5'→3') |
|---|---|---|
| Family I | | |
| 7 | 2: | TATCGTTACTCATT GTTTTG TGTGT |
| 8 | 34: | ACATTACCCGAGACATTCCTGAC GTTTTG |
| 9 | 21: | TGCTGCTCCTTGTTC GTTTTG TCT |
| 10 | 18: | AGCTTTTGGGACATTCTAAC GTTTTG TCA |
| 11 | 19: | AGATGCTTCA GTTTTC TCTCCGTG |
| 12 | 16: | T CTTTTG GACTGAAGGTTTGTTGGT |
| 13 | 12: | ATGGTC TTTTTG TTGTTTGTTTG |
| 14 | 9: | GTGA CTTTTT ACTTGTCCTAGGCTG |
| 15 | 15: | CATCTAT GTCTTC TTTATATTTGG |
| 16 | 14: | ACTACCTGG TTGTGTG CTTTCCAT |
| 17 | 25: | ATCCATGAGACTAG GTTGGT TAGGGTGGTG |
| 18 | 1: | CCCTCATA GTTTAA CTTTACCTGGCTTATC |
| 19 | 10: | AGTGAACACCTTCT GTTTCG TGAGTC |
| 20 | 23: | CGTGT GTCTTA GTTAGCTCGTGG |
| 21 | 24: | TAACGTTGTGT GTTCTG TGCTA |
| 22 | 26: | AACAGATTTGGTCATAT TCCTTG G |
| 23 | 27: | TGTGTTAT GCTCCG GTAACAATGCCCTT |
| 24 | 30: | AATTGTA ATTTCG GTATCTCTG |
| 25 | 33: | GCA ATTTCC TGTCCAATCATTGTAG |
| 26 | 36: | GCTTGAA GCTTTC ACCCATCCTA/GA |
| 27 | 41: | CTTCTCCTTTATAT GTCTTA CCA |
| 28 | 42: | TATCGAGTAGACCCTGTT GTTCGT G |
| 29 | 44: | CGC GTCTAG CTAAGATTTCTACTGATGCAT |
| 30 | 46: | ATG ATTTTA TGTTTATCCTGTTT |
| Family II | | |
| 31 | 45: | CAGTCGCTGTACGTGCTCTCCCTATGTAAC |
| 32 | 6: | CAATCGGTGTACAATATCTTCC |
| 33 | 28: | CGTTAGCTGGTTAGTTAGTACTAG |
| 34 | 35: | AGGTAAGCGATTATGGGGTTATCG |
| 35 | 40: | TAGTTACATGAACTAATCGTGGAG |

TABLE 3

| SEQ ID NO: | CLONE NO: | SEQUENCE (5'-3') |
|---|---|---|
| Family I | | |
| 36 | 12: | (4) ggcggagc GATGTACAGTATC GCTATCGAAAGAGGCTG |
| 37 | 15: | ggcggagc AGTGTGCAGTAGT GTGATGTCAGAGTATCC |

TABLE 3-continued

| SEQ ID NO: | CLONE NO: | | SEQUENCE(5'-3') | | |
|---|---|---|---|---|---|
| 38 | 18: | | ggcggagc | AGTGTGCGGTAGT | GTGATCTGAGAGTATCC |
| 39 | 26: | | ggcggagc | AGTGTGTAGTAGT | GTTACGATGGGGACGG |
| 40 | 40: | | ggcggagc | AGTGTACAGTAGT | GTTCCCGGTAGAGCTAT |
| 41 | 27: | | ggcggagc | AATGTGCAGTATT | GATATCGCTGGTGGTCA |
| 42 | 10: | (2) | ggcggagcA | AGTGTACAGTAGT | TGCCTACGCTAGTG |
| 43 | 6: | | ggcggagcA | AGTGTGCAGTAGT | TACTCATAAGAGACCA |
| 44 | 34: | | ggcggagcA | AGTGTACAGTAGT | TGCCTACGCTAGTG |
| 45 | 28: | | ggcggagcAC | AATGTGAAGTATT | GGGGTACGTCAGTAG |
| 46 | 5: | | CAAGCGGAAAC | AATGTACA6GTATT | GGGATC |
| 47 | 33: | | AAGGCCATT | GATGTACAGTATC | AATGCTGC |
| 48 | 29: | | AATTGGGAAAC | AATGTGCAGTATG | TGAAGG |
| 49 | 44: | | AAATGGGAAAC | AATGTGCAGTATT | GGAAGG |
| 50 | 30: | (3) | AAGACCAGAC | AATGTACAGTATT | GGCCTGA |
| 76 | 3: | | TCAATACACAAATT | GATGTACAGTGTC | GAT |
| Family II | | | | | |
| 51 | 42: | | TACGCTGACAGGCC | ACGTTTTG | TCATGAT |
| 52 | 22: | | GAGAACTCCGTTCTTA | GCGTATTG | GAGTCC |
| 53 | 2: | | AGGTGGGACATTCTTT | GCGTTATG | TCTCTGA |
| 54 | 49: | | GGGCTCGGAACATTCTTA | GCGTTTTG | TTCC |
| 55 | 50: | | ATAGGCAGGGGACATTGCA | ACCTTTTG | TCA |
| 56 | 7: | | AATTGAAGTGACTTTCTCT | GCGTTTAG | TCG |
| 57 | 39: | | AGGAATCTGGGGCATTCTTT | GCGTTTTG | CG |
| 58 | 41: | | CTCAGGATAAGGTCATTCTA | ACGTTATG | A |
| 59 | 21: | | GATCATCTCAGAGCATTCTTA | GCGTTTTG | T |
| 60 | 31: | | GATCATCTAAGAGCATTCTTA | GCGTTTTG | G |
| 61 | 43: | | CAAAACGAGAGAGCTTTCTGT | GCGTTTAG | C |
| 62 | 23: | | GACCAAGCGTCAAGATATTCAA | ACGTTTTA | |
| 63 | 25: | | AGAAGCATACGAAGACATTCCA | ACGTTTGG | |
| 64 | 9: | (2) | AATCGATTGTTGAACATTCTG | ACGTTTTG | T |
| 65 | 17: | (2) | AGAAGCATACGAAGACATTCCA | ACGTTTTG | |
| 66 | 36: | | AGAAGCATACGAAGACATTCCA | ACGTTTTG | |
| Family III | | | | | |
| 77 | 4: | (2) | CATTGGGCCAGAGGAACACAACCTCAACAG | | |

TABLE 4

| SEQ ID NO: | Family | Clone # | Sequence (5'-3') | | | | | % Frequency |
|---|---|---|---|---|---|---|---|---|
| 78 | I | 6 | GAATCATACGAAGA | CATT | CC-AA | CGTTTTG | | 25.3 |
| 79 | | 4 | GGATCAGACACGAGA | CATT | GC-GG | ACTTTTG | | 30.1 |
| 80 | | 3 | GATCAGACACGAAA | CATT | GC-GG | ACTTTTG | | 11.1 |
| 81 | | 1 | ATACACGACGT | CATT | CT-AG | CGTTTTG | ACG | 7.9 |
| 82 | | 9 | AGAAACAAGAAT | CATT | CTTAG | CGTTTTG | AT | 12.6 |
| 83 | | 18 | ATACACGACGT | CATT | CT-AG | CGTTTTG | | 1.6 |
| 84 | II | 19 | GAATCGGACATCAAGGGTTCCAGCAGCAGTGCT | | | | | 9.5 |

TABLE 5

| SEQ ID NO: | | SEQUENCE (5'-3') | $K_d$* (pM) | $IT_{50}$¶ (° C.) |
|---|---|---|---|---|
| 78 | 6 | GAATCATACGAAGACATTCCAACGTTTTG | 8.5 ± 1.3 | 54.8 |
| 85 | 10 | GGATCAGACACGAAACATTGCGGACTTTTG | 30 ± 9 | 44.6 |
| 86 | 15 | ATGCACAGCGACATTCTCAGCGTTTTGTCG | 13.8 ± 2 | 52.3 |
| 84 | 19 | GAATCGGACATCAAGGGTTCCAGCAGTGCT | 11.2 ± 2 | 53.7 |
| 80 | 20 | GATCAGACACGAAACATTGCGGACTTTTG | 105 ± 10 | 41 |
| 81 | 22 | ATACACGACGTCATTCTAGCGTTTTGACG | 14 ± 1.5 | 56 |
| 87 | 28 | AGGAGCAAGAATCATTCTTAGCGTTTTGAT | 13.5 ± 1.5 | 52 |
| 88 | 36 | AGAAGCAAGAATCATTCTTAGCGTTTTGAT | 31 ± 4 | 52 |
| 83 | 18 | ATACACGACGTCATTCTAGCGTTTTG | >>1000 | <40 |

TABLE 6

| SEQ ID NO: | Family | Clone Number | | Sequence (5'-3') |
|---|---|---|---|---|
| 89 | I | 13 | (2) | ACGTCGGGGGGGCGTTGGGACGGGCAGACG |
| 90 | | 51 | | ACATCGGGGGGCGTTGGGACAGGCAGATG |
| 91 | | 75 | | ATGTCGGGGGGCGTTGGGACGGGCAGGC |
| 92 | | 50 | | ACATCGGGGGGCGTTGGGAAAGGCAGATG |
| 93 | | 26 | | ACGTCGGGGGGCCCTGGGACGGGCAGGCG |
| 94 | | 1 | (15) | ACACCGGGGGGGCTGCGGGCAAGGCGGGTG |
| 95 | | 62 | | ACACCGGGGGGGCTGGGGGAAAGGCCGGTG |
| 96 | II | 2 | (3) | GCGAGGGTGTGGCGTGGGTGGCGCGA |
| 97 | | 56 | | GCAAGGGTGTGGCGTGGGTGGCGCGA |
| 98 | | 30 | | ACGGGAGGGTGTGGAGTGGGTGGCGCGGGC |
| 99 | | 36 | (5) | ACGGGAGGGTGTGGAGTGGGTGGCGCGGGC |
| 100 | III | 8 | (4) | GAAGCATACGAGGACATTCCAACGTTTTG |
| 101 | | 9 | (8) | GGATCAGACACGAGACATTGCGGACTTTTG |
| 102 | | 25 | | GAAAGCATACGAAGACATTCCAACGTTTTG |
| 103 | | 54 | (2) | GAAGCATACGAAGACATTCCAACGTTTTG |
| 104 | | 60 | | AGAAGCATACGAAGACATTCCAACGTTTTG |
| 105 | | 69 | | GAACATACGAAGACATTCCAACGTTTTG |
| 106 | | 3 | (2) | ATACACGACGTCATTCTAGCGTTTTGACG |

TABLE 7

| | $K_d$ (pM) | | | |
|---|---|---|---|---|
| | in Tris Buffer | | in Tricine Buffer | |
| Clone Number | 40° C. | 55° C. | 40° C. | 55° C. |
| 6 | 5 ± 0.6 | 8.5 ± 1.3 | 4.6 ± 1.4 | 36 ± 2.5 |
| 22 | 3.8 ± 0.6 | 14 ± 1.5 | 5.6 ± 0.7 | 18 ± 2 |
| 28 | 5 ± 1 | 13.5 ± 1.5 | 9.4 ± 1.5 | 116 ± 11 |

TABLE 8

| Clone Number | $K_d$ (pM)[f] | $IT_{50}$ (° C.) |
|---|---|---|
| TZ 1 | 16 ± 5 | 52.5 |
| TZ 2 | >>1000 | <<35 |
| TZ 3 | 9 ± 3 | 52 |
| TZ 8 | 5 ± 3 | 52 |
| TZ 9 | 5 ± 3 | 52 |
| TZ 13 | 17 ± 3 | 58.5 |
| TZ 26 | >>500 | 41 |
| TZ 36 | 20 ± 4 | 51 |
| TZ 54 | 23 ± 4 | 52 |
| TZ 69 | 20 ± 5 | 46 |

[f]Binding interactions were measured at 55° C.
Measured with 250 nM aptamer concentration

TABLE 9

| | $K_d$ (pM) | | | |
|---|---|---|---|---|
| | In Tris Buffer | | In Tricine Buffer | |
| | Full-lengths | Truncates | Full-lengths | Truncates |
| TQH 6 = | 8.5 ± 1.3 | 38 ± 7 | 36 ± 2.5 | 128 ± 8 |
| TQH 28 = | 13.5 ± 1.5 | 43 ± 3 | 116 ± 11 | 93 ± 10 |

TABLE 10

| SEQ ID NO: | CLONE NO: | SEQUENCE |
|---|---|---|
| 50 | TQ30 | 5'-ttctcggttggtctctggcggagcAAGACCAGACAATGTACAGTATTGGCCTGAtcttgtgtatgattcgcttttccc-3' |
| 59 | TQ21 | 5'-ttctcggttggtctctggcggagcGATCATCTCAGAGCATTCTTAGCGTTTTGTtcttgtgtatgattcgcttttccc-3' |
| 67 | Trnc.1-30 | 5'-GGGACCAGACAATGTACAGTATTGTCTGGTCCC-3' |
| 68 | Trnc.2-30 | 5'-GCCGGCCAATGTACAGTATTGGCCGGC-3' |
| 69 | Trnc.3-30 | 5'-GGCCAATGTACAGTATTGGCC-3' |
| 70 | Trnc-21 | 5'-tggcggagcGATCATCTCAGAGCATTCTTAGCGTTTTGTtcttgtgtatga-3' |
| 71 | D.30-D.30 | 5'-GCCGGCCAATGTACAGTATTGGCCGGC⟍<br>                                               ⟩X<br>5'-GCCGGCCAATGTACAGTATTGGCCGGC⟋ |
| 72 | D.21-D.30 | 5'-tggcggagcGATCATCTCAGAGCATTCTTAGCGTTTTGTtcttgtgtatgaT<br>                                                                    T<br>3'-CGGCCGGTTATGACATGTAACCGGCGT |
| 73 | D.30-D.21 | 5'-GCCGGCCAATGTAGACTATTGGCCGGCT<br>                                                                    T<br>3'-agtatgtgttctTGTTTTGCGATTCTTACGAGACTCTACTAGcgaggcggtT |

TABLE 11

| SEQ ID NO: | CLONE NO: | Secondary Structure[1] | $K_d{}^2$(nM) | $T_M{}^3$(° C.) |
|---|---|---|---|---|
| 74 | Trnc.A-30 (30-mer) | 5'-AAGAC      A       A<br>          CAG   CAATGT<br>          \|\|\|   \|\|\|\|\|\|oo  C<br>          GTC   GTTATG<br>3'-A      CG       A | 0.6 ± 0.1 | 51 |
| 67 | Trnc.1-30 (33-mer) |                      A<br>5'-GGGACCAGAGGCCAATGT<br>   \|\|\|\|\|\|\|\|\|\|\|\|\|\|\|\|\|oo  C<br>3'-CCCTGGTCTCCGGTTATG<br>                     A | 2.0 ± 0.3 | 77 |
| 68 | Trnc.2-30 (27-mer) |               A<br>5'-GCCGGCCAATGT<br>   \|\|\|\|\|\|\|\|\|\|\|oo  C<br>3'-CGGCCGGTTATG<br>              A | 3.1 ± 0.3 | 81.5 |
| 69 | Trnc.3-30 (24-mer) |            A<br>5'-GGCCAATGT<br>   \|\|\|\|\|\|\|oo  C<br>3'-CCGGTTATG<br>           A | 2.8 ± 0.4 | 65.5 |

[1]The boxed region denotes the conserved sequence element with the predicted stem-loop structure identified in the Family I sequences; vertical lines signify Watson-Crick type base pairing; circles show an uncommon G-T base pair.
[2]$K_d$ values were measured by the nitrocellulose filter binding technique described in Example 1.
[3]Melting transitions ($T_m$) were measured in a PCR buffer containing 10 mM Tris-HCl, 50 mM KCl, 2 mM $MgCl_2$, pH 8.3, at a 1° C./min temperature ramp.

TABLE 12

| | $IT_{50}$ (° C.) | | $TC_{50}$ (@ 45° C.) nM | |
|---|---|---|---|---|
| | Full-lengths | Truncates | Full-lengths | Truncates |
| TQH 6 = | 54.8 | 46 | 30 | 97 |
| TQH 22 = | 56.1 | 47 | 37 | 100 |
| TQH 28 = | 52 | 47 | 37 | 75 |

TABLE 13

| | $K_d$ (pM) | |
|---|---|---|
| Clone | Full-length | Truncates (51-nt) |
| TZ 1 | 16 | 26 |
| TZ 13 | 17 | 22 |
| TZ 36 | 20 | 28 |

TABLE 14

| | $IT_{50}$ ° C. | | |
|---|---|---|---|
| | | Truncates | |
| Clone | Full-length | 51-nt | 30-nt |
| TZ 1 | 52.5 | 52 | 48 |
| TZ 13 | 58.5 | 51 | 42 |
| TZ 36 | 51 | 47 | <30 |

TABLE 15

| Clone | $K_d$ (pM) | $IT_{50}$ (° C.) |
|---|---|---|
| TZ 13 SymD1 | 20 ± 3 | 56 |
| TZ 13 SymD2 | 82 ± 10 | 48 |
| TZ 13 Tandem | 18 ± 2 | 54 |
| TZ 13 30-nt monomer | 145 ± 10 | 43 |

What is claimed is:

1. A method of identifying nucleic acid ligands to a polymerase, comprising:
   a) preparing a candidate mixture of nucleic acids;
   b) heating the candidate mixture of nucleic acids with said polymerase to a predetermined temperature, wherein nucleic acids having an increased affinity to the polymerase relative to the candidate mixture at that temperature may be partitioned from the remainder of the candidate mixture;
   c) partitioning the increased affinity nucleic acids from the remainder of the candidate mixture at said predetermined temperature; and
   d) amplifying the increased affinity nucleic acids to yield a mixture of nucleic acids enriched for nucleic acid sequences with relatively higher affinity and specificity for binding to the polymerase, whereby nucleic acid ligands of the polymerase may be identified.

2. The method of claim 1 further comprising:
   e) repeating steps b), c), and d).

3. The method of claim 1 wherein said polymerase is selected from a DNA polymerase and a reverse transcriptase.

4. The method of claim 1 wherein said polymerase is thermostable.

5. The method of claim 3 wherein said DNA polymerase is selected from *Thermus aquaticus* polymerase (Taq polymerase), *Thermus thermophilus* polymerase (Tth polymerase) and TZ05 polymerase.

6. The method of claim 1 wherein said candidate mixture of nucleic acids is comprised of single stranded nucleic acids.

7. The method of claim 1 wherein said single stranded nucleic acids are deoxyribonucleic acids.

8. A method for inhibiting a DNA polymerase, comprising adding a nucleic acid ligand that inhibits said DNA polymerase DNA at a predetermined temperature to a DNA polymerization reaction.

9. The method of claim 8 wherein said DNA polymerase is selected from Taq polymerase, Tth polymerase and TZ05 polymerase.

10. The method of claim 9 wherein said polymerase ligand is a DNA selected from the ligands of Table 4 (SEQ ID NOS:78–84), Table 5 (SEQ ID NOS:85–88), Table 6 (SEQ ID NOS:89–106), FIG. 33 (SEQ ID NOS:107–115), and FIG. 38 (SEQ ID NOS:116–118).

11. A purified and isolated non-naturally occurring nucleic acid ligand identified according to the method of claim 3.

12. The purified and isolated non-naturally occurring nucleic acid ligand of claim 11, wherein said ligand is selected from the group consisting of the sequences set forth in Table 4 (SEQ ID NOS:78–84), Table 5 (SEQ ID NOS:85–88), Table 6 (SEQ ID NOS:89–106), FIG. 33 (SEQ ID NOS:107–115), and FIG. 38 (SEQ ID NOS:116–118).

13. The purified and isolated non-naturally occurring nucleic acid ligand of claim 11, wherein said ligand is substantially homologous to and has substantially the same ability to bind the polymerase as a ligand selected from the group consisting of the sequences set forth in Table 4 (SEQ ID NOS:78–84), Table 5 (SEQ ID NOS:85–88), Table 6 (SEQ ID NOS:89–106), FIG. 33 (SEQ ID NOS:107–115), and FIG. 38 (SEQ ID NOS:116–118).

14. A method for performing the Polymerase Chain Reaction (PCR) comprising:
   a) mixing a sample containing a nucleic acid sequence that is to be amplified with primers that are complementary to the sequences that flank the sequence to be amplified, a thermostable polymerase, and a nucleic acid ligand that is capable of inhibiting the polymerase at a predetermined temperature, yet allows the polymerase to be activated at temperatures above said predetermined temperature; and
   b) performing the standard PCR steps of melting the target nucleic acid, annealing the primers to the target nucleic acid, and synthesizing the target nucleic acid, by thermal cycling of the mixture.

15. The method of claim 14 wherein said thermostable polymerase is selected from Taq polymerase and TZ05 polymerase.

16. The method of claim 14 wherein said nucleic acid ligand is selected from the group consisting of the sequences set forth in Table 4 (SEQ ID NOS:78–84), Table 5 (SEQ ID NOS:85–88), Table 6 (SEQ ID NOS:89–106), FIG. 33 (SEQ ID NOS:107–115), and FIG. 38 (SEQ ID NOS: 116–118).

17. The method of claim 14 wherein said acid ligand substantially homologous to and has substantially the same ability to bind the thermostable polymerase as a ligand selected from the group consisting of the sequences set forth in Table 4 (SEQ ID NOS:78–84), Table 5 (SEQ ID NOS:85–88), Table 6 (SEQ ID NOS:89–106), FIG. 33 (SEQ ID NOS:107–115), and FIG. 38 (SEQ ID NOS:116–118).

18. A method for inhibiting the activity of a thermostable DNA polymerase, comprising adding a nucleic acid ligand that inhibits said DNA polymerase, identified according to the method of claim 1, to a DNA polymerization reaction which is being maintained at a temperature at or below which said ligand inhibits polymerization.

19. The method of claim 18 wherein said DNA polymerase is selected from Taq polymerase and TZ05 polymerase.

20. The method of claim 18 wherein said polymerase ligand is a DNA selected from the ligands of Table 4 (SEQ ID NOS:78–84), Table 5 (SEQ ID NOS:85– 88), Table 6 (SEQ ID NOS:89–106), FIG. 33 (SEQ ID NOS:107–115), and FIG. 38 (SEQ ID NOS:1 16–118).

21. A method of identifying a nucleic acid ligand switch for a polymerase, comprising:
   a) preparing a candidate mixture of nucleic acids;
   b) contacting the candidate mixture of nucleic acids with a polymerase, wherein nucleic acids having an increased affinity to the polymerase relative to the candidate mixture may be partitioned from the remainder of the candidate mixture;
   c) partitioning the increased affinity nucleic acids from the remainder of the candidate mixture
   d) further partitioning the increased affinity nucleic acids of step c) based on their lack of affinity to the polymerase upon the variation of an environmental parameter; and
   e) amplifying the increased affinity nucleic acids obtained in d) to yield a mixture of nucleic acids enriched for nucleic acid sequences with relatively higher affinity and specificity for binding to the polymerase, whereby a nucleic acid ligand switch of the polymerase may be identified.

* * * * *

SEQUENCE LISTING

<160> NUMBER OF SEQ ID NOS: 119

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (25)..(54)
<223> OTHER INFORMATION: n at positions 25-54 is any base

<400> SEQUENCE: 1
ttctcggttg gtctctggcg gagcnnnnnn nnnnnnnnnn nnnnnnnnnn nnntcttgt    60 gtatgattcg cttttccc                                                78

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
ttctcggttg gtctctggcg gagc                                         24

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

```
<400> SEQUENCE: 3
tagggaaaag cgaatcatac acaaga                                          26

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 4
ggcgaattct tctcggttgg tctctggcgg agc                                  33

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5
cgcggatcct aatacgactc actataggga aaagcgaatc atacacaaga                50

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 6
atgcctaagt ttcgaacgcg gctagccagc ttttgctggc tagccgcgt                 49

<210> SEQ ID NO 7
<211> LENGTH: 74
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 7
ttctcggttg gtctctggcg gagctatcgt ttactcattg ttttgtgtgt tcttgtgtat     60
gattcgcttt tccc                                                       74

<210> SEQ ID NO 8
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 8
ttctcggttg gtctctggcg gagcacatta cccgagacat tcctgacgtt ttgtcttgtg     60
tatgattcgc ttttccc                                                    77

<210> SEQ ID NO 9
<211> LENGTH: 72
<212> TYPE: DNA
<213> ORGANISM: Artificial Sequence
<220> FEATURE:
```

<223> OTHER INFORMATION: Description of Artificial Sequence: Synthetic
      Sequence

<400> SEQUENCE: 9
ttctcggttg gtctctggcg gagctgctgc tccttgttcg ttttgtcttc ttgtgtatga    60
ttcgcttttc cc    72

<210> SEQ ID NO 10
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 10
ttctcggttg gtctctggcg gagcagcttt tggggacatt ctaacgtttt gtcatcttgt    60
gtatgattcg ctttttccc    78

<210> SEQ ID NO 11
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 11
ttctcggttg gtctctggcg gagcagatgc ttcagttttc tctccgtgtc ttgtgtatga    60
ttcgcttttc cc    72

<210> SEQ ID NO 12
<211> LENGTH: 73
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 12
ttctcggttg gtctctggcg gagctctttt ggactgaagg tttgttggtt cttgtgtatg    60
attcgctttt ccc    73

<210> SEQ ID NO 13
<211> LENGTH: 71
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 13
ttctcggttg gtctctggcg gagcatggtc tttttgttgt ttgtttgtct tgtgtatgat    60
tcgcttttcc c    71

<210> SEQ ID NO 14
<211> LENGTH: 73
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 14
ttctcggttg gtctctggcg gagcgtgact ttttacttgt cctaggctgt cttgtgtatg        60
attcgctttt ccc                                                           73

<210> SEQ ID NO 15
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 15
ttctcggttg gtctctggcg gagccatcta tgtcttcttt atatttggtc ttgtgtatga        60
ttcgcttttc cc                                                            72

<210> SEQ ID NO 16
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 16
ttctcggttg gtctctggcg gagcactacc tggttgtgtg ctttccattc ttgtgtatga        60
ttcgcttttc cc                                                            72

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 17
ttctcggttg gtctctggcg gagcatccat gagactaggt tggttagggt ggtgtcttgt        60
gtatgattcg cttttccc                                                      78

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 18
ttctcggttg gtctctggcg gagcccctca tagtttaact ttacctggct tatctcttgt        60
gtatgattcg cttttccc                                                      78

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 19
ttctcggttg gtctctggcg gagcagtgaa caccttctgt ttcgtgagtc tcttgtgtat        60
gattcgcttt tccc                                                          74

<210> SEQ ID NO 20
<211> LENGTH: 71
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 20
ttctcggttg gtctctggcg gagccgtgtg tcttagttag ctcgtggtct tgtgtatgat      60
tcgcttttcc c                                                          71

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 21
ttctcggttg gtctctggcg gagctaacgt tgtgtgttct gtgctatctt gtgtatgatt      60
cgcttttccc                                                            70

<210> SEQ ID NO 22
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 22
ttctcggttg gtctctggcg gagcaacaga tttggtcata ttccttggtc ttgtgtatga      60
ttcgcttttc cc                                                         72

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 23
ttctcggttg gtctctggcg gagctgtgtt atgctccggt aacaatgccc tttcttgtgt      60
atgattcgct tttccc                                                     76

<210> SEQ ID NO 24
<211> LENGTH: 70
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 24
ttctcggttg gtctctggcg gagcaattgt aatttcggta tctctgtctt gtgtatgatt      60
cgcttttccc                                                            70

<210> SEQ ID NO 25
<211> LENGTH: 73

```
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 25
ttctcggttg gtctctggcg gagcgcaatt tcctgtccaa tcattgtagt cttgtgtatg     60
attcgctttt ccc                                                        73

<210> SEQ ID NO 26
<211> LENGTH: 73
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 26
ttctcggttg gtctctggcg gagcgcttga agctttcacc catcctagat cttgtgtatg     60
attcgctttt ccc                                                        73

<210> SEQ ID NO 27
<211> LENGTH: 71
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 27
ttctcggttg gtctctggcg gagccttctc ctttatatgt cttaccatct tgtgtatgat     60
tcgcttttcc c                                                          71

<210> SEQ ID NO 28
<211> LENGTH: 73
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 28
ttctcggttg gtctctggcg gagctatcga gtagaccctg ttgttcgtgt cttgtgtatg     60
attcgctttt ccc                                                        73

<210> SEQ ID NO 29
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 29
ttctcggttg gtctctggcg gagccgcgtc tagctaagat ttctactgat gcattcttgt     60
gtatgattcg cttttccc                                                   78

<210> SEQ ID NO 30
<211> LENGTH: 71
<212> TYPE: DNA
<213> ORGANISM: Artificial Sequence
<220> FEATURE:
<223> OTHER INFORMATION: Description of Artificial Sequence: Synthetic
```

Sequence

<400> SEQUENCE: 30
ttctcggttg gtctctggcg gagcatgatt ttatgtttat cctgttttct tgtgtatgat    60
tcgcttttcc c                                                         71

<210> SEQ ID NO 31
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 31
ttctcggttg gtctctggcg gagccagtcg ctgtacgtgc tctccctatg taactcttgt    60
gtatgattcg cttttccc                                                  78

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 32
ttctcggttg gtctctggcg gagccaatcg gtgtacaata tcttcctctt gtgtatgatt    60
cgcttttccc                                                           70

<210> SEQ ID NO 33
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 33
ttctcggttg gtctctggcg gagccgttag ctggttagtt agtactagtc ttgtgtatga    60
ttcgcttttc cc                                                        72

<210> SEQ ID NO 34
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 34
ttctcggttg gtctctggcg gagcaggtaa gcgattatgg ggttatcgtc ttgtgtatga    60
ttcgcttttc cc                                                        72

<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 35

```
ttctcggttg gtctctggcg gagctagtta catgaactaa tcgtggagtc ttgtgtatga    60
ttcgcttttc cc                                                       72
```

<210> SEQ ID NO 36
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 36

```
ttctcggttg gtctctggcg gagcgatgta cagtatcgct atcgaaagag gctgtcttgt    60
gtatgattcg cttttccc                                                 78
```

<210> SEQ ID NO 37
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 37

```
ttctcggttg gtctctggcg gagcagtgtg cagtagtgtg atgtcagagt atcctcttgt    60
gtatgattcg cttttccc                                                 78
```

<210> SEQ ID NO 38
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 38

```
ttctcggttg gtctctggcg gagcagtgtg cggtagtgtg atctgagagt atcctcttgt    60
gtatgattcg cttttccc                                                 78
```

<210> SEQ ID NO 39
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 39

```
ttctcggttg gtctctggcg gagcagtgtg tagtagtgtt acgatgggga cggtcttgtg    60
tatgattcgc ttttccc                                                  77
```

<210> SEQ ID NO 40
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 40

```
ttctcggttg gtctctggcg gagcagtgta cagtagtgtt cccggtagag ctattcttgt    60
gtatgattcg cttttccc                                                 78
```

<210> SEQ ID NO 41
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 41
ttctcggttg gtctctggcg gagcaatgtg cagtattgat atcgctggtg gtcatcttgt    60
gtatgattcg cttttccc                                                  78

<210> SEQ ID NO 42
<211> LENGTH: 76
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 42
ttctcggttg gtctctggcg gagcaagtgt acagtagttg cctacgctag tgtcttgtgt    60
atgattcgct tttccc                                                    76

<210> SEQ ID NO 43
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 43
ttctcggttg gtctctggcg gagcaagtgt gcagtagtta ctcataagag accatcttgt    60
gtatgattcg cttttccc                                                  78

<210> SEQ ID NO 44
<211> LENGTH: 76
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 44
ttctcggttg gtctctggcg gagcaagtgt acagtagttg cctacgctag tgtcttgtgt    60
atgattcgct tttccc                                                    76

<210> SEQ ID NO 45
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 45
ttctcggttg gtctctggcg gagcacaatg tgaagtattg gggtacgtca gtagtcttgt    60
gtatgattcg cttttccc                                                  78

<210> SEQ ID NO 46
<211> LENGTH: 78
<212> TYPE: DNA

```
<213> ORGANISM: Artificial Sequence
<220> FEATURE:
<223> OTHER INFORMATION: Description of Artificial Sequence: Synthetic
      Sequence

<400> SEQUENCE: 46
ttctcggttg gtctctggcg gagccaagcg gaaacaatgt acagtattgg gatctcttgt      60
gtatgattcg cttttccc                                                   78

<210> SEQ ID NO 47
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 47
ttctcggttg gtctctggcg gagcaaggcc attgatgtac agtatcaatg ctgctcttgt      60
gtatgattcg cttttccc                                                   78

<210> SEQ ID NO 48
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 48
ttctcggttg gtctctggcg gagcaattgg gaaacaatgt gcagtatgtg aaggtcttgt      60
gtatgattcg cttttccc                                                   78

<210> SEQ ID NO 49
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 49
ttctcggttg gtctctggcg gagcaaatgg gaaacaatgt gcagtattgg aaggtcttgt      60
gtatgattcg cttttccc                                                   78

<210> SEQ ID NO 50
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 50
ttctcggttg gtctctggcg gagcaagacc agacaatgta cagtattggc ctgatcttgt      60
gtatgattcg cttttccc                                                   78

<210> SEQ ID NO 51
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence
```

```
<400> SEQUENCE: 51
ttctcggttg gtctctggcg gagctacgct gacaggccac gttttgtcat gattcttgtg       60
tatgattcgc ttttccc                                                     77

<210> SEQ ID NO 52
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 52
ttctcggttg gtctctggcg gagcgagaac tccgttctta gcgtattgga gtcctcttgt       60
gtatgattcg cttttccc                                                    78

<210> SEQ ID NO 53
<211> LENGTH: 79
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 53
ttctcggttg gtctctggcg gagcaggtgg gacattcttt gcgttatgtc tctgatcttg       60
tgtatgattc gcttttccc                                                   79

<210> SEQ ID NO 54
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 54
ttctcggttg gtctctggcg gagcgggctc ggaacattct tagcgttttg ttcctcttgt       60
gtatgattcg cttttccc                                                    78

<210> SEQ ID NO 55
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 55
ttctcggttg gtctctggcg gagcataggc aggggacatt gcaacctttt gtcatcttgt       60
gtatgattcg cttttccc                                                    78

<210> SEQ ID NO 56
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 56
ttctcggttg gtctctggcg gagcaattga agtgactttc tctgcgttta gtcgtcttgt       60
```

```
gtatgattcg cttttccc                                                    78

<210> SEQ ID NO 57
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 57
ttctcggttg gtctctggcg gagcaggaat ctggggcatt ctttgcgttt tgcgtcttgt      60
gtatgattcg cttttccc                                                    78

<210> SEQ ID NO 58
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 58
ttctcggttg gtctctggcg gagcctcagg ataaggtcat tctaacgtta tgatcttgtg      60
tatgattcgc ttttccc                                                     77

<210> SEQ ID NO 59
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 59
ttctcggttg gtctctggcg gagcgatcat ctcagagcat tcttagcgtt ttgttcttgt      60
gtatgattcg cttttccc                                                    78

<210> SEQ ID NO 60
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 60
ttctcggttg gtctctggcg gagcgatcat ctaagagcat tcttagcgtt ttggtcttgt      60
gtatgattcg cttttccc                                                    78

<210> SEQ ID NO 61
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 61
ttctcggttg gtctctggcg gagccaaaac gagagagctt tctgtgcgtt tagctcttgt      60
gtatgattcg cttttccc                                                    78
```

<210> SEQ ID NO 62
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 62
ttctcggttg gtctctggcg gagcgaccaa gcgtcaagat attcaaacgt tttatcttgt      60
gtatgattcg cttttccc                                                   78

<210> SEQ ID NO 63
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 63
ttctcggttg gtctctggcg gagcagaagc atacgaagac attccaacgt ttggtcttgt      60
gtatgattcg cttttccc                                                   78

<210> SEQ ID NO 64
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 64
ttctcggttg gtctctggcg gagcaatcga ttgttgaaca ttctgacgtt ttgttcttgt      60
gtatgattcg cttttccc                                                   78

<210> SEQ ID NO 65
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 65
ttctcggttg gtctctggcg gagcagaagc atacgaagac attccaacgt tttgtcttgt      60
gtatgattcg cttttccc                                                   78

<210> SEQ ID NO 66
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 66
ttctcggttg gtctctggcg gagcagaagc atacgaagac attccaacgt tttgtcttgt      60
gtatgattcg cttttccc                                                   78

<210> SEQ ID NO 67
<211> LENGTH: 33
<212> TYPE: DNA
<213> ORGANISM: Artificial Sequence

```
<220> FEATURE:
<223> OTHER INFORMATION: Description of Artificial Sequence: Synthetic
      Sequence

<400> SEQUENCE: 67
gggaccagac aatgtacagt attgtctggt ccc                                    33

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 68
gccggccaat gtacagtatt ggccggc                                           27

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 69
ggccaatgta cagtattggc c                                                 21

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 70
tggcggagcg atcatctcag agcattctta gcgttttgtt cttgtgtatg a                51

<210> SEQ ID NO 71
<211> LENGTH: 55
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (32)
<223> OTHER INFORMATION: n at position 32 is a glycerol linkage

<400> SEQUENCE: 71
gccggccaat gtacagtatt ggccggccgg cncggttatg acatgtaacc ggccg            55

<210> SEQ ID NO 72
<211> LENGTH: 81
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 72
tggcggagcg atcatctcag agcattctta gcgttttgtt cttgtgtatg atttgccggc       60
caatgtacag tattggccgg c                                                 81
```

<210> SEQ ID NO 73
<211> LENGTH: 81
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 73
gccggccaat gtacagtatt ggccggcttt tggcggagcg atcatctcag agcattctta    60
gcgttttgtt cttgtgtatg a                                              81

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 74
aagaccagac aatgtacagt attggcctga                                     30

<210> SEQ ID NO 75
<211> LENGTH: 97
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 75
ttcgagcgtg aatctgaatt cgcggctagc cagcttttgc tggctagccg cggtgggaaa    60
ctgaggtagg tgttttcacc tacctcagtt tcccacc                             97

<210> SEQ ID NO 76
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 76
ttctcggttg gtctctggcg gagctcaata cacaaattga tgtacagtgt cgattcttgt    60
gtatgattcg cttttccc                                                  78

<210> SEQ ID NO 77
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 77
ttctcggttg gtctctggcg gagccattgg gccagaggaa cacaacctca acagtcttgt    60
gtatgattcg cttttccc                                                  78

<210> SEQ ID NO 78
<211> LENGTH: 77
<212> TYPE: DNA
<213> ORGANISM: Artificial Sequence
<220> FEATURE:

<223> OTHER INFORMATION: Description of Artificial Sequence: Synthetic
       Sequence

<400> SEQUENCE: 78
ttctcggttg gtctctggcg gagcgaatca tacgaagaca ttccaacgtt ttgtcttgtg      60
tatgattcgc ttttccc                                                    77

<210> SEQ ID NO 79
<211> LENGTH: 78
<212> TYPE: DNA
<213> ORGANISM: Artificial Sequence
<220> FEATURE:
<223> OTHER INFORMATION: Description of Artificial Sequence: Synthetic
       Sequence

<400> SEQUENCE: 79
ttctcggttg gtctctggcg gagcggatca gacacgagac attgcggact tttgtcttgt      60
gtatgattcg cttttccc                                                   78

<210> SEQ ID NO 80
<211> LENGTH: 77
<212> TYPE: DNA
<213> ORGANISM: Artificial Sequence
<220> FEATURE:
<223> OTHER INFORMATION: Description of Artificial Sequence: Synthetic
       Sequence

<400> SEQUENCE: 80
ttctcggttg gtctctggcg gagcgatcag acacgaaaca ttgcggactt ttgtcttgtg      60
tatgattcgc ttttccc                                                    77

<210> SEQ ID NO 81
<211> LENGTH: 77
<212> TYPE: DNA
<213> ORGANISM: Artificial Sequence
<220> FEATURE:
<223> OTHER INFORMATION: Description of Artificial Sequence: Synthetic
       Sequence

<400> SEQUENCE: 81
ttctcggttg gtctctggcg gagcatacac gacgtcattc tagcgttttg acgtcttgtg      60
tatgattcgc ttttccc                                                    77

<210> SEQ ID NO 82
<211> LENGTH: 78
<212> TYPE: DNA
<213> ORGANISM: Artificial Sequence
<220> FEATURE:
<223> OTHER INFORMATION: Description of Artificial Sequence: Synthetic
       Sequence

<400> SEQUENCE: 82
ttctcggttg gtctctggcg gagcagaaac aagaatcatt cttagcgttt tgattcttgt      60
gtatgattcg cttttccc                                                   78

<210> SEQ ID NO 83
<211> LENGTH: 74
<212> TYPE: DNA
<213> ORGANISM: Artificial Sequence
<220> FEATURE:
<223> OTHER INFORMATION: Description of Artificial Sequence: Synthetic
       Sequence

<400> SEQUENCE: 83

```
ttctcggttg gtctctggcg gagcatacac gacgtcattc tagcgttttg tcttgtgtat    60
gattcgcttt tccc                                                      74
```

<210> SEQ ID NO 84
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 84

```
ttctcggttg gtctctggcg gagcgaatcg gacatcaagg gttccagcag tgcttcttgt    60
gtatgattcg cttttccc                                                  78
```

<210> SEQ ID NO 85
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 85

```
ttctcggttg gtctctggcg gagcggatca gacacgaaac attgcggact tttgtcttgt    60
gtatgattcg cttttccc                                                  78
```

<210> SEQ ID NO 86
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 86

```
ttctcggttg gtctctggcg gagcatgcac agcgacattc tcagcgtttt gtcgtcttgt    60
gtatgattcg cttttccc                                                  78
```

<210> SEQ ID NO 87
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 87

```
ttctcggttg gtctctggcg gagcaggagc aagaatcatt cttagcgttt tgattcttgt    60
gtatgattcg cttttccc                                                  78
```

<210> SEQ ID NO 88
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 88

```
ttctcggttg gtctctggcg gagcagaagc aagaatcatt cttagcgttt tgattcttgt    60
gtatgattcg cttttccc                                                  78
```

<210> SEQ ID NO 89
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 89
ttctcggttg gtctctggcg gagcacgtcg gggggcgtt gggacgggca gacgtcttgt      60
gtatgattcg cttttccc                                                  78

<210> SEQ ID NO 90
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 90
ttctcggttg gtctctggcg gagcacatcg gggggcgtt gggacaggca gatgtcttgt      60
gtatgattcg cttttccc                                                  78

<210> SEQ ID NO 91
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 91
ttctcggttg gtctctggcg gagcatgtcg gggggcgtt gggacgggca ggctcttgtg      60
tatgattcgc ttttccc                                                   77

<210> SEQ ID NO 92
<211> LENGTH: 79
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 92
ttctcggttg gtctctggcg gagcacatcg gggggcgtt ggggaaaggc agatgtcttg      60
tgtatgattc gcttttccc                                                 79

<210> SEQ ID NO 93
<211> LENGTH: 79
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 93
ttctcggttg gtctctggcg gagcacgtcg gggggccct ggggacgggc aggcgtcttg      60
tgtatgattc gcttttccc                                                 79

<210> SEQ ID NO 94
<211> LENGTH: 78

```
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 94
ttctcggttg gtctctggcg gagcacaccg gggggctgc gggcaaggcg ggtgtcttgt    60
gtatgattcg cttttccc                                                78

<210> SEQ ID NO 95
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 95
ttctcggttg gtctctggcg gagcacaccg gggggctgg gggaaaggcc ggtgtcttgt    60
gtatgattcg cttttccc                                                78

<210> SEQ ID NO 96
<211> LENGTH: 74
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 96
ttctcggttg gtctctggcg gagcgcgagg gtgtggcgtg ggtggcgcga tcttgtgtat    60
gattcgcttt tccc                                                    74

<210> SEQ ID NO 97
<211> LENGTH: 74
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 97
ttctcggttg gtctctggcg gagcgcaagg gtgtggcgtg ggtggcgcga tcttgtgtat    60
gattcgcttt tccc                                                    74

<210> SEQ ID NO 98
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 98
ttctcggttg gtctctggcg gagcacggga gggtgtggag tgggtggcgc gggctcttgt    60
gtatgattcg cttttccc                                                78

<210> SEQ ID NO 99
<211> LENGTH: 78
<212> TYPE: DNA
<213> ORGANISM: Artificial Sequence
<220> FEATURE:
<223> OTHER INFORMATION: Description of Artificial Sequence: Synthetic
```

Sequence

<400> SEQUENCE: 99
ttctcggttg gtctctggcg gagcacggga gggtgtggag tgggtggcgc gggctcttgt    60
gtatgattcg cttttccc                                                  78

<210> SEQ ID NO 100
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 100
ttctcggttg gtctctggcg gagcgaagca tacgaagaca ttccaacgtt ttgtcttgtg    60
tatgattcgc ttttccc                                                   77

<210> SEQ ID NO 101
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 101
ttctcggttg gtctctggcg gagcggatca gacacgagac attgcggact tttgtcttgt    60
gtatgattcg cttttccc                                                  78

<210> SEQ ID NO 102
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 102
ttctcggttg gtctctggcg gagcgaaagc atacgaagac attccaacgt tttgtcttgt    60
gtatgattcg cttttccc                                                  78

<210> SEQ ID NO 103
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 103
ttctcggttg gtctctggcg gagcgaagca tacgaagaca ttccaacgtt ttgtcttgtg    60
tatgattcgc ttttccc                                                   77

<210> SEQ ID NO 104
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 104

-continued

```
ttctcggttg gtctctggcg gagcagaagc atacgaagac attccaacgt tttgtcttgt      60
gtatgattcg cttttccc                                                   78

<210> SEQ ID NO 105
<211> LENGTH: 76
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 105
ttctcggttg gtctctggcg gagcgaacat acgaagacat tccaacgttt tgtcttgtgt      60
atgattcgct tttccc                                                     76

<210> SEQ ID NO 106
<211> LENGTH: 77
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 106
ttctcggttg gtctctggcg gagcatacac gacgtcattc tagcgttttg acgtcttgtg      60
tatgattcgc ttttccc                                                    77

<210> SEQ ID NO 107
<211> LENGTH: 51
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 107
tggcggagca caccgggggg gctgcgggca aggcgggtgt cttgtgtatg a              51

<210> SEQ ID NO 108
<211> LENGTH: 51
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 108
tggcggagca cgtcgggggg gcgttgggac gggcagacgt cttgtgtatg a              51

<210> SEQ ID NO 109
<211> LENGTH: 51
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 109
tggcggagca cgggagggtg tggagtgggt ggcgcgggct cttgtgtatg a              51

<210> SEQ ID NO 110
<211> LENGTH: 51
<212> TYPE: DNA
<213> ORGANISM: Artificial Sequence
<220> FEATURE:
```

-continued

<223> OTHER INFORMATION: Description of Artificial Sequence: Synthetic
     Sequence
<220> FEATURE:
<221> NAME/KEY: modified_base
<222> LOCATION: (1)..(10)
<223> OTHER INFORMATION: bases at positions 1-10 are linked by
     phosphorothioate linkages

<400> SEQUENCE: 110
tggcggagca caccgggggg gctgcgggca aggcgggtgt cttgtgtatg a          51

<210> SEQ ID NO 111
<211> LENGTH: 51
<212> TYPE: DNA
<213> ORGANISM: Artificial Sequence
<220> FEATURE:
<223> OTHER INFORMATION: Description of Artificial Sequence: Synthetic
     Sequence
<220> FEATURE:
<221> NAME/KEY: modified_base
<222> LOCATION: (1)..(10)
<223> OTHER INFORMATION: bases at positions 1-10 are linked by
     phosphorothioate linkages

<400> SEQUENCE: 111
tggcggagca cgtcgggggg gcgttgggac gggcagacgt gttgtgtatg a          51

<210> SEQ ID NO 112
<211> LENGTH: 51
<212> TYPE: DNA
<213> ORGANISM: Artificial Sequence
<220> FEATURE:
<223> OTHER INFORMATION: Description of Artificial Sequence: Synthetic
     Sequence
<220> FEATURE:
<221> NAME/KEY: modified_base
<222> LOCATION: (1)..(10)
<223> OTHER INFORMATION: bases at positions 1-10 are linked by
     phosphorothioate linkages

<400> SEQUENCE: 112
tggcggagca cgggagggtg tggagtgggt ggcgcgggct gttgtgtatg a          51

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
     Sequence

<400> SEQUENCE: 113
acaccggggg ggctgcgggc aaggcgggtg                                  30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
     Sequence

<400> SEQUENCE: 114
acgtcggggg ggcgttggga cgggcagacg                                  30

<210> SEQ ID NO 115
<211> LENGTH: 30
<212> TYPE: DNA
<213> ORGANISM: Artificial Sequence

```
<220> FEATURE:
<223> OTHER INFORMATION: Description of Artificial Sequence: Synthetic
      Sequence

<400> SEQUENCE: 115
acgggagggt gtggagtggg tggcgcgggc                                         30

<210> SEQ ID NO 116
<211> LENGTH: 63
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 116
acgtcggggg ggcgttggga cgggcagacg tttacgtcgg ggggcgttg ggacgggcag        60 acg                                                                      63

<210> SEQ ID NO 117
<211> LENGTH: 67
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (34)
<223> OTHER INFORMATION: n at position 34 is a 1,3-glycerol linkage

<400> SEQUENCE: 117
acgtcggggg ggcgttggga cgggcagacg tttntttgca gacgggcagg gttgcggggg        60
ggctgca                                                                  67

<210> SEQ ID NO 118
<211> LENGTH: 63
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (31)..(33)
<223> OTHER INFORMATION: n at positions 31 and 33 is a hexaethylene
      glyc unit; n at position 32 is a 1,3-glycerol linkage

<400> SEQUENCE: 118
acgtcggggg ggcgttggga cgggcagacg nnngcagacg ggcagggttg cggggggggct       60 gca                                                                      63

<210> SEQ ID NO 119
<211> LENGTH: 64
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 119
atgcctaagt ttcgaacgcg gctagccagc ttttgctggc tagccgcgtt cgaaacttag        60
gcat                                                                     64
```